US009181387B2

(12) United States Patent
Crawford et al.

(10) Patent No.: US 9,181,387 B2
(45) **Date of Patent: *Nov. 10, 2015**

(54) POLYESTER COMPOSITIONS WHICH COMPRISE CYCLOBUTANEDIOL HAVING CERTAIN CIS/TRANS RATIOS

(75) Inventors: Emmett Dudley Crawford, Kingsport, TN (US); David Scott Porter, Blountville, TN (US); Gary Wayne Connell, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/162,870

(22) Filed: Jun. 17, 2011

(65) Prior Publication Data

US 2012/0021158 A1 Jan. 26, 2012

Related U.S. Application Data

(63) Continuation of application No. 11/391,137, filed on Mar. 28, 2006, now Pat. No. 7,985,827.

(60) Provisional application No. 60/691,567, filed on Jun. 17, 2005, provisional application No. 60/731,454, filed on Oct. 28, 2005, provisional application No. 60/731,389, filed on Oct. 28, 2005, provisional application No. 60/739,058, filed on Nov. 22, 2005, provisional application No. 60/738,869, filed on Nov. 22, 2005, provisional application No. 60/750,692, filed on Dec. 15, 2005, provisional application No. 60/750,693, filed on Dec. 15, 2005, provisional application No. 60/750,682, filed on Dec. 15, 2002, provisional application No. 60/750,547, filed on Dec. 15, 2005.

(51) Int. Cl.

| | |
|---|---|
| ***C08G 63/00*** | (2006.01) |
| ***C08L 67/02*** | (2006.01) |
| ***C08G 63/199*** | (2006.01) |
| ***A01G 9/14*** | (2006.01) |
| ***A47F 5/00*** | (2006.01) |
| ***B01D 61/30*** | (2006.01) |
| ***B32B 17/10*** | (2006.01) |
| ***B32B 27/36*** | (2006.01) |
| ***B65D 1/02*** | (2006.01) |
| ***C08J 5/18*** | (2006.01) |
| ***C08J 7/04*** | (2006.01) |
| ***C08J 7/12*** | (2006.01) |

(Continued)

(52) U.S. Cl.

CPC ........... *C08G 63/199* (2013.01); *A01G 9/1438* (2013.01); *A47F 5/00* (2013.01); *B01D 61/30* (2013.01); *B32B 17/10018* (2013.01); *B32B 27/36* (2013.01); *B65D 1/0207* (2013.01); *B65D 23/10* (2013.01); *B65D 25/00* (2013.01); *B65D 43/00* (2013.01); *C08J 5/18* (2013.01); *C08J 7/047* (2013.01); *C08J 7/123* (2013.01); *C08K 3/32* (2013.01); *C08K 5/521* (2013.01); *C08L 67/02* (2013.01); *C08L 69/00* (2013.01); *E01F 8/0005* (2013.01); *E04D 13/03* (2013.01); *G02F 1/133606* (2013.01); *A61J 17/00* (2013.01); *A61M 1/16* (2013.01); *B29B 2911/14986* (2013.01); *B29C 49/00* (2013.01); *B29K 2067/00* (2013.01); *B29L 2031/7542* (2013.01); *C08J 2367/00* (2013.01); *C08J 2367/02* (2013.01); *C08J 2483/00* (2013.01); *C08K 2201/014* (2013.01); *C08L 101/00* (2013.01); *G02B 1/105* (2013.01); *G02B 5/3083* (2013.01); *Y10T 428/139* (2015.01); *Y10T 428/1352* (2015.01); *Y10T 428/1397* (2015.01); *Y10T 428/161* (2015.01); *Y10T 428/162* (2015.01); *Y10T 428/24107* (2015.01); *Y10T 428/24479* (2015.01); *Y10T 428/24942* (2015.01); *Y10T 428/31504* (2015.04); *Y10T 428/31507* (2015.04); *Y10T 428/31663* (2015.04); *Y10T 428/31786* (2015.04)

(58) Field of Classification Search

CPC ........... C08L 67/00; C08K 3/32; C08G 3/183
USPC .......... 528/302, 304, 305, 307; 525/165, 173, 525/177, 390, 397, 425, 439, 444

See application file for complete search history.

(56) References Cited

U.S. PATENT DOCUMENTS

| | | | |
|---|---|---|---|
| 1,602,699 | A | 10/1926 | Nightingale |
| 2,160,841 | A | 6/1939 | Dreyfus |

(Continued)

FOREIGN PATENT DOCUMENTS

| | | |
|---|---|---|
| BE | 615850 | 4/1962 |
| CA | 2035149 | 8/1991 |

(Continued)

OTHER PUBLICATIONS

USPTO Office Action dated Oct. 17, 2011 for copending U.S. Appl. No. 12/853,717.

(Continued)

*Primary Examiner* — Ling Choi
*Assistant Examiner* — Gennadiy Mesh
(74) *Attorney, Agent, or Firm* — Betty J. Boshears

(57) ABSTRACT

Described are polyester compositions comprising (a) a dicarboxylic acid component comprising 80 to 100 mole % terephthalic acid residues; optionally, aromatic dicarboxylic acid or aliphatic dicarboxylic acid residues; 30 to 40 mole % of 2,2,4,4-tetramethyl-1,3-cyclobutanediol residues, where said 2,2,4,4-tetramethyl-1,3-cyclobutanediol residues comprise at least 55 mole % cis-2,2,4,4-tetramethyl-1,3-cyclobutanediol; and 60 to 70 mole % 1,4-cyclohexanedimethanol residues.

32 Claims, 3 Drawing Sheets

(51) Int. Cl.

| | |
|---|---|
| ***C08K 3/32*** | (2006.01) |
| ***C08K 5/521*** | (2006.01) |
| ***C08L 69/00*** | (2006.01) |
| ***E01F 8/00*** | (2006.01) |
| ***E04D 13/03*** | (2006.01) |
| ***G02F 1/1335*** | (2006.01) |
| ***B65D 23/10*** | (2006.01) |
| ***B65D 25/00*** | (2006.01) |
| ***B65D 43/00*** | (2006.01) |
| *A61J 17/00* | (2006.01) |
| *A61M 1/16* | (2006.01) |
| *B29C 49/00* | (2006.01) |
| *B29K 67/00* | (2006.01) |
| *B29L 31/00* | (2006.01) |
| *C08L 101/00* | (2006.01) |
| *G02B 1/10* | (2015.01) |
| *G02B 5/30* | (2006.01) |

(56) References Cited

U.S. PATENT DOCUMENTS

| | | | |
|---|---|---|---|
| 2,202,046 | A | 5/1940 | Dreyfus et al. |
| 2,278,537 | A | 4/1942 | Dreyfus et al. |
| 2,720,507 | A | 10/1955 | Caldwell |
| 2,806,064 | A | 9/1957 | McKlveen |
| 2,901,466 | A | 8/1959 | Kibler |
| 2,936,324 | A | 5/1960 | Hasek et al. |
| 3,000,906 | A | 9/1961 | Hasek et al. |
| 3,030,335 | A | 4/1962 | Goldberg |
| 3,062,852 | A | 11/1962 | Martin et al. |
| 3,075,952 | A | 1/1963 | Coover et al. |
| 3,091,600 | A | 5/1963 | Caldwell et al. |
| 3,169,121 | A | 2/1965 | Goldberg et al. |
| 3,190,928 | A | 6/1965 | Elam et al. |
| 3,201,474 | A | 8/1965 | Hasek et al. |
| 3,207,814 | A | 9/1965 | Goldberg et al. |
| 3,218,372 | A | 11/1965 | Okamura et al. |
| 3,227,764 | A | 1/1966 | Martin et al. |
| 3,236,899 | A | 2/1966 | Clark |
| 3,249,652 | A | 5/1966 | Quisenberry |
| 3,259,469 | A | 7/1966 | Painter et al. |
| 3,287,390 | A | 11/1966 | Poos et al. |
| 3,288,854 | A | 11/1966 | Martin |
| 3,312,741 | A | 4/1967 | Martin |
| 3,313,777 | A | 4/1967 | Elam et al. |
| 3,317,466 | A | 5/1967 | Caldwell et al. |
| 3,329,722 | A | 7/1967 | Rylander |
| 3,360,547 | A | 12/1967 | Wilson et al. |
| 3,366,689 | A | 1/1968 | Maeda et al. |
| 3,386,935 | A | 6/1968 | Jackson et al. |
| 3,403,181 | A | 9/1968 | Painter et al. |
| T858,012 | I4 | 7/1969 | Caldwell et al. |
| 3,484,339 | A | 12/1969 | Caldwell |
| 3,502,620 | A | 3/1970 | Caldwell |
| T873,016 | I4 | 4/1970 | Gilkey et al. |
| 3,541,059 | A | 11/1970 | Schaper |
| 3,546,177 | A | 12/1970 | Kibler et al. |
| 3,629,202 | A | 12/1971 | Gilkey et al. |
| RE27,682 | E | 6/1973 | Hermann et al. |
| 3,772,405 | A | 11/1973 | Hamb |
| 3,799,953 | A | 3/1974 | Freitag et al. |
| 3,907,754 | A | 9/1975 | Tershansy et al. |
| 3,915,913 | A | 10/1975 | Jackson, Jr. et al. |
| 3,962,189 | A | 6/1976 | Russin et al. |
| 4,001,184 | A | 1/1977 | Scott |
| 4,010,145 | A | 3/1977 | Russin et al. |
| 4,046,933 | A | 9/1977 | Stefanik |
| 4,056,504 | A | 11/1977 | Grundmeier et al. |
| 4,084,889 | A | 4/1978 | Vischer, Jr. |
| 4,125,572 | A | 11/1978 | Scott |
| 4,156,069 | A | 5/1979 | Prevorsek et al. |
| 4,160,383 | A | 7/1979 | Rauschenberger |
| 4,185,009 | A | 1/1980 | Idel et al. |
| 4,188,314 | A | 2/1980 | Fox et al. |
| 4,194,038 | A | 3/1980 | Baker et al. |
| 4,263,364 | A | 4/1981 | Seymour et al. |
| 4,264,751 | A | 4/1981 | Scheibelhoffer |
| 4,356,299 | A | 10/1982 | Cholod et al. |
| 4,367,186 | A | 1/1983 | Adelmann et al. |
| 4,379,802 | A | 4/1983 | Weaver et al. |
| 4,384,106 | A | 5/1983 | Go et al. |
| 4,391,954 | A | 7/1983 | Scott |
| 4,424,140 | A | 1/1984 | Weinberg et al. |
| 4,426,512 | A | 1/1984 | Barbee et al. |
| 4,427,614 | A | 1/1984 | Barham et al. |
| 4,430,484 | A | 2/1984 | Quinn |
| 4,431,793 | A | 2/1984 | Rosenquist |
| 4,452,933 | A | 6/1984 | McCready |
| 4,465,820 | A | 8/1984 | Miller et al. |
| 4,469,861 | A | 9/1984 | Mark et al. |
| 4,480,086 | A | 10/1984 | 'Neill |
| 4,525,504 | A | 6/1985 | Morris et al. |
| 4,578,295 | A | 3/1986 | Jabarin |
| 4,578,437 | A | 3/1986 | Light et al. |
| 4,642,959 | A | 2/1987 | Swiech, Jr. et al. |
| 4,738,880 | A | 4/1988 | Asada et al. |
| 4,749,773 | A | 6/1988 | Weaver et al. |
| 4,786,692 | A | 11/1988 | Allen et al. |
| 4,816,308 | A | 3/1989 | Shimizu et al. |
| 4,826,903 | A | 5/1989 | Weaver et al. |
| 4,845,188 | A | 7/1989 | Weaver et al. |
| 4,880,592 | A | 11/1989 | Martini et al. |
| 4,882,412 | A | 11/1989 | Weaver et al. |
| 4,892,922 | A | 1/1990 | Weaver et al. |
| 4,892,923 | A | 1/1990 | Weaver et al. |
| 4,937,134 | A | 6/1990 | Schrenk et al. |
| 4,939,186 | A | 7/1990 | Nelson et al. |
| 4,976,057 | A | 12/1990 | Bianchi |
| 4,981,898 | A | 1/1991 | Bassett |
| 4,985,342 | A | 1/1991 | Muramoto et al. |
| 5,017,679 | A | 5/1991 | Chang et al. |
| 5,017,680 | A | 5/1991 | Sublett |
| 5,034,252 | A | 7/1991 | Nilsson et al. |
| 5,104,450 | A | 4/1992 | Sand et al. |
| 5,118,760 | A | 6/1992 | Blakely et al. |
| 5,118,847 | A | 6/1992 | Jackson et al. |
| 5,142,088 | A | 8/1992 | Phelps et al. |
| 5,169,994 | A | 12/1992 | Sumner, Jr. et al. |
| 5,183,863 | A | 2/1993 | Nakamura et al. |
| 5,191,038 | A | 3/1993 | Krabbenhoft et al. |
| 5,207,967 | A | 5/1993 | Small, Jr. et al. |
| 5,219,510 | A | 6/1993 | Machell et al. |
| 5,224,958 | A | 7/1993 | Warunek et al. |
| 5,239,020 | A | 8/1993 | Morris |
| 5,256,761 | A | 10/1993 | Blount, Jr. |
| 5,258,556 | A | 11/1993 | Sumner, Jr. et al. |
| 5,268,219 | A | 12/1993 | Harada et al. |
| 5,288,715 | A | 2/1994 | Machell et al. |
| 5,288,764 | A | 2/1994 | Rotter et al. |
| 5,292,783 | A | 3/1994 | Buchanan et al. |
| 5,310,611 | A | 5/1994 | Okabe et al. |
| 5,310,787 | A | 5/1994 | Kutsuwa et al. |
| 5,326,584 | A | 7/1994 | Kamel et al. |
| 5,331,034 | A | 7/1994 | Pfahler et al. |
| 5,333,073 | A | 7/1994 | Suzuki |
| 5,354,791 | A | 10/1994 | Gallucci |
| 5,372,864 | A | 12/1994 | Weaver et al. |
| 5,372,879 | A | 12/1994 | Handa et al. |
| 5,378,796 | A | 1/1995 | George et al. |
| 5,382,292 | A | 1/1995 | Conroy et al. |
| 5,384,377 | A | 1/1995 | Weaver et al. |
| 5,474,735 | A | 12/1995 | Krishnakumar et al. |
| 5,475,144 | A | 12/1995 | Watson et al. |
| 5,480,926 | A | 1/1996 | Fagerburg et al. |
| 5,486,562 | A | 1/1996 | Borman et al. |
| 5,489,665 | A | 2/1996 | Yamato et al. |
| 5,494,992 | A | 2/1996 | Kanno et al. |
| 5,498,668 | A | 3/1996 | Scott |
| 5,498,688 | A | 3/1996 | Oshino et al. |
| 5,506,014 | A | 4/1996 | Minnick |
| 5,523,382 | A | 6/1996 | Beavers et al. |
| 5,534,609 | A | 7/1996 | Lewis et al. |

(56) References Cited

U.S. PATENT DOCUMENTS

| | | | |
|---|---|---|---|
| 5,552,512 | A | 9/1996 | Sublett |
| 5,591,530 | A | 1/1997 | Warner et al. |
| 5,633,340 | A | 5/1997 | Hoffman et al. |
| 5,650,453 | A | 7/1997 | Eckberg et al. |
| 5,654,347 | A | 8/1997 | Khemani et al. |
| 5,656,715 | A | 8/1997 | Dickerson et al. |
| 5,668,243 | A | 9/1997 | Yau et al. |
| 5,681,918 | A | 10/1997 | Adams et al. |
| 5,688,874 | A | 11/1997 | Hoffman |
| 5,696,176 | A | 12/1997 | Khemani et al. |
| 5,705,575 | A | 1/1998 | Kelsey |
| 5,783,307 | A | 7/1998 | Fagerburg et al. |
| 5,804,617 | A | 9/1998 | Hoffman et al. |
| 5,814,679 | A | 9/1998 | Eckberg et al. |
| 5,859,116 | A | 1/1999 | Shih |
| 5,863,622 | A | 1/1999 | Jester |
| 5,902,631 | A | 5/1999 | Wang et al. |
| 5,907,026 | A | 5/1999 | Factor et al. |
| 5,942,585 | A | 8/1999 | Scott et al. |
| 5,955,565 | A | 9/1999 | Morris et al. |
| 5,958,539 | A | 9/1999 | Eckart et al. |
| 5,958,581 | A | 9/1999 | Khanarian et al. |
| 5,959,066 | A | 9/1999 | Charbonneau et al. |
| 5,962,625 | A | 10/1999 | Yau |
| 5,977,347 | A | 11/1999 | Shuto et al. |
| 5,989,663 | A | 11/1999 | Morris et al. |
| 6,001,910 | A | 12/1999 | Blumenthal et al. |
| 6,005,059 | A | 12/1999 | Scott et al. |
| 6,011,124 | A | 1/2000 | Scott et al. |
| 6,012,597 | A | 1/2000 | Nishihara et al. |
| 6,022,603 | A | 2/2000 | Umeda et al. |
| 6,025,061 | A | 2/2000 | Khanarian et al. |
| 6,030,671 | A | 2/2000 | Yang et al. |
| 6,037,424 | A | 3/2000 | Scott et al. |
| 6,043,322 | A | 3/2000 | Scott et al. |
| 6,044,996 | A | 4/2000 | Carew et al. |
| 6,063,464 | A | 5/2000 | Charbonneau et al. |
| 6,063,465 | A | 5/2000 | Charbonneau et al. |
| 6,063,495 | A | 5/2000 | Charbonneau et al. |
| 6,084,019 | A | 7/2000 | Matayabas et al. |
| 6,096,854 | A | 8/2000 | Morris et al. |
| 6,114,575 | A | 9/2000 | McMahon et al. |
| 6,120,477 | A | 9/2000 | Campbell et al. |
| 6,120,889 | A | 9/2000 | Turner et al. |
| 6,126,992 | A | 10/2000 | Khanarian et al. |
| 6,127,492 | A | 10/2000 | Nagashima et al. |
| 6,146,228 | A | 11/2000 | Mougin et al. |
| 6,150,494 | A | 11/2000 | Wang et al. |
| 6,183,848 | B1 | 2/2001 | Turner et al. |
| 6,191,209 | B1 | 2/2001 | Andrews et al. |
| 6,211,309 | B1 | 4/2001 | McIntosh et al. |
| 6,221,556 | B1 | 4/2001 | Gallucci et al. |
| 6,225,436 | B1 | 5/2001 | Eiffler et al. |
| 6,232,504 | B1 | 5/2001 | Barteau et al. |
| 6,239,210 | B1 | 5/2001 | Kim et al. |
| 6,255,523 | B1 | 7/2001 | Panandiker et al. |
| 6,287,656 | B1 | 9/2001 | Turner et al. |
| 6,307,006 | B1 | 10/2001 | Konig et al. |
| 6,309,718 | B1 | 10/2001 | Sprayberry |
| 6,320,042 | B1 | 11/2001 | Michihata et al. |
| 6,323,291 | B1 | 11/2001 | Mason et al. |
| 6,323,304 | B1 | 11/2001 | Lemmon et al. |
| 6,342,304 | B1 | 1/2002 | Buchanan et al. |
| 6,352,783 | B1 | 3/2002 | Fagerburg |
| 6,354,986 | B1 | 3/2002 | Hlavinka et al. |
| 6,359,070 | B1 | 3/2002 | Khanarian et al. |
| 6,406,792 | B1 | 6/2002 | Briquet et al. |
| 6,437,083 | B1 | 8/2002 | Brack et al. |
| 6,448,334 | B1 | 9/2002 | Verhoogt et al. |
| 6,458,468 | B1 | 10/2002 | Moskala et al. |
| 6,504,002 | B1 | 1/2003 | Karlik et al. |
| 6,559,272 | B1 | 5/2003 | Jeon et al. |
| 6,573,328 | B2 | 6/2003 | Kropp et al. |
| 6,576,717 | B1 | 6/2003 | Kuo et al. |
| 6,599,994 | B2 | 7/2003 | Shelby et al. |
| 6,639,067 | B1 | 10/2003 | Brinegar et al. |
| 6,656,577 | B1 | 12/2003 | Adelman et al. |
| 6,669,980 | B2 | 12/2003 | Hansen |
| 6,723,768 | B2 | 4/2004 | Adams et al. |
| 6,733,716 | B2 | 5/2004 | Belcher |
| 6,740,377 | B2 | 5/2004 | Pecorini et al. |
| 6,773,653 | B2 | 8/2004 | Miller et al. |
| 6,818,293 | B1 | 11/2004 | Keep et al. |
| 6,818,730 | B2 | 11/2004 | Brandenburg et al. |
| 6,846,440 | B2 | 1/2005 | Flynn et al. |
| 6,846,508 | B1 | 1/2005 | Colas et al. |
| 6,896,966 | B2 | 5/2005 | Crawford et al. |
| 6,908,650 | B2 | 6/2005 | Odorisio et al. |
| 6,914,120 | B2 | 7/2005 | Germroth et al. |
| 7,037,576 | B2 | 5/2006 | Willham et al. |
| 7,048,978 | B2 | 5/2006 | Tanaka et al. |
| 7,053,143 | B2 | 5/2006 | Mori et al. |
| 7,122,661 | B2 | 10/2006 | Fleche et al. |
| 7,169,880 | B2 | 1/2007 | Shelby et al. |
| 7,273,894 | B2 | 9/2007 | Shelby et al. |
| 7,297,755 | B2 | 11/2007 | Shelby et al. |
| 7,354,628 | B2 | 4/2008 | Steube |
| 7,375,154 | B2 | 5/2008 | Stafford et al. |
| 7,427,430 | B2 | 9/2008 | Rhee et al. |
| 7,468,409 | B2 | 12/2008 | Pearson et al. |
| 7,482,397 | B2 | 1/2009 | Pearson et al. |
| 8,415,450 | B2 | 4/2013 | Crawford et al. |
| 8,501,292 | B2 | 8/2013 | Pecorini et al. |
| 2001/0029324 | A1 | 10/2001 | Walker et al. |
| 2001/0031805 | A1 | 10/2001 | Buhler |
| 2001/0034419 | A1 | 10/2001 | Kanayama et al. |
| 2001/0044003 | A1 | 11/2001 | Gallucci et al. |
| 2002/0055586 | A1 | 5/2002 | Dalgewicz, III et al. |
| 2002/0128357 | A1 | 9/2002 | Goossens et al. |
| 2002/0132963 | A1 | 9/2002 | Quillen |
| 2002/0137856 | A1 | 9/2002 | Andrews et al. |
| 2002/0188092 | A1 | 12/2002 | Moskala et al. |
| 2002/0198297 | A1 | 12/2002 | Odorisio et al. |
| 2003/0032737 | A1 | 2/2003 | Andrews et al. |
| 2003/0060546 | A1 | 3/2003 | Moskala et al. |
| 2003/0075516 | A1 | 4/2003 | Rothman et al. |
| 2003/0077546 | A1 | 4/2003 | Donovan et al. |
| 2003/0135015 | A1 | 7/2003 | Fujimaki et al. |
| 2003/0139497 | A1 | 7/2003 | Odorisio et al. |
| 2003/0149177 | A1 | 8/2003 | Andrews et al. |
| 2003/0169514 | A1 | 9/2003 | Bourdelais et al. |
| 2003/0187151 | A1 | 10/2003 | Adams et al. |
| 2003/0195295 | A1 | 10/2003 | Mahood et al. |
| 2003/0221716 | A1 | 12/2003 | Olson |
| 2003/0229181 | A1 | 12/2003 | Hariharan et al. |
| 2004/0022526 | A1 | 2/2004 | Kuno et al. |
| 2004/0063864 | A1 | 4/2004 | Adams et al. |
| 2004/0101687 | A1 | 5/2004 | Crawford et al. |
| 2004/0106707 | A1 | 6/2004 | Su et al. |
| 2004/0106767 | A1 | 6/2004 | Simon et al. |
| 2004/0108623 | A1 | 6/2004 | Deeter et al. |
| 2004/0138381 | A1 | 7/2004 | Blasius et al. |
| 2004/0145700 | A1 | 7/2004 | Miniutti et al. |
| 2004/0164279 | A1 | 8/2004 | Stevenson et al. |
| 2004/0202822 | A1 | 10/2004 | Bourdelais et al. |
| 2004/0214984 | A1 | 10/2004 | Keep et al. |
| 2005/0008885 | A1 | 1/2005 | Blakely et al. |
| 2005/0072060 | A1 | 4/2005 | Moncho et al. |
| 2005/0096453 | A1 | 5/2005 | Flynn et al. |
| 2005/0101759 | A1 | 5/2005 | Odorisio et al. |
| 2005/0113556 | A1 | 5/2005 | Strand et al. |
| 2005/0119359 | A1 | 6/2005 | Shelby et al. |
| 2005/0124779 | A1 | 6/2005 | Shelby et al. |
| 2005/0181155 | A1 | 8/2005 | Share et al. |
| 2006/0004151 | A1 | 1/2006 | Shaikh et al. |
| 2006/0036012 | A1 | 2/2006 | Hayes et al. |
| 2006/0094858 | A1 | 5/2006 | Turner et al. |
| 2006/0111481 | A1 | 5/2006 | Pearson et al. |
| 2006/0111519 | A1 | 5/2006 | Strand et al. |
| 2006/0135668 | A1 | 6/2006 | Hayes |
| 2006/0146228 | A1 | 7/2006 | Sogo et al. |
| 2006/0180560 | A1 | 8/2006 | Robinson |
| 2006/0197246 | A1 | 9/2006 | Hale et al. |
| 2006/0199904 | A1 | 9/2006 | Hale et al. |

(56) References Cited

U.S. PATENT DOCUMENTS

| | | | |
|---|---|---|---|
| 2006/0199919 | A1 | 9/2006 | Hale et al. |
| 2006/0228507 | A1 | 10/2006 | Hale et al. |
| 2006/0234073 | A1 | 10/2006 | Hale et al. |
| 2006/0235167 | A1 | 10/2006 | Hale et al. |
| 2006/0247388 | A1 | 11/2006 | Hale et al. |
| 2006/0270773 | A1 | 11/2006 | Hale et al. |
| 2006/0270806 | A1 | 11/2006 | Hale |
| 2007/0071930 | A1 | 3/2007 | Shelby et al. |
| 2008/0092776 | A1 | 4/2008 | Stockl et al. |
| 2009/0093574 | A1 | 4/2009 | Crawford et al. |
| 2010/0204413 | A1 | 8/2010 | Powell et al. |

FOREIGN PATENT DOCUMENTS

| | | | |
|---|---|---|---|
| CN | 101193935 | A | 6/2008 |
| DE | 29 21 868 | A1 | 12/1980 |
| DE | 197 27 709 | | 6/1997 |
| DE | 198 11 773 | A1 | 9/1999 |
| EP | 0 039 838 | A1 | 11/1981 |
| EP | 0 273 144 | | 5/1987 |
| EP | 0 282 277 | | 9/1988 |
| EP | 0 372 846 | | 6/1990 |
| EP | 0 544 008 | A1 | 6/1993 |
| EP | 0 595 413 | A1 | 5/1994 |
| EP | 0 698 631 | | 2/1996 |
| EP | 0 714 764 | A2 | 6/1996 |
| EP | 0 902 052 | A1 | 3/1999 |
| EP | 0 930 531 | A1 | 7/1999 |
| EP | 1 066 825 | A1 | 1/2001 |
| EP | 1 674 496 | A1 | 6/2006 |
| EP | 2168752 | A2 | 3/2010 |
| FR | 1278284 | | 12/1961 |
| FR | 1291273 | | 5/1965 |
| FR | 1432471 | | 2/1966 |
| FR | 1434658 | | 2/1966 |
| FR | 2112400 | | 6/1972 |
| GB | 962913 | | 7/1964 |
| GB | 1041651 | | 9/1966 |
| GB | 1044015 | | 9/1966 |
| GB | 1047043 | | 11/1966 |
| GB | 1090241 | | 11/1967 |
| GB | 1130558 | | 10/1968 |
| GB | 1 278 284 | | 6/1972 |
| GB | 1364732 | | 8/1974 |
| GB | 2216919 | A | 10/1989 |
| JP | 56-88440 | A | 12/1979 |
| JP | 03207743 | | 9/1991 |
| JP | 65-01040 | | 2/1994 |
| JP | 9-59371 | A | 4/1997 |
| JP | 11-222516 | | 8/1999 |
| JP | 2001-066701 | | 8/1999 |
| JP | 2000-352620 | A | 12/2000 |
| JP | 2001-098086 | | 4/2001 |
| JP | 2001-214049 | | 8/2001 |
| JP | 2004-244497 | A | 9/2004 |
| JP | 2004-292558 | A | 10/2004 |
| KR | 2001/089942 | | 10/2001 |
| KR | 2003/054611 | | 7/2003 |
| WO | WO 97/01118 | | 1/1997 |
| WO | WO 01/06981 | | 2/2001 |
| WO | WO 01/85824 | A2 | 11/2001 |
| WO | WO 02/055570 | A1 | 7/2002 |
| WO | WO 02/059207 | | 8/2002 |
| WO | WO2004/009146 | A1 | 1/2004 |
| WO | WO 2004/039860 | | 5/2004 |
| WO | WO 2004/104077 | | 12/2004 |
| WO | WO 2004/106988 | A2 | 12/2004 |
| WO | WO 2005/007735 | A2 | 1/2005 |
| WO | WO 2005/026241 | | 3/2005 |
| WO | WO 2006/025827 | | 3/2006 |
| WO | WO 2006/127755 | A2 | 11/2006 |
| WO | WO 2006/127831 | A1 | 11/2006 |
| WO | WO 2007/053434 | A1 | 5/2007 |
| WO | WO 2007/053548 | A2 | 5/2007 |
| WO | WO 2007/053549 | A1 | 5/2007 |
| WO | WO 2007/053550 | | 5/2007 |
| WO | 2007123631 | A1 | 11/2007 |
| WO | WO 2009/070238 | A2 | 4/2010 |

OTHER PUBLICATIONS

USPTO Notice of Allowance dated Oct. 25, 2011 for copending U.S. Appl. No. 12/900,060.

USPTO Office Action dated Nov. 2, 2011 for copending U.S. Appl. No. 12/479,893.

USPTO Notice of Allowance dated Nov. 10, 2011 for copending U.S. Appl. No. 12/943,217.

USPTO Office Action dated Oct. 31, 2011 for U.S. Appl. No. 12/639,324.

USPTO Notice of Allowance dated Nov. 2, 2011 for copending U.S. Appl. No. 12/390,694.

USPTO Notice of Allowance dated Nov. 28, 2011 for copending U.S. Appl. No. 12/274,692.

USPTO Notice of Allowance dated Dec. 16, 2011 for copending U.S. Appl. No. 12/390,694.

USPTO Office Action dated Dec. 21, 2011 for copending U.S. Appl. No. 12/091,570.

USPTO Notice of Allowance dated Oct. 17, 2011 for copending U.S. Appl. No. 11/390,794.

Abstract of U.S. Defense Publication T869,015, 869 O.G. 714, Dec. 16, 1969.

Abstract of U.S. Defense Publication T875,010, 875 O.G. 342, Jun. 9, 1970.

Chen et al., "The molecular basis for the relationship between the secondary relaxation and mechanical properties of a series of polyester copolymer glasses," Marcromolecules, 32:5944-5955 (1999).

Coover, H. et al., "Copolyester Molding Compositions," Chemical Abstracts Service, XP002391844.

Kelsey, E. et al., "High Impact, Amorphous Terephthalate Copolyesters of Rigid 2,2,4,4-Tetramethyl-1,3-cyclobutanediol with Flexible Diols," Macromolecules, vol. 33, 2000, pp. 5810-5818, American Chemical Society.

"Plastic Additives Handbook," 5$^{th}$ Edition, 2001, pp. 98-108 and pp. 109-112 (Hanser Gardner Publications, Inc., Cincinnati, OH.

Bergen, R. L., Jr., "Stress Cracking of Rigid Thermoplastics," SPE Journal, Jun. 1962.

Scheirs, John, et al., "Modern Polyesters: Chemistry and Technology of Polyesters and Copolyesters," Technology & Engineering, 2003, p. 287.

English language Abstract of JP 02-305816 from Patent Abstracts of Japan, Dec. 19, 1990.

English language translation of Belgian Patent No. BE 615,850, Apr. 13, 1962.

English language translation of French Patent No. FR 1,432,471, Feb. 7, 1966.

English language translation of French Patent No. FR 1,434,658, Feb. 28, 1966.

U.S. Appl. No. 11/390,555, filed Mar. 28, 2006, Emmett Dudley Crawford, et al.

U.S. Appl. No. 11/390,563, filed Mar. 28, 2006, Emmett Dudley Crawford, et al.

U.S. Appl. No. 11/390,629, filed Mar. 28, 2006, Emmett Dudley Crawford, et al.

U.S. Appl. No. 11/390,630, filed Mar. 28, 2006, Emmett Dudley Crawford, et al.

U.S. Appl. No. 11/390,631, filed Mar. 28, 2006, Emmett Dudley Crawford, et al.

U.S. Appl. No. 11/390,654, filed Mar. 28, 2006, Emmett Dudley Crawford, et al.

U.S. Appl. No. 11/390,655, filed Mar. 28, 2006, Emmett Dudley Crawford, et al.

U.S. Appl. No. 11/390,671, filed Mar. 28, 2006, Emmett Dudley Crawford, et al.

U.S. Appl. No. 11/390,672, filed Mar. 28, 2006, Emmett Dudley Crawford, et al.

U.S. Appl. No. 11/390,722, filed Mar. 28, 2006, Emmett Dudley Crawford, et al.

(56) References Cited

OTHER PUBLICATIONS

U.S. Appl. No. 11/390,750, filed Mar. 28, 2006, Emmett Dudley Crawford, et al.
U.S. Appl. No. 11/390,751, filed Mar. 28, 2006, Emmett Dudley Crawford, et al.
U.S. Appl. No. 11/390,752, filed Mar. 28, 2006, Emmett Dudley Crawford, et al.
U.S. Appl. No. 11/390,773, filed Mar. 28, 2006, Emmett Dudley Crawford, et al.
U.S. Appl. No. 11/390,793, filed Mar. 28, 2006, Emmett Dudley Crawford, et al.
U.S. Appl. No. 11/390,794, filed Mar. 28, 2006, Emmett Dudley Crawford, et al.
U.S. Appl. No. 11/390,809, filed Mar. 28, 2006, Wesley Raymond Hale, et al.
U.S. Appl. No. 11/390,811, filed Mar. 28, 2006, Emmett Dudley Crawford, et al.
U.S. Appl. No. 11/390,812, filed Mar. 28, 2006, Wesley Raymond Hale, et al.
U.S. Appl. No. 11/390,814, filed Mar. 28, 2006, Emmett Dudley Crawford, et al.
U.S. Appl. No. 11/390,826, filed Mar. 28, 2006, Emmett Dudley Crawford, et al.
U.S. Appl. No. 11/390,827, filed Mar. 28, 2006, Emmett Dudley Crawford, et al.
U.S. Appl. No. 11/390,836, filed Mar. 28, 2006, Emmett Dudley Crawford, et al.
U.S. Appl. No. 11/390,846, filed Mar. 28, 2006, Wesley Raymond Hale, et al.
U.S. Appl. No. 11/390,847, filed Mar. 28, 2006, Emmett Dudley Crawford, et al.
U.S. Appl. No. 11/390,853, filed Mar. 28, 2006, Emmett Dudley Crawford, et al.
U.S. Appl. No. 11/390,858, filed Mar. 28, 2006, Emmett Dudley Crawford, et al.
U.S. Appl. No. 11/390,864, filed Mar. 28, 2006, Wesley Raymond Hale, et al.
U.S. Appl. No. 11/390,865, filed Mar. 28, 2006, Emmett Dudley Crawford, et al.
U.S. Appl. No. 11/390,882, filed Mar. 28, 2006, Emmett Dudley Crawford, et al.
U.S. Appl. No. 11/390,883, filed Mar. 28, 2006, Thomas Joseph Pecorini, et al.
U.S. Appl. No. 11/390,908, filed Mar. 28, 2006, Wesley Raymond Hale, et al.
U.S. Appl. No. 11/391,063, filed Mar. 28, 2006, Emmett Dudley Crawford, et al.
U.S. Appl. No. 11/391,124, filed Mar. 28, 2006, Wesley Raymond Hale, et al.
U.S. Appl. No. 11/391,125, filed Mar. 28, 2006, Emmett Dudley Crawford, et al.
U.S. Appl. No. 11/391,137, filed Mar. 28, 2006, Emmett Dudley Crawford, et al.
U.S. Appl. No. 11/391,156, filed Mar. 28, 2006, Emmett Dudley Crawford, et al.
U.S. Appl. No. 11/391,485, filed Mar. 28, 2006, Emmett Dudley Crawford, et al.
U.S. Appl. No. 11/391,495, filed Mar. 28, 2006, Emmett Dudley Crawford, et al.
U.S. Appl. No. 11/391,505, filed Mar. 28, 2006, Emmett Dudley Crawford, et al.
U.S. Appl. No. 11/391,565, filed Mar. 28, 2006, Emmett Dudley Crawford, et al.
U.S. Appl. No. 11/391,571, filed Mar. 28, 2006, Emmett Dudley Crawford, et al.
U.S. Appl. No. 11/391,576, filed Mar. 28, 2006, Emmett Dudley Crawford, et al.
U.S. Appl. No. 11/391,642, filed Mar. 28, 2006, Emmett Dudley Crawford, et al.
U.S. Appl. No. 11/391,659, filed Mar. 28, 2006, Emmett Dudley Crawford, et al.
U.S. Appl. No. 11/588,524, filed Oct. 27, 2006, Emmett Dudley Crawford, et al.
U.S. Appl. No. 11/588,458, filed Oct. 27, 2006, Emmett Dudley Crawford, et al.
U.S. Appl. No. 11/588,907, filed Oct. 27, 2006, Emmett Dudley Crawford, et al.
U.S. Appl. No. 11/588,527, filed Oct. 27, 2006, Emmett Dudley Crawford, et al.
U.S. Appl. No. 11/588,906, filed Oct. 27, 2006, Ted Calvin Germroth, et al.
U.S. Appl. No. 11/588,883, filed Oct. 27, 2006, Ted Calvin Germroth, et al.
U.S. Appl. No. 11/588,554, filed Oct. 27, 2006, Emmett Dudley Crawford, et al.
U.S. Appl. No. 11/635,434, filed Dec. 7, 2006, Emmett Dudley Crawford.
U.S. Appl. No. 11/635,433, filed Dec. 7, 2006, Emmett Dudley Crawford.
U.S. Appl. No. 11/439,062, filed May 23, 2006, Wesley Raymond Hale, et al.
U.S. Appl. No. 11/439,340, filed May 23, 2006, Wesley Raymond Hale.
U.S. Appl. No. 11/706,476, filed Feb. 14, 2007, Leslie Shane Moody, et al.
U.S. Appl. No. 11/706,791, filed Feb. 14, 2007, Leslie Shane Moody, et al.
U.S. Appl. No. 12/091,568, filed Apr. 25, 2008, Emmett Dudley Crawford, et al.
U.S. Appl. No. 12/091,566, filed Apr. 25, 2008, Emmett Dudley Crawford, et al.
U.S. Appl. No. 12/091,570, filed Apr. 25, 2008, Ted Calvin Germroth, et al.
U.S. Appl. No. 12/091,572, filed Apr. 25, 2008, Ted Calvin Germroth, et al.
U.S. Appl. No. 12/294,690, filed Sep. 26, 2008, Ted Calvin Germroth et al.
U.S. Appl. No. 12/294,686, filed Sep. 26, 2008, Ted Calvin Germroth et al.
U.S. Appl. No. 12/274,692, filed Nov. 20, 2008, Thomas Joseph Pecorini et al.
U.S. Appl. No. 12/338,453, filed Dec. 18, 2008, Emmett Dudley Crawford, et al.
U.S. Appl. No. 12/361,779, filed Jan. 29, 2009, Emmett Dudley Crawford.
U.S. Appl. No. 12/365,515, filed Feb. 4, 2009, Emmett Dudley Crawford.
Chapter 4—*Processing of Plastics in "Plastics Engineering, 3rd ed"*, R.J. Crawford, Butterworth-Heinemann Publisher, 1998, Oxford, England, pp. 245-342.
Fox equation (T.G. Fox, Session J, Bull. Am. Phys. Soc., 1, 123 (1956)).
*The Technology of Plasticizers*, by J. Kern Sears and Joseph R Darby, published by Society of Plastic Engineers/Wiley and Sons, New York, 1982; pp. 136-139.
Coleman et al., "Polymer Reviews—A Practical Guide to Polymer Miscibility," Polymer 31, pp. 1187-1203 (1990).
"*Hansen Solubility Parameters, a Users Handbook*", by Charles M. Hansen, Chapter 1, CRC Press, 2000, pp. 1-24.
Martinez et al., "*Phase Behavior and Mechanical Properties of Injection Molded Poly (Ethylene Terephthalate ) / Polyarylate Blends*"; Journal of Applied Polymer Science, John Wiley and Sons Inc. New York, US, vol. 45, No. 7, Jul. 5, 1992, p. 1135-1143.
Won Ho Jo et al. : :*Miscibility of poly(ether imide)/poly(ethylene terephthalate) blends*; Polymer Bulletin, Springer, Heidelberg, DE, vol. 33, No. 1,Jun. 1, 1994, p. 113-118 (1994).
Anonymous: "*Poly (ethylene naphthalenedicarboxylate)/ polyetherimide blends*" Research Disclosure, Mason Publications, Hampshire, GB, vol. 283, No. 38, Nov. 1987.
ASTM D1525-06, *Standard Test Method for Vicat Softening Temperature of Plastics*, Mar. 15, 2006.

(56) References Cited

OTHER PUBLICATIONS

ASTM D648-06, *Standard Test Method for Deflection Temperature of Plastics Under Flexural Load in the Edgewise Position*, Mar. 15, 2006.
ASTM D256-06, *Standard Test Methods for Determining the Izod Pendulum Impact Resistance of Plastics*, Mar. 15, 2006.
ASTM D790-03, *Standard Test Methods for Flexural Properties of Unreinforced and Reinforced Plastics and Electrical Insulating Materials*, Mar. 10, 2003.
ASTM D638-03, *Standard Test Method for Tensile Properties of Plastics*, Dec. 1, 2003.
ASTM D3418-03, *Transition Temperatures and Enthalpies of Fusion and Crystallization of Polymers by Differential Scanning Calorimetry*, Dec. 1, 2003.
Database WPI, Section Ch, Week 200536, Derwent Publications Ltd., London, GB; Class A23, AN 2005-355258, XP002396922 & WO 2005-030833 A1 (Kanebo LTD) Apr. 7, 2005 abstract.
Shearer, N.H., "T18-Type 1 Polyesters," Mar. 1966, SPE Annual Technical Conference and Exhibition, XP009080224.
Gachter, Muller, "Taschenbuch der Kunststoff-Additive," 1990, Carl Hanser Verlag Munchen Wien, XP02450422, pp. 96-97.
Gachter, Muller, "Kunstoff-Additive," 1990, Carl Hanser Verlag Munchen Wien, XP 02449987, pp. 96-99.
Brown, R., "Taschenbuch Kunstoff-Additive", 1990, Carl Hanswer Verlag Munchen Wiel, XP002455247, pp. 361-363.
Chang, S. et al., "Effect of Stabilizers on the Preparation of Poly(ethylene Terephthalate)", Journal of Polymer Science, Polymer Chemistry Edition, 1982, vol. 20, pp. 2053-2061, John Wiley & Sons, Inc.
USPTO Office Action dated Mar. 11, 2008 for copending U.S. Appl. No. 11/391,642.
USPTO Office Action dated Mar. 24, 2008 for copending U.S. Appl. No. 11/390,908.
USPTO Office Action dated Apr. 15, 2008 for copending U.S. Appl. No. 11/390,629.
USPTO Office Action dated Apr. 16, 2008 for copending U.S. Appl. No. 11/390,751.
USPTO Office Action dated Apr. 17, 2008 for copending U.S. Appl. No. 11/390,814.
USPTO Office Action dated Jun. 3, 2008 for copending U.S. Appl. No. 11/391,063.
USPTO Office Action dated Sep. 10, 2008 for copending U.S. Appl. No. 11/390,752.
USPTO Office Action dated Sep. 10, 2008 for copending U.S. Appl. No. 11/390,794.
USPTO Office Action dated Sep. 19, 2008 for copending U.S. Appl. No. 11/391,565.
USPTO Office Action dated Oct. 2, 2008 for copending U.S. Appl. No. 11/390,671.
USPTO Office Action dated Sep. 24, 2008 for copending U.S. Appl. No. 11/390,631.
USPTO Office Action dated Oct. 1, 2008 for copending U.S. Appl. No. 11/390,655.
USPTO Office Action dated Sep. 29, 2008, for copending U.S. Appl. No. 11/391,137.
USPTO Office Action dated Sep. 9, 2008 for copending U.S. Appl. No. 11/391/571.
USPTO Office Action dated Oct. 22, 2008 for copending U.S. Appl. No. 11/391,125.
USPTO Office Action dated Oct. 20, 2008 for copending U.S. Appl. No. 11/390,672.
USPTO Office Action dated Oct. 8, 2008 for copending U.S. Appl. No. 11/390,853.
USPTO Office Action dated Oct. 9, 2008 for copending U.S. Appl. No. 11/391,505.
USPTO Notice of Allowance dated Oct. 7, 2008 for copending U.S. Appl. No. 11/390,908.
USPTO Office Action dated Oct. 14, 2008 for copending U.S. Appl. No. 11/390,811.
USPTO Office Action dated Oct. 22, 2008 for copending U.S. Appl. No. 11/390,750.
USPTO Office Action dated Oct. 22, 2008 for copending U.S. Appl. No. 11/390,865.
USPTO Office Action dated Oct. 14, 2008 for copending U.S. Appl. No. 11/390,654.
USPTO Office Action dated Oct. 20, 2008 for copending U.S. Appl. No. 11/390,836.
Copending U.S. Appl. No. 12/254,894, filed Oct. 21, 2008, Gary Michael Stack, et al.
Copending U.S. Appl. No. 12/390,694, filed Feb. 23, 2009, Gary Michael Stack.
USPTO Office Action dated Oct. 29, 2008 for copending U.S. Appl. No. 11/390,955.
USPTO Notice of Allowance dated Nov. 3, 2008 for copending U.S. Appl. No. 11/391,642.
USPTO Office Action dated Nov. 3, 2008 for copending U.S. Appl. No. 11/391,485.
USPTO Office Action dated Oct. 29, 2008 for copending U.S. Appl. No. 11/390,864.
USPTO Office Action dated Oct. 30, 2008 for copending U.S. Appl. No. 11/391,495.
USPTO Office Action dated Oct. 31, 2008 for copending U.S. Appl. No. 11/391,156.
USPTO Office Action dated Nov. 3, 2008 for copending U.S. Appl. No. 11/390,883.
USPTO Office Action dated Dec. 19, 2008 for copending U.S. Appl. No. 11/390,751.
USPTO Office Action dated Dec. 31, 2008 for copending U.S. Appl. No. 11/390,827.
USPTO Office Action dated Dec. 31, 2008 for copending U.S. Appl. No. 11/390,826.
USPTO Office Action dated Nov. 14, 2008 for copending U.S. Appl. No. 11/390,630.
USPTO Office Action dated Dec. 19, 2008 for copending U.S. Appl. No. 11/391,576.
USPTO Office Action dated Dec. 19, 2008 for copending U.S. Appl. No. 11/390,629.
USPTO Office Action dated Dec. 31, 2008 for copending U.S. Appl. No. 11/390,773.
USPTO Office Action dated Dec. 12, 2008 for copending U.S. Appl. No. 11/391,063.
USPTO Office Action dated Dec. 19, 2008 for copending U.S. Appl. No. 11/390,814.
USPTO Office Action dated Dec. 31, 2008 for copending U.S. Appl. No. 11/390,722.
USPTO Office Action dated Nov. 14, 2008 for copending U.S. Appl. No. 11/390,882.
USPTO Office Action dated Jan. 29, 2009 for copending U.S. Appl. No. 11/588,524.
USPTO Office Action dated Jan. 30, 2009 for copending U.S. Appl. No. 11/588,458.
USPTO Office Action dated Feb. 2, 2009 for copending U.S. Appl. No. 11/390,853.
USPTO Office Action dated Jan. 21, 2009 for copending U.S. Appl. No. 11/390,847.
USPTO Office Action dated Jan. 12, 2009 for copending U.S. Appl. No. 11/390,858.
USPTO Office Action dated Jan. 26, 2009 for copending U.S. Appl. No. 11/391,659.
USPTO Office Action dated Jan. 26, 2009 for copending U.S. Appl. No. 11/588,554.
USPTO Office Action dated Feb. 3, 2009 for copending U.S. Appl. No. 11/391,505.
USPTO Office Action dated Feb. 10, 2009 for copending U.S. Appl. No. 11/390,865.
USPTO Office Action dated Feb. 12, 2009 for copending U.S. Appl. No. 11/439,062.
USPTO Office Action dated Feb. 13, 2009 for copending U.S. Appl. No. 11/439,340.
USPTO Office Action dated Feb. 25, 2009 for copending U.S. Appl. No. 11/588,907.
USPTO Office Action dated Feb. 25, 2009 for copending U.S. Appl. No. 11/588,527.

(56) References Cited

OTHER PUBLICATIONS

USPTO Office Action dated Feb. 27, 2009 for copending U.S. Appl. No. 11/390,955.
USPTO Office Action dated Feb. 25, 2009 for copending U.S. Appl. No. 11/588,906.
USPTO Office Action dated Feb. 25, 2009 for copending U.S. Appl. No. 11/588,883.
USPTO Office Action dated Mar. 5, 2009 for copending U.S. Appl. No. 11/390,864.
USPTO Office Action dated Mar. 6, 2009 for copending U.S. Appl. No. 11/391,156.
USPTO Office Action dated Feb. 25, 2009 for copending U.S. Appl. No. 11/390,811.
USPTO Office Action dated Feb. 27, 2009 for copending U.S. Appl. No. 11/390,654.
USPTO Office Action dated Feb. 27, 2009 for copending U.S. Appl. No. 11/390,836.
USPTO Office Action dated Mar. 13, 2009 for copending U.S. Appl. No. 11/390,883.
USPTO Office Action dated Mar. 11, 2009 for copending U.S. Appl. No. 11/390,630.
USPTO Office Action dated Mar. 9, 2009 for copending U.S. Appl. No. 11/391,495.
USPTO Office Action dated Mar. 9, 2009 for copending U.S. Appl. No. 11/390,750.
USPTO Office Action dated Mar. 16, 2009 for copending U.S. Appl. No. 11/390,882.
USPTO Office Action dated Apr. 27, 2009 for copending U.S. Appl. No. 11/390,655.
USPTO Office Action dated Apr. 27, 2009 for copending U.S. Appl. No. 11/391,137.
USPTO Office Action dated Mar. 16, 2009 for copending U.S. Appl. No. 11/391,485.
USPTO Office Action dated Apr. 15, 2009 for copending U.S. Appl. No. 12/091,566.
USPTO Notice of Allowance dated Apr. 13, 2009 for copending U.S. Appl. No. 11/391,063.
USPTO Office Action dated Apr. 16, 2009 for copending U.S. Appl. No. 12/091,570.
USPTO Office Action dated Apr. 17, 2009 for copending U.S. Appl. No. 11/390,671.
USPTO Office Action dated Apr. 17, 2009 for copending U.S. Appl. No. 11/391,565.
USPTO Office Action dated Apr. 20, 2009 for copending U.S. Appl. No. 11/390,631.
USPTO Office Action dated Mar. 31, 2009 for copending U.S. Appl. No. 11/390,563.
USPTO Office Action dated Apr. 2, 2009 for copending U.S. Appl. No. 11/390,793.
USPTO Office Action dated Mar. 23, 2009 for copending U.S. Appl. No. 11/390,752.
USPTO Office Action dated Mar. 23, 2009 for copending U.S. Appl. No. 11/390,794.
USPTO Office Action dated May 13, 2009 for copending U.S. Appl. No. 12/361,779.
USPTO Office Action dated May 13, 2009 for copending U.S. Appl. No. 12/365,515.
USPTO Office Action dated May 21, 2009 for copending U.S. Appl. No. 11/706,476.
USPTO Office Action dated May 22, 2009 for copending U.S. Appl. No. 11/706,791.
USPTO Office Action dated May 18, 2009 for copending U.S. Appl. No. 11/391,505.
USPTO Office Action dated Apr. 14, 2009 for copending U.S. Appl. No. 11/635,434.
USPTO Office Action dated Apr. 14, 2009 for copending U.S. Appl. No. 11/635,433.
USPTO Office Action dated May 18, 2009 for copending U.S. Appl. No. 11/390,846.
USPTO Office Action dated Jun. 11, 2009 for copending U.S. Appl. No. 11/390,809.
USPTO Office Action dated Jul. 2, 2009 for copending U.S. Appl. No. 11/390,827.
USPTO Office Action dated Aug. 7, 2009 for copending U.S. Appl. No. 11/390,773.
USPTO Office Action dated Aug. 27, 2009 for copending U.S. Appl. No. 11/390,826.
USPTO Office Action dated Aug. 10, 2009 for copending U.S. Appl. No. 11/390,722.
Dixon, E.R. et al., "The Inter-Relation of Some Mechanical Properties with Molecular Weight and Crystallinity in Poly(ethylene terephthalate)", 1968, pp. 464-470, Journal of Materials Science, vol. 3.
USPTO Office Action dated Sep. 4, 2009, for copending U.S. Appl. No. 11/391,124.
USPTO Office Action dated Sep. 10, 2009, for copending U.S. Appl. No. 11/390,812.
New Copending U.S. Appl. No. 12/479,893, filed Jun. 8, 2009, Emmett Dudley Crawford, et al.
USPTO Office Action dated Sep. 14, 2009 for copending U.S. Appl. No. 11/391,576.
Ellis, Thomas S., "Miscibility of Polyamide Blends: Effects of Configuration," 1995, Polymer, vol. 36, Issue 20, pp. 3919-3926.
Buschow, K.H.J., et al., "Packaging: Papers for Sacks and Bags," 2001, Encyclopedia of Materials: Science and Technology, vol. 8, Elsevier, pp. 6646-6652.
Coles, Richard, et al., "Food Packaging Technology," 2003, pp. 194-195 and 224-229, Blackwell Publishing.
Sajiki, Junko, et al., "Leaching of Bisphenol A (BPA) to Seawater from Polycarbonate Plastic and its Degradation by Reactive Oxygen Species," 2003, Chemosphere, 51, pp. 55-62.
USPTO Office Action dated Oct. 2, 2009 for copending U.S. Appl. No. 11/588,524.
USPTO Office Action dated Oct. 7, 2009 for copending U.S. Appl. No. 11/588,458.
USPTO Office Action dated Sep. 29, 2009 for copending U.S. Appl. No. 11/390,751.
USPTO Office Action dated Sep. 24, 2009 for copending U.S. Appl. No. 11/588,883.
USPTO Office Action dated Sep. 28, 2009 for copending U.S. Appl. No. 11/390,847.
USPTO Office Action dated Sep. 24, 2009 for copending U.S. Appl. No. 11/390,858.
USPTO Office Action dated Sep. 29, 2009 for copending U.S. Appl. No. 11/390,629.
USPTO Office Action dated Sep. 29, 2009 for copending U.S. Appl. No. 11/390,814.
USPTO Office Action dated Oct. 19, 2009 for copending U.S. Appl. No. 11/390,563.
USPTO Office Action dated Oct. 21, 2009 for U.S. Appl. No. 11/391,156.
Gupta, V.B. et al., "PET Fibers, Films, and Bottles: Section 5-7", Handbook of Thermoplastic Polyesters: Homopolymers, Copolymers, Blends, and Composites, 2005, pp. 362-388, Wiley InterScience.
USPTO Office Action dated Oct. 22, 2009 for copending U.S. Appl. No. 11/588,906.
USPTO Office Action dated Nov. 3, 2009 for copending U.S. Appl. No. 11/390,883.
USPTO Office Action dated Nov. 4, 2009 for copending U.S. Appl. No. 11/390,750.
USPTO Office Action dated Nov. 4, 2009 for copending U.S. Appl. No. 11/390,864.
USPTO Office Action dated Nov. 17, 2009 for copending U.S. Appl. No. 12/254,894.
USPTO Office Action dated Nov. 18, 2009 for copending U.S. Appl. No. 11/390,630.
USPTO Office Action dated Nov. 30, 2009 for copending U.S. Appl. No. 11/391,495.
Turner, S.R., et al., "Amorphous and Crystalline Polyesters based on 1,4-Cyclohexanedimethanol", Chapter 7, Modern Polyesters: Chem-

(56) References Cited

OTHER PUBLICATIONS istry and Technology of Polyesters and Copolyesters, Edited by J. Sheirs and T.E. Long, 2003 John Wiley & Sons, Ltd., pp. 267-292.
USPTO Office Action dated Nov. 18, 2009 for copending U.S. Appl. No. 11/390,794.
USPTO Office Action dated Nov. 20, 2009 for copending U.S. Appl. No. 11/391,485.
USPTO Office Action dated Nov. 20, 2009 for copending U.S. Appl. No. 11/390,882.
USPTO Office Action dated Dec. 1, 2009 for copending U.S. Appl. No. 12/091,570.
USPTO Office Action dated Dec. 3, 2009 for copending U.S. Appl. No. 11/395,505.
USPTO Office Action dated Dec. 4, 2009 for copending U.S. Appl. No. 12/091,566.
Zipper, Marcus D.,et al., "A Free Volume Study of Miscible Polyester Blends," 1995, pp. 127-136, Polymer International, vol. 36.
"APEC High-Heat Polycarbonate Resin," 2004, Bayer Material Science Product Information *Not Prior Art; Submitted for State of the Art*.
Lobo, Hubert et al, "Handbook of Plastics Analysis," 2003, pp. 20 and 21, Marcel Dekker, Inc.
Turner, S.R., et al. "Amorphous and Crystalline Polyesters based on 1,4-Cyclohexanedimethanol," 2003, *Modern Polyesters: Chemistry and Technology of Polyesters and Copolyesters*, pp. 268, 284-285, J. Sheirs and T.E. Long, ed., John Wiley and Sons, Ltd.
USPTO Notice of Allowance dated Dec. 11, 2009 for copending U.S. Appl. No. 12/365,515.
USPTO Office Action dated Dec. 18, 2009 for copending U.S. Appl. No. 11/390,846.
Copending U.S. Appl. No. 12/639,324, filed Dec. 16, 2009.
USPTO Notice of Allowance dated Dec. 22, 2009 for copending U.S. Appl. No. 12/361,779.
USPTO Office Action dated Jan. 7, 2010 for copending U.S. Appl. No. 12/091,568.
USPTO Office Action dated Jan. 13, 2010 for copending U.S. Appl. No. 11/635,433.
USPTO Office Action dated Jan. 14, 2010 for copending U.S. Appl. No. 11/390,809.
USPTO Notice of Allowance dated Jan. 27, 2010 for copending U.S. Appl. No. 11/635,434.
USPTO Office Action dated Mar. 11, 2010, for copending U.S. Appl. No. 11/391,812.
Copending U.S. Appl. No. 12/724,492, filed Mar. 16, 2010.
Copending U.S. Appl. No. 12/724,480, filed Mar. 16, 2010.
Copending U.S. Appl. No. 12/724,468, filed Mar. 16, 2010.
USPTO Office Action dated Mar. 19, 2010, for copending U.S. Appl. No. 11/588,527.
USPTO Notice of Allowance dated Mar. 24, 2010 for copending U.S. Appl. No. 11/391,565.
USPTO Office Action dated Mar. 29, 2010 for copending U.S. Appl. No. 11/390,812.
USPTO Notice of Allowance dated Apr. 15, 2010 for copending U.S. Appl. No. 11/391,505.
USPTO Office Action dated Apr. 19, 2010 for copending U.S. Appl. No. 12/724,480.
USPTO Office Action dated Apr. 21, 2010 for copending U.S. Appl. No. 12/724,468.
USPTO Office Action dated Apr. 21, 2010 for copending U.S. Appl. No. 12/724,492.
USPTO Office Action dated May 6, 2010 for copending U.S. Appl. No. 12/254,894.
New copending U.S. Appl. No. 12/784,193, filed May 20, 2010, Emmett Dudley Crawford, et al.
USPTO Notice of Allowance dated May 13, 2010 for copending U.S. Appl. No. 11/390,629.
USPTO Notice of Allowance dated May 13, 2010 for copending U.S. Appl. No. 11/390,751.
USPTO Notice of Allowance dated May 21, 2010 for copending U.S. Appl. No. 11/391,156.
USPTO Notice of Allowance dated May 26, 2010 for copending U.S. Appl. No. 11/391,495.
USPTO Notice of Allowance dated Jun. 24, 2010 for copending U.S. Appl. No. 11/391,576.
USPTO Office Action dated Jun. 24, 2010 for copending U.S. Appl. No. 11/390,846.
USPTO Office Action dated Jul. 8, 2010 for copending U.S. Appl. No. 11/390,809.
USPTO Notice of Allowance dated Jul. 8, 2010 for copending U.S. Appl. No. 11/390,630.
USPTO Notice of Allowance dated Jul. 8, 2010 for copending U.S. Appl. No. 11/390,883.
USPTO Office Action dated Jul. 12, 2010 for copending U.S. Appl. No. 11/390,794.
Notice of Allowance dated Jul. 13, 2010 for copending U.S. Appl. No. 11/391,505.
USPTO Office Action dated Jul. 22, 2010 for copending U.S. Appl. No. 12/479,893.
USPTO Notice of Allowance dated Jul. 22, 2010 for copending U.S. Appl. No. 11/391,485.
USPTO Notice of Allowance dated Aug. 3, 2010 for copending U.S. Appl. No. 11/390,864.
New copending U.S. Appl. No. 12/853,717 filed Aug. 10, 2010, Emmett Dudley Crawford, et al.
USPTO Notice of Allowance dated Aug. 11, 2010 for copending U.S. Appl. No. 11/390,631.
USPTO Notice of Allowance dated Sep. 2, 2010 for copending U.S. Appl. No. 11/390,811.
USPTO Office Action dated Sep. 2, 2010 for copending U.S. Appl. No. 11/391,124.
New copending U.S. Appl. No. 12/888,648, filed Sep. 23, 2010, Thomas Joseph Pecorini et al.
USPTO Office Action dated Oct. 5, 2010 for copending U.S. Appl. No. 11/390,655.
New copending U.S. Appl. No. 12/900,060, filed Oct. 7, 2010, Thomas Joseph Pecorini, et al.
USPTO Office Action dated Oct. 8, 2010 for copending U.S. Appl. No. 11/390,812.
USPTO Notice of Allowance dated Oct. 28, 2010 for copending U.S. Appl. No. 11/390,827.
USPTO Office Action dated Oct. 27, 2010 for copending U.S. Appl. No. 12/294,690.
New Copending U.S. Appl. No. 12/900,060, filed Oct. 7, 2010, Joseph Thomas Pecorini.
USPTO Notice of Allowance dated Oct. 14, 2010 for copending U.S. Appl. No. 11/390,722.
USPTO Notice of Allowance dated Nov. 2, 2010 for copending U.S. Appl. No. 12/724,480.
USPTO Notice of Allowance dated Nov. 4, 2010 for copending U.S. Appl. No. 12/724,468.
USPTO Notice of Allowance dated Nov. 4, 2010 for copending U.S. Appl. No. 11/390,955.
USPTO Office Action dated Nov. 4, 2010 for copending U.S. Appl. No. 12/294,686.
USPTO Notice of Allowance dated Nov. 4, 2010 for copending U.S. Appl. No. 11/390,826.
USPTO Office Action dated Oct. 27, 2010 for copending U.S. Appl. No. 11/390,836.
USPTO Notice of Allowance dated Nov. 23, 2010 for copending U.S. Appl. No. 11/390,563.
New copending U.S. Appl. No. 12/943,217, filed Nov. 10, 2010, Emmett Dudley Crawford et al.
New copending U.S. Appl. No. 13/007,838, filed Jan. 17, 2011, Emmett Dudley Crawford et al.
New copending U.S. Appl. No. 13/016,147, filed Jan. 28, 2011, Emmett Dudley Crawford, et al.
New copending U.S. Appl. No. 13/017,069, filed Jan. 31, 2011, Emmett Dudley Crawford, et al.
New Copending U.S. Appl. No. 13/017,352, filed Jan. 31, 2011, Emmett Dudley Crawford, et al.
USPTO Office Action dated Jan. 25, 2011 for copending U.S. Appl. No. 12/853,717.

(56) References Cited

OTHER PUBLICATIONS

Al-Malaika, S., "Stabilization", Encyclopedia of Polymer Science and Technology, vol. 4, 2001, pp. 179-229, John Wiley & Sons, Inc.
USPTO Notice of Allowance dated Jan. 26, 2011 for copending U.S. Appl. No. 11/390,858.
USPTO Office Action dated Feb. 2, 2011 for copending U.S. Appl. No. 11/390,655.
USPTO Office Action dated Mar. 17, 2011 for copending U.S. Appl. No. 12/479,893.
USPTO Notice of Allowance dated Mar. 17, 2011 for copending U.S. Appl. No. 11/391,137.
USPTO Office Action dated Feb. 14, 2011 for copending U.S. Appl. No. 12/294,690.
USPTO Notice of Allowance dated Feb. 18, 2011 for copending U.S. Appl. No. 11/390,809.
USPTO Notice of Allowance dated Feb. 17, 2011 for copending U.S. Appl. No. 11/390,812.
Notice of Allowance and Fee(s) Due mailing date Jul. 18, 2012 received in co-pending U.S. Appl. No. 13/348,677.
Notice of Allowance and Fee(s) Due mailing date Jun. 21, 2012 received in co-pending U.S. Appl. No. 12/091,570.
Notice of Allowance and Fee(s) Due mailing date Jun. 11, 2012 received in co-pending U.S. Appl. No. 12/274,692.
Office Action notification date May 21, 2012 received in co-pending U.S. Appl. No. 13/215,511.
USPTO Notice of Allowance dated Aug. 12, 2011 for copending U.S. Appl. No. 11/390,752.
USPTO Office Action dated Jul. 19, 2011 for copending U.S. Appl. No. 11/390,794.
USPTO Notice of Allowance dated Aug. 3, 2011 for copending U.S. Appl. No. 11/390,655.
New copending U.S. Appl. No. 13/162,870, filed Jun. 17, 2011, Emmett Dudley Crawford, et al.
USPTO Office Action dated Jul. 7, 2011 for copending U.S. Appl. No. 11/588,906.
USPTO Office Action dated Jun. 22, 2011 for copending U.S. Appl. No. 12/091,570.
USPTO Office Action dated Jun. 8, 2011 for copending U.S. Appl. No. 11/588,883.
USPTO Notice of Allowance dated Jul. 21, 2011 for copending U.S. Appl. No. 11/390,671.
New copending U.S. Appl. No. 13/215,511, filed Aug. 23, 2011, Emmett Dudley Crawford, et al.
USPTO Office Action dated Aug. 17, 2011 for copending U.S. Appl. No. 12/274,692.
USPTO Office Action dated Sep. 14, 2011 for copending U.S. Appl. No. 13/017,069.
USPTO Supplemental Notice of Allowability dated Sep. 16, 2011 for copending U.S. Appl. No. 11/390,671.
USPTO Notice of Allowance dated Sep. 16, 2011 for copending U.S. Appl. No. 12/784,193.
USPTO Notice of Allowance dated Mar. 8, 2012 for copending U.S. Appl. No. 12/274,692.
USPTO Notice of Allowance dated Feb. 14, 2012 for copending U.S. Appl. No. 11/588,906.
New copending U.S. Appl. No. 13/348,677, filed Jan. 12, 2012, Emmett Dudley Crawford et al.
New copending U.S. Appl. No. 13/398,262, filed Feb. 16, 2012, Emmett Dudley Crawford et al.
USPTO Notice of Allowance dated Mar. 21, 2012 for copending U.S. Appl. No. 12/390,694.
New co-pending U.S. Appl. No. 13/596,754, filed Aug. 28, 2012, Thomas Joseph Pecorini et al.
New co-pending U.S. Appl. No. 13/596,805, filed Aug. 28, 2012, Ted Calvin Germroth et al.
Notice of Allowance received in co-pending U.S. Appl. No. 13/016,147 received on Sep. 28, 2012.
USPTO Non-Final Office Action received in co-pending U.S. Appl. No. 13/596,754 received Oct. 2, 2012.
USPTO Non-Final Office Action received in co-pending U.S. Appl. No. 13/162,870 received Oct. 18, 2012.
New co-pending U.S. Appl. No. 13/658,249, filed Oct. 23, 2012, Emmett Dudley Crawford et al.
USPTO Office Action dated Dec. 7, 2012 for co-pending U.S. Appl. No. 13/398,262.
Notice of Allowance and Fee(s) Due mailing date Nov. 23, 2012 received in co-pending U.S. Appl. No. 13/348,677.
Notice of Allowance and Fee(s) Due mailing date Jan. 24, 2013 received in co-pending U.S. Appl. No. 13/215,511.
USPTO Notice of Allowance dated Apr. 1, 2013 for co-pending U.S. Appl. No. 13/215,511.
USPTO Notice of Allowance dated Apr. 3, 2013 for co-pending U.S. Appl. No. 12/888,648.
USPTO Notice of Allowance dated Apr. 4, 2013 for co-pending U.S. Appl. No. 13/596,754.
USPTO Notice of Allowance dated Apr. 12, 2013 for co-pending U.S. Appl. No. 13/215,511.
Co-pending application, U.S. Appl. No. 13/941,362, filed on Jul 12, 2013, Emmett Crawford et al.
Non-Final Office Action notification date Oct. 25, 2013 received in co-pending U.S. Appl. No. 13/007,838.
USPTO Notice of Allowance dated May 12, 2014 for co-pending U.S. Appl. No. 13/596,805.
USPTO Office Action dated Aug. 21, 2014 for co-pending U.S. Appl. No. 13/398,262.
Color Index Constitution No. 515240, SciFinder, Nov. 6, 2006.
Color Index Constitution No. 515245, SciFinder, Nov. 6, 2006.
USPTO Office Action dated Dec. 10, 2014 for co-pending U.S. Appl. No. 13/658,249.
Notice of Allowance notification date Dec. 12, 2014 received in co-pending US. Appl. No. 13/776,038.
USPTO Notice of Allowance dated Jan. 28, 2015 for copending U.S. Appl. No. 13/007,838.
USPTO Notice of Allowance dated Mar. 5, 2015 for copending U.S. Appl. No. 13/776,038.
USPTO Notice of Allowance dated Mar. 19, 2015 for copending U.S. Appl. No. 13/709,097.
USPTO Notice of Allowance dated Apr. 6, 2015 for copending U.S. Appl. No. 13/007,838.
USPTO Office Action dated Apr. 8, 2015 for copending U.S. Appl. No. 13/658,249.
USPTO Notice of Allowance dated Apr. 10, 2015 for copending U.S. Appl. No. 13/596,805.
USPTO Office Action dated Apr. 30, 2015 for copending U.S. Appl. No. 13/941,362.
USPTO Notice of Allowance dated Jun. 22, 2015 for copending U.S. Appl. No. 13/776,038.
USPTO Notice of Allowance dated Jul. 6, 2015 for copending U.S. Appl. No. 13/709,097.
USPTO Office Action dated Jul. 28, 2015 for copending U.S. Appl. No. 13/658,249.
USPTO Notice of Allowance dated Jul. 31, 2015 for copending U.S. Appl. No. 13/596,805.
USPTO Notice of Allowance dated Aug. 21, 2015 for copending U.S. Appl. No. 13/007,838.
USPTO Notice of Allowance dated Sep. 1, 2015 for copending U.S. Appl. No. 13/776,038.
USPTO Notice of Allowance dated Sep. 3, 2015 for copending U.S. Appl. No. 13/709,097.
USPTO Notice of Allowance dated Sep. 16, 2015 for copending U.S. Appl. No. 13/596,805.

POLYESTER COMPOSITIONS WHICH COMPRISE CYCLOBUTANEDIOL HAVING CERTAIN CIS/TRANS RATIOS

CROSS-REFERENCES TO RELATED APPLICATIONS

This application is a continuation of U.S. patent application Ser. No. 11/391,137 filed Mar. 28, 2006 which claims priority under 35 U.S.C. §119(e) to U.S. Provisional Application Ser. No. 60/691,567 filed on Jun. 17, 2005; U.S. Provisional Application Ser. No. 60/731,454 filed on Oct. 28, 2005; U.S. Provisional Application Ser. No. 60/731,389, filed on Oct. 28, 2005; U.S. Provisional Application Ser. No. 60/739,058, filed on Nov. 22, 2005; and U.S. Provisional Application Ser. No. 60/738,869, filed on Nov. 22, 2005; U.S. Provisional Application Ser. No. 60/750,692 filed on Dec. 15, 2005; U.S. Provisional Application Ser. No. 60/750,693, filed on Dec. 15, 2005; U.S. Provisional Application Ser. No. 60/750,682, filed on Dec. 15, 2005; and U.S. Provisional Application Ser. No. 60/750,547, filed on Dec. 15, 2005; all of which are hereby incorporated by this reference in their entireties.

FIELD OF THE INVENTION

The present invention generally relates to polyester compositions comprising a polyesters made from terephthalic acid, or an ester thereof, or mixtures thereof, 2,2,4,4-tetramethyl-1,3-cyclobutanediol, and 1,4-cyclohexanedimethanol, having a certain ratio of cis/trans 2,2,4,4-tetramethyl-1,3-cyclobutanediol. These polyester compositions are believed to have a unique combination of at least one of high impact strengths, high glass transition temperature ($T_g$), toughness, certain inherent viscosities, low ductile-to-brittle transition temperatures, good color and clarity, low densities, chemical resistance, hydrolytic stability, and long crystallization half-times, which allow them to be easily formed into articles.

BACKGROUND OF THE INVENTION

Poly(1,4-cyclohexylenedimethylene) terephthalate (PCT), a polyester based solely on terephthalic acid or an ester thereof and 1,4-cyclohexanedimethanol, is known in the art and is commercially available. This polyester crystallizes rapidly upon cooling from the melt, making it very difficult to form amorphous articles by methods known in the art such as extrusion, injection molding, and the like. In order to slow down the crystallization rate of PCT, copolyesters can be prepared containing additional dicarboxylic acids or glycols such as isophthalic acid or ethylene glycol. These ethylene glycol- or isophthalic acid-modified PCTs are also known in the art and are commercially available.

One common copolyester used to produce films, sheeting, and molded articles is made from terephthalic acid, 1,4-cyclohexanedimethanol, and ethylene glycol. While these copolyesters are useful in many end-use applications, they exhibit deficiencies in properties such as glass transition temperature and impact strength when sufficient modifying ethylene glycol is included in the formulation to provide for long crystallization half-times. For example, copolyesters made from terephthalic acid, 1,4-cyclohexanedimethanol, and ethylene glycol with sufficiently long crystallization half-times can provide amorphous products that exhibit what is believed to be undesirably higher ductile-to-brittle transition temperatures and lower glass transition temperatures than the compositions revealed herein.

The polycarbonate of 4,4'-isopropylidenediphenol (bisphenol A polycarbonate) has been used as an alternative for polyesters known in the art and is a well known engineering molding plastic. Bisphenol A polycarbonate is a clear, high-performance plastic having good physical properties such as dimensional stability, high heat resistance, and good impact strength. Although bisphenol-A polycarbonate has many good physical properties, its relatively high melt viscosity leads to poor melt processability and the polycarbonate exhibits poor chemical resistance. It is also difficult to thermoform.

Polymers containing 2,2,4,4-tetramethyl-1,3-cyclobutanediol have also been generally described in the art. Generally, however, these polymers exhibit high inherent viscosities, high melt viscosities and/or high Tgs (glass transition temperatures) such that the equipment used in industry can be insufficient to manufacture or post polymerization process these materials.

Thus, there is a need in the art for polyester compositions comprising at least one polymer having a combination of two or more properties, chosen from at least one of the following: toughness, high glass transition temperatures, high impact strength, hydrolytic stability, chemical resistance, long crystallization half-times, low ductile to brittle transition temperatures, good color, and clarity, lower density and/or thermoformability of polyesters while retaining processability on the standard equipment used in the industry.

SUMMARY OF THE INVENTION

It is believed that certain polyester compositions formed from terephthalic acid, an ester thereof, or mixtures thereof, 1,4-cyclohexanedimethanol and certain cis/trans molar ratios of 2,2,4,4-tetramethyl-1,3-cyclobutanediol with certain monomer compositions, inherent viscosities and/or glass transition temperatures are superior to polyesters known in the art and to polycarbonate with respect to one or more of high impact strengths, hydrolytic stability, toughness, chemical resistance, good color and clarity, long crystallization half-times, low ductile to brittle transition temperatures, lower specific gravity, and thermoformability. These compositions are believed to be similar to polycarbonate in heat resistance and are still processable on the standard industry equipment.

In one aspect, the invention relates to at least one polyester composition comprising at least one polyester which comprises:

(a) a dicarboxylic acid component comprising:
- i) 70 to 100 mole % of terephthalic acid residues;
- ii) 0 to 30 mole % of aromatic dicarboxylic acid residues having up to 20 carbon atoms; and
- iii) 0 to 10 mole % of aliphatic dicarboxylic acid residues having up to 16 carbon atoms; and (b) a glycol component comprising:
- i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
- ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.10 to 1.2 dL/g as determined in 60/40 (wt/wt) phenol/tetrachloroethane at a concentration of 0.5 g/100 ml at 25° C.; and wherein the polyester has a Tg of from 85 to 200° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 ii) 1 to 99 mole % of 1,4-cyclohexanedimethanol residues,
(c) residues from at least one branching agent;

wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt)phenol/tetrachloroethane at a concentration of 0.5 g/100 ml at 25° C.; and wherein the polyester has a Tg of 85 to 200° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 1 to 80 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 ii) 20 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of 85° C. to 200° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 40 to 80 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 ii) 20 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 125 to 200° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 ii) 35 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 85 to 200° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 40 to 55 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 ii) 45 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; wherein the polyester has a Tg of 85 to 200° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 40 to 50 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 50 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; wherein the polyester has a Tg of 85 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 45 to 55 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 45 to 55 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; wherein the polyester has a Tg of 85 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) greater than 50 up to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to less than 50 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 85 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) greater than 50 up to 80 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 20 to less than 50 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 85° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) greater than 51 up to 80 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 20 to less than 49 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 85° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, (c) residues of at least one branching agent;

wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt)phenol/tetrachloroethane at a concentration of 0.5 g/100 ml at 25° C.; and wherein the polyester has a Tg of 110 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) greater than 50 up to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to less than 50 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 110° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) greater than 51 up to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to less than 49 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 110° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) greater than 50 up to 80 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 20 to less than 50 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 110° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) greater than 51 up to 80 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 20 to less than 49 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 110° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 0.75 dL/g as determined in 60/40 (wt/wt) phenol/tetrachloroethane at a concentration of 0.5 g/100 ml at 25° C.; and wherein the polyester has a Tg of from 110 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 80 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 20 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 0.75 dL/g as determined in 60/40 (wt/wt) phenol/tetrachloroethane at a concentration of 0.5 g/100 ml at 25° C.; and wherein the polyester has a Tg of 110 to 200° C.

In one aspect, this invention relates to a polyester composition comprising at least one polyester which comprises:

(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
  ii) 35 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 0.75 dL/g as determined in 60/40 (wt/wt) phenol/tetrachloroethane at a concentration of 0.5 g/100 ml at 25° C.; and wherein the polyester has a Tg of 110 to 200° C.

In one aspect, this invention relates to a polyester composition comprising at least one polyester which comprises:

(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 40 to 55 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
  ii) 45 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 0.75 dL/g as determined in 60/40 (wt/wt) phenol/tetrachloroethane at a concentration of 0.5 g/100 ml at 25° C.; wherein the polyester has a Tg of 110 to 200° C.

In one aspect, this invention relates to a polyester composition comprising at least one polyester which comprises:

(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 40 to 50 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
  ii) 50 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 0.75 dL/g as determined in 60/40 (wt/wt) phenol/tetrachloroethane at a concentration of 0.5 g/100 ml at 25° C.; wherein the polyester has a Tg of 110 to 200° C.

In one aspect, this invention relates to a polyester composition comprising at least one polyester which comprises:

(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 45 to 55 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
  ii) 45 to 55 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 0.75 dL/g as determined in 60/40 (wt/wt) phenol/tetrachloroethane at a concentration of 0.5 g/100 ml at 25° C.; wherein the polyester has a Tg of 110 to 200° C.

In one aspect, this invention relates to a polyester composition comprising at least one polyester which comprises:

(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 40 to 80 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
  ii) 20 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 0.75 dL/g as determined in 60/40 (wt/wt) phenol/tetrachloroethane at a concentration of 0.5 g/100 ml at 25° C.; and wherein the polyester has a Tg of 110 to 200° C.

In one aspect, this invention relates to a polyester composition comprising at least one polyester which comprises:

(a) a dicarboxylic acid component comprising:
  i) 70 to 100 mole % of terephthalic acid residues;
  ii) 0 to 30 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 and less than 0.70 dL/g as determined in 60/40 (wt/wt) phenol/tetrachloroethane at a concentration of 0.5 g/100 ml at 25° C.; and wherein the polyester has a Tg of from 110 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is greater than 0.76 up to 1.2 dL/g as determined in 60/40 (wt/wt) phenol/tetrachloroethane at a concentration of 0.5 g/100 ml at 25° C.; and wherein the polyester has a Tg of from 110° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 110 to 150° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 0.75 dL/g as determined in 60/40 (wt/wt) phenol/tetrachloroethane at a concentration of 0.5 g/100 ml at 25° C.; and wherein the polyester has a Tg of 110 to 150° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 120 to 135° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.35 to 0.75 dL/g as determined in 60/40 (wt/wt) phenol/tetrachloroethane at a concentration of 0.5 g/100 ml at 25° C.; and wherein the polyester has a Tg of 120 to 135° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 127° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 80 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 20 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of 127° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from greater than 148° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from greater than 148° C. to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 64.8? mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35.1 to 60 mole % of 1,4-cyclohexanedimethanol residues, iii) 0.10 to less than 15 mole % ethylene glycol residues;

wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; wherein the polyester has a Tg of 85 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.;

wherein the polyester has a Tg of 85 to 200° C. and optionally, wherein one or more branching agents is added prior to or during the polymerization of the polymer.

In one aspect, this invention relates to a polyester composition comprising:

(I) at least one polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues; and (II) at least one thermal stabilizer and/or reaction products thereof;

wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt)phenol/tetrachloroethane at a concentration of 0.5 g/100 ml at 25° C.;

wherein the polyester has a Tg of 85 to 200° C.

In one aspect, this invention relates to a polyester composition comprising:

(I) at least one polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues; and (II) at least one thermal stabilizer and/or reaction products thereof;

wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt)phenol/tetrachloroethane at a concentration of 0.5 g/100 ml at 25° C.;

wherein the polyester has a Tg of 85 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 64.9 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 59.9 mole % of 1,4-cyclohexanedimethanol residues, iii) 0.10 to less than 15 mole % ethylene glycol residues;

wherein the total mole % of the dicarboxylic acid component is 100 mole %, and the total mole % of the glycol component is 100 mole %; and wherein the inherent viscosity of the polyester is from 0.35 to 0.75 dL/g or less as determined in 60/40 (wt/wt) phenol/tetrachloroethane at a concentration of 0.5 g/100 ml at 25° C.;

wherein the polyester has a Tg of 110 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues; and wherein the total mole % of the dicarboxylic acid component is 100 mole %, and the total mole % of the glycol component is 100 mole %; and wherein the inherent viscosity of the polyester is 0.35 to 0.75 dL/g as determined in 60/40 (wt/wt) phenol/tetrachloroethane at a concentration of 0.5 g/100 ml at 25° C.;

wherein the polyester has a Tg of 110 to 200° C. and optionally, wherein one or more branching agents is added prior to or during the polymerization of the polymer.

In one aspect, this invention relates to a polyester composition comprising:

(I) at least one polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues;

(II) at least one thermal stabilizer and/or reaction products thereof;

wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt)phenol/tetrachloroethane at a concentration of 0.5 g/100 ml at 25° C.;

wherein the polyester has a Tg of 110 to 200° C.

In one aspect, this invention relates to a polyester composition comprising:

(I) at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues; and (II) at least one thermal stabilizer and/or reaction products thereof;

wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt)phenol/tetrachloroethane at a concentration of 0.5 g/100 ml at 25° C.;

wherein the polyester has a Tg of 110 to 200° C.

In one aspect, this invention relates to a polyester composition comprising:

(I) at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 64.8 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35.1 to 60 mole % of 1,4-cyclohexanedimethanol residues, iii) 0.10 to less than 15 mole % ethylene glycol residues;

wherein the total mole % of the dicarboxylic acid component is 100 mole %, and the total mole % of the glycol component is 100 mole %; and wherein the inherent viscosity of the polyester is from 0.35 to 0.75 dL/g or less as determined in 60/40 (wt/wt) phenol/tetrachloroethane at a concentration of 0.5 g/100 ml at 25° C.;

wherein the polyester has a Tg of 110 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 0.75 dL/g as determined in 60/40 (wt/wt) phenol/tetrachloroethane at a concentration of 0.5 g/100 ml at 25° C.;

wherein the polyester has a Tg of 110 to 200° C. and optionally, wherein one or more branching agents is added prior to or during the polymerization of the polymer.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, (c) residues of at least one branching agent;

wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt)phenol/tetrachloroethane at a concentration of 0.5 g/100 ml at 25° C.; and wherein the polyester has a Tg of 110 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues; and (II) at least thermal stabilizer and/or reaction products thereof;

wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt)phenol/tetrachloroethane at a concentration of 0.5 g/100 ml at 25° C.;

wherein the polyester has a Tg of 110 to 200° C.

In one aspect, this invention relates to a polyester composition comprising:

(I) at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 40 to 65 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 35 to 60 mole % of 1,4-cyclohexanedimethanol residues; and (II) at least one thermal stabilizer and/or reaction products thereof;

wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt)phenol/tetrachloroethane at a concentration of 0.5 g/100 ml at 25° C.;

wherein the polyester has a Tg of 110 to 200° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) greater than 40 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to less than 60 mole % of 1,4-cyclohexanedimethanol residues;

wherein the total mole % of the dicarboxylic acid component is 100 mole %, and the total mole % of the glycol component is 100 mole %; and wherein the inherent viscosity of the polyester is from 0.10 to 1.2 dL/g as determined in 60/40 (wt/wt) phenol/tetrachloroethane at a concentration of 0.5 g/100 ml at 25° C.; wherein the polyester has a Tg of 85 to 200° C.; wherein the polyester is amorphous; wherein if ethylene glycol residues is present in the glycol component, it is present in the amount of 0.01 to less than 15 mole %.

In one aspect, this invention relates to a polyester composition comprising an amorphous polyester comprising:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 10 to 100 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 0 to 90 mole % of 1,4-cyclohexanedimethanol residues, wherein the total mole % of the dicarboxylic acid component is 100 mole %, and the total mole % of the glycol component is 100 mole %.

In one aspect, this invention relates to an amorphous polyester composition comprising:

(a) a dicarboxylic acid component comprising:

i) 90 to 100 mole % of terephthalic acid residues;

ii) up to 10 mole % of aromatic dicarboxylic acid residues having up to 20 carbon atoms; and iii) up to 10 mole % of aliphatic dicarboxylic acid residues having up to 16 carbon atoms; and (b) a glycol component comprising:

i) from 25 to 100 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) up to 75 mole % of 1,4-cyclohexanedimethanol residues, wherein the total mole % of the dicarboxylic acid component is 100 mole %, and the total mole % of the glycol component is 100 mole %; and wherein the amorphous polyester has a glass transition temperature ($T_g$) of greater than 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.10 to less than 1 dL/g as determined in 60/40 (wt/wt) phenol/tetrachloroethane at a concentration of 0.5 g/100 ml at 25° C.; and wherein the polyester has a Tg of from 85 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 85 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to 1.2 dL/g as determined in 60/40 (wt/wt) phenol/tetrachloroethane at a concentration of 0.5 g/100 ml at 25° C.; and wherein the polyester has a Tg of from 95° C. to 115° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 1 to 99 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 1 to 99 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is 0.35 to less than 1 dL/g as determined in 60/40 (wt/wt) phenol/tetrachloroethane at a concentration of 0.5 g/100 ml at 25° C.; and wherein the polyester has a Tg of from 95° C. to 115° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 5 to less than 50 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) greater than 50 to 95 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to 1.2 dL/g as determined in 60/40 (wt/wt) phenol/tetrachloroethane at a concentration of 0.5 g/100 ml at 25° C.; and wherein the polyester has a Tg of 85 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 10 to 30 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 70 to 90 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to 1.2 dL/g as determined in 60/40 (wt/wt) phenol/tetrachloroethane at a concentration of 0.5 g/100 ml at 25° C.; and wherein the polyester has a Tg of 85 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 14 to 25 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 76 to 85 mole % of 1,4-cyclohexanedimethanol residues, wherein the total mole % of the dicarboxylic acid component is 100 mole %, and the total mole % of the glycol component is 100 mole %; and wherein the inherent viscosity is from 0.50 to 1.2 dL/g as determined in 60/40 (wt/wt) phenol/tetrachloroethane at a concentration of 0.5 g/100 ml at 25° C.; and wherein the polyester has a Tg of 85 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 5 to less than 50 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) greater than 50 to 95 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to 1.2 dL/g as determined in 60/40 (wt/wt) phenol/tetrachloroethane at a concentration of 0.5 g/100 ml at 25° C.; and wherein the polyester has a Tg of 95 to 115° C.

In one aspect, this invention relates to a polyester composition comprising at least one polyester which comprises:

(a) a dicarboxylic acid component comprising:
- i) 70 to 100 mole % of terephthalic acid residues;
- ii) 0 to 30 mole % of aromatic dicarboxylic acid residues having up to 20 carbon atoms; and
- iii) 0 to 10 mole % of aliphatic dicarboxylic acid residues having up to 16 carbon atoms; and (b) a glycol component comprising:
- i) 10 to 30 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
- ii) 70 to 90 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to 1.2 dL/g as determined in 60/40 (wt/wt) phenol/tetrachloroethane at a concentration of 0.5 g/100 ml at 25° C.; and wherein the polyester has a Tg of 95 to 115° C.

In one aspect, this invention relates to a polyester composition comprising at least one polyester which comprises:

(a) a dicarboxylic acid component comprising:
- i) 70 to 100 mole % of terephthalic acid residues;
- ii) 0 to 30 mole % of aromatic dicarboxylic acid residues having up to 20 carbon atoms; and
- iii) 0 to 10 mole % of aliphatic dicarboxylic acid residues having up to 16 carbon atoms; and (b) a glycol component comprising:
- i) 14 to 25 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
- ii) 75 to 86 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to 1.2 dL/g as determined in 60/40 (wt/wt) phenol/tetrachloroethane at a concentration of 0.5 g/100 ml at 25° C.; and wherein the polyester has a Tg of 95 to 115° C.

In one aspect, this invention relates to a polyester composition comprising at least one polyester which comprises:

(a) a dicarboxylic acid component comprising:
- i) 70 to 100 mole % of terephthalic acid residues;
- ii) 0 to 30 mole % of aromatic dicarboxylic acid residues having up to 20 carbon atoms; and
- iii) 0 to 10 mole % of aliphatic dicarboxylic acid residues having up to 16 carbon atoms; and (b) a glycol component comprising:
- i) 5 to less than 50 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
- ii) greater than 50 to 95 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to less than 0.75 dL/g as determined in 60/40 (wt/wt) phenol/tetrachloroethane at a concentration of 0.5 g/100 ml at 25° C.; and wherein the polyester has a Tg of 85 to 120° C.

In one aspect, this invention relates to a polyester composition comprising at least one polyester which comprises:

(a) a dicarboxylic acid component comprising:
- i) 70 to 100 mole % of terephthalic acid residues;
- ii) 0 to 30 mole % of aromatic dicarboxylic acid residues having up to 20 carbon atoms; and
- iii) 0 to 10 mole % of aliphatic dicarboxylic acid residues having up to 16 carbon atoms; and (b) a glycol component comprising:
- i) 10 to 30 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
- ii) 70 to 90 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to less than 0.75 dL/g as determined in 60/40 (wt/wt) phenol/tetrachloroethane at a concentration of 0.5 g/100 ml at 25° C.; and wherein the polyester has a Tg of 85 to 120° C.

In one aspect, this invention relates to a polyester composition comprising at least one polyester which comprises:

(a) a dicarboxylic acid component comprising:
- i) 70 to 100 mole % of terephthalic acid residues;
- ii) 0 to 30 mole % of aromatic dicarboxylic acid residues having up to 20 carbon atoms; and
- iii) 0 to 10 mole % of aliphatic dicarboxylic acid residues having up to 16 carbon atoms; and (b) a glycol component comprising:
- i) 14 to 25 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
- ii) 75 to 86 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to less than 0.75 dL/g as determined in 60/40 (wt/wt) phenol/tetrachloroethane at a concentration of 0.5 g/100 ml at 25° C.; and wherein the polyester has a Tg of 85 to 120° C.

In one aspect, this invention relates to a polyester composition comprising at least one polyester which comprises:

(a) a dicarboxylic acid component comprising:
- i) 70 to 100 mole % of terephthalic acid residues;
- ii) 0 to 30 mole % of aromatic dicarboxylic acid residues having up to 20 carbon atoms; and
- iii) 0 to 10 mole % of aliphatic dicarboxylic acid residues having up to 16 carbon atoms; and (b) a glycol component comprising:
- i) 5 to less than 50 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) greater than 50 to 95 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to less than 0.75 dL/g as determined in 60/40 (wt/wt) phenol/tetrachloroethane at a concentration of 0.5 g/100 ml at 25° C.; and wherein the polyester has a Tg of 95 to 115° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 10 to 30 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 70 to 90 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to less than 0.75 dL/g as determined in 60/40 (wt/wt) phenol/tetrachloroethane at a concentration of 0.5 g/100 ml at 25° C.; and wherein the polyester has a Tg of 95 to 115° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 14 to 25 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 75 to 86 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.50 to less than 0.75 dL/g as determined in 60/40 (wt/wt) phenol/tetrachloroethane at a concentration of 0.5 g/100 ml at 25° C.; and wherein the polyester has a Tg of 95 to 115° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 14 to 25 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 75 to 86 mole % of 1,4-cyclohexanedimethanol residues, wherein the total mole % of the dicarboxylic acid component is 100 mole %, and the total mole % of the glycol component is 100 mole %; and wherein the inherent viscosity of the polyester is from 0.6 to 0.72 dL/g as determined in 60/40 (wt/wt) phenol/tetrachloroethane at a concentration of 0.5 g/100 ml at 25° C.; and wherein the polyester has a Tg of 95 to 115° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to less than 5 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) optionally, 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 4.5 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) optionally, 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 4 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) optionally, 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 3 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 2.0 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) optionally, 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 1 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to less than 1 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 15 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 0.01 to 15 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 ii) 70 to 99.98 mole % ethylene glycol residues, and
 iii) 0.01 to 15 mole % of 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 0.01 to 10 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 0.01 to 10 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 ii) 80 to 99.98 mole % of ethylene glycol residues, and
 iii) 0.01 to 10 mole % of 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 0.01 to 5 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 ii) ethylene glycol residues, and
 iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 0.01 to less than 5 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and
 ii) ethylene glycol residues, and
 iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:
 i) 70 to 100 mole % of terephthalic acid residues;
 ii) 0 to 30 mole % of aromatic dicarboxylic acid residues having up to 20 carbon atoms; and
 iii) 0 to 10 mole % of aliphatic dicarboxylic acid residues having up to 16 carbon atoms; and
(b) a glycol component comprising:
 i) 0.01 to 4.5 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 4 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 3 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 2.0 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 1 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to less than 1 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) ethylene glycol residues, and iii) 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

A polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 5 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 90 to 99.98 mole % of ethylene glycol residues, and iii) 0.01 to 5 mole % of 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to less than 5 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) greater than 90 to 99.98 mole % of ethylene glycol residues, and iii) 0.01 to 5 mole % of 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 4 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 91 to 99.98 mole % of ethylene glycol residues, and iii) 0.01 to 5 mole % of 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 3 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 92 to 99.98 mole % of ethylene glycol residues, and iii) 0.01 to 5 mole % of 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 2 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 93 to 99.98 mole % of ethylene glycol residues, and iii) 0.01 to 5 mole % of 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to 1 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) 94 to 99.98 mole % of ethylene glycol residues, and iii) 0.01 to 5 mole % of 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, this invention relates to a polyester composition comprising at least one polyester which comprises:

(a) a dicarboxylic acid component comprising:

i) 70 to 100 mole % of terephthalic acid residues;

ii) 0 to 30 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 0.01 to less than 1 mole % of 2,2,4,4-tetramethyl-1,3-cyclobutanediol residues comprising greater than 50 mole % cis-2,2,4,4-tetramethyl-1,3-cyclobutanediol residues and less than 50 mole % trans-2,2,4,4-tetramethyl-1,3-cyclobutanediol residues; and ii) greater than 94 to 99.98 mole % of ethylene glycol residues, and iii) 0.01 to 5 mole % of 1,4-cyclohexanedimethanol residues wherein the total mole % of the dicarboxylic acid component is 100 mole %, and the total mole % of the glycol component is 100 mole %; and wherein the inherent viscosity of the polyester is from 0.35 to 1.2 dL/g as determined in 60/40 (wt/wt) phenol/tetrachloroethane at a concentration of 0.5 g/100 ml at 25° C.; and wherein the polyester has a Tg of 60 to 120° C.

In one aspect, the polyester compositions of the invention contain at least one polycarbonate.

In one aspect, the polyester compositions of the invention contain no polycarbonate.

In one aspect, the polyesters useful in the invention contain less than 15 mole % ethylene glycol residues, such as, for example, 0.01 to less than 15 mole % ethylene glycol residues.

In one aspect, the polyesters useful in the invention contain no ethylene glycol residues.

In one aspect the polyester compositions useful in the invention contain at least one thermal stabilizer and/or reaction products thereof.

In one aspect, the polyesters useful in the invention contain no branching agent, or alternatively, at least one branching agent is added either prior to or during polymerization of the polyester.

In one aspect, the polyesters useful in the invention contain at least one branching agent without regard to the method or sequence in which it is added.

In one aspect, the polyesters useful in the invention are made from no 1,3-propanediol, or, 1,4-butanediol, either singly or in combination. In other aspects, 1,3-propanediol or 1,4-butanediol, either singly or in combination, may be used in the making of the polyesters useful in this invention.

In one aspect of the invention, the mole % of cis-2,2,4,4-tetramethyl-1,3-cyclobutanediol useful in certain polyesters useful in the invention is greater than 50 mole % or greater than 55 mole % of cis-2,2,4,4-tetramethyl-1,3-cyclobutanediol or greater than 70 mole % of cis-2,2,4,4-tetramethyl-1,3-cyclobutanediol; wherein the total mole percentage of cis-2,2,4,4-tetramethyl-1,3-cyclobutanediol and trans-2,2,4,4-tetramethyl-1,3-cyclobutanediol is equal to a total of 100 mole %.

In one aspect, the polyester compositions are useful in articles of manufacture including but not limited to extruded, calendered, and/or molded articles including but not limited to injection molded articles, thermoformed articles, extruded articles, cast extrusion articles, profile extrusion articles, melt spun articles, extrusion molded articles, injection blow molded articles, injection stretch blow molded articles, extrusion blow molded articles and extrusion stretch blow molded articles.

In one aspect, the polyester compositions are useful in articles of manufacture including, but not limited to, extruded, calendered, and/or molded articles including but not limited to, injection molded articles, extruded articles, cast extrusion articles, profile extrusion articles, melt spun articles, thermoformed articles, extrusion molded articles, injection blow molded articles, injection stretch blow molded articles and extrusion blow molded articles. These articles can include, but are not limited, to films, bottles (including, but not limited to, baby bottles), containers, sheet and/or fibers.

In one aspect, the polyester compositions useful in the invention may be used in various types of film and/or sheet, including but not limited to extruded film(s) and/or sheet(s), calendered film(s) and/or sheet(s), compression molded film(s) and/or sheet(s), solution casted film(s) and/or sheet(s). Methods of making film and/or sheet include but are not limited to extrusion, calendering, compression molding, and solution casting.

Also, in one aspect, use of these particular polyester compositions minimizes and/or eliminates the drying step prior to melt processing or thermoforming.

In one aspect, certain polyesters useful in the invention are amorphous or semicrystalline. In one aspect, certain polyesters useful in the invention can have a relatively low crystallinity. Certain polyesters useful in the invention can thus have a substantially amorphous morphology, meaning that the polyesters comprise substantially unordered regions of polymer.

DETAILED DESCRIPTION OF THE INVENTION

Figure 1:
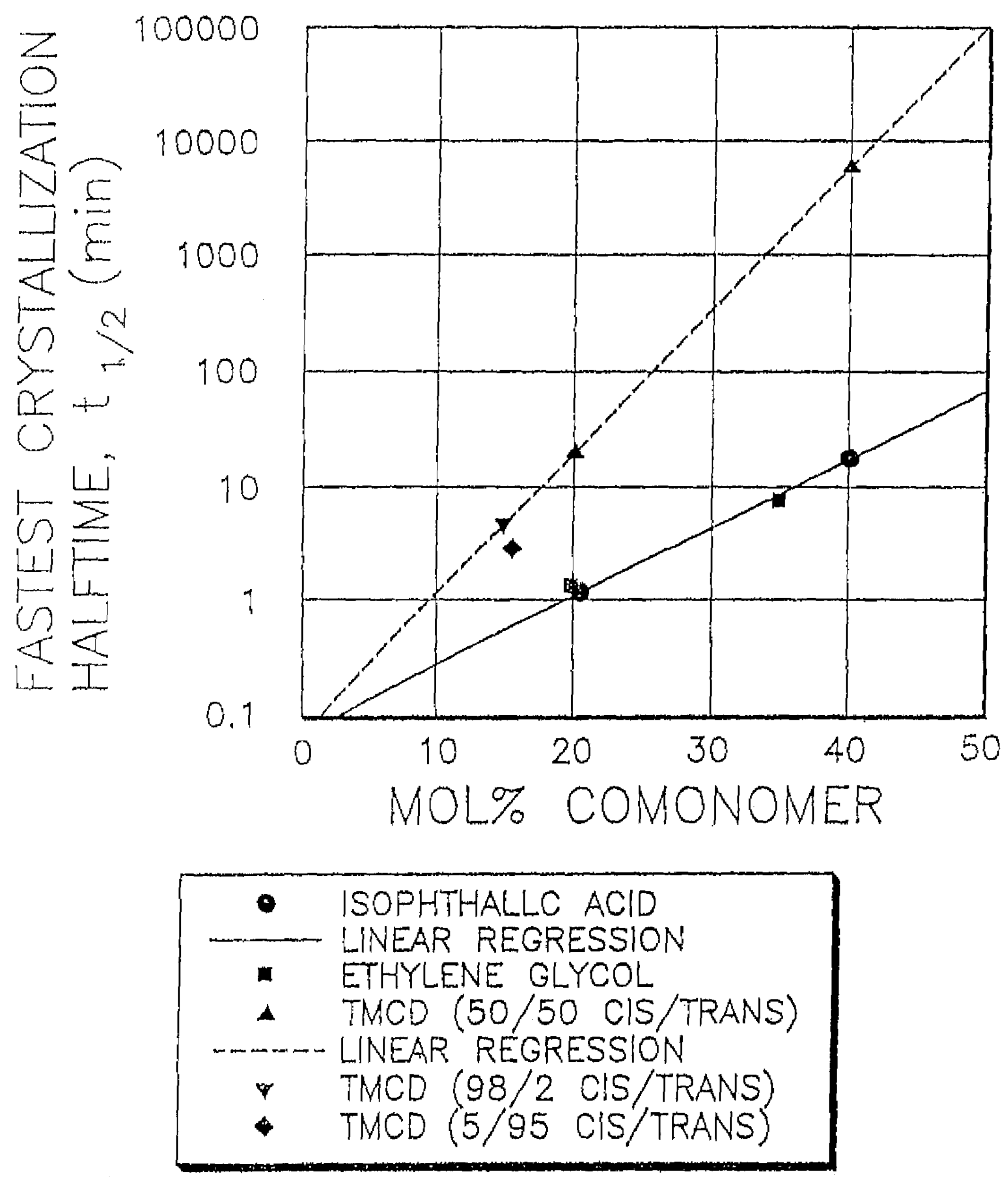
FIG. 1 is a graph showing the effect of comonomer on the fastest crystallization half-times of modified PCT copolyesters.

The present invention may be understood more readily by reference to the following detailed description of certain embodiments of the invention and the working examples. In accordance with the purpose(s) of this invention, certain embodiments of the invention are described in the Summary of the Invention and are further described herein below. Also, other embodiments of the invention are described herein.

It is believed that polyesters and/or polyester composition(s) of the invention can have a unique combination of two or more physical properties such as moderate or high impact strengths, high glass transition temperatures, chemical resistance, hydrolytic stability, toughness, low ductile-to-brittle transition temperatures, good color and clarity, low densities, and long crystallization half-times, and good processability thereby easily permitting them to be formed into articles. In some of the embodiments of the invention, the polyesters have a unique combination of the properties of good impact strength, heat resistance, chemical resistance, density and/or the combination of the properties of good impact strength, heat resistance, and processability and/or the combination of two or more of the described properties, that have never before been believed to be present in the polyester compositions which comprise the polyester(s) as disclosed herein.

The term "polyester", as used herein, is intended to include "copolyesters" and is understood to mean a synthetic polymer prepared by the reaction of one or more difunctional carboxylic acids and/or multifunctional carboxylic acids with one or more difunctional hydroxyl compounds and/or multifunctional hydroxyl compounds. Typically the difunctional carboxylic acid can be a dicarboxylic acid and the difunctional hydroxyl compound can be a dihydric alcohol such as, for example, glycols and diols. The term: "glycol" as used herein includes, but is not limited to, diols, glycols, and/or multifunctional hydroxyl compounds, for example, branching agents Alternatively, the difunctional carboxylic acid may be a hydroxy carboxylic acid such as, for example, p-hydroxybenzoic acid, and the difunctional hydroxyl compound may be an aromatic nucleus bearing 2 hydroxyl substituents such as, for example, hydroquinone. The term "residue", as used herein, means any organic structure incorporated into a polymer through a polycondensation and/or an esterification reaction from the corresponding monomer. The term "repeating unit", as used herein, means an organic structure having a dicarboxylic acid residue and a diol residue bonded through a carbonyloxy group. Thus, for example, the dicarboxylic acid residues may be derived from a dicarboxylic acid monomer or its associated acid halides, esters, salts, anhydrides, or mixtures thereof. Furthermore, as used herein, the term "diacid" includes multifunctional acids, for example, branching agents. As used herein, therefore, the term "dicarboxylic acid" is intended to include dicarboxylic acids and any derivative of a dicarboxylic acid, including its associated acid halides, esters, half-esters, salts, half-salts, anhydrides, mixed anhydrides, or mixtures thereof, useful in a reaction process with a diol to make polyester. As used herein, the term "terephthalic acid" is intended to include terephthalic acid itself and residues thereof as well as any derivative of terephthalic acid, including its associated acid halides, esters, half-esters, salts, half-salts, anhydrides, mixed anhydrides, or mixtures thereof or residues thereof useful in a reaction process with a diol to make polyester.

In one embodiment, terephthalic acid may be used as the starting material. In another embodiment, dimethyl terephthalate may be used as the starting material. In yet another embodiment, mixtures of terephthalic acid and dimethyl terephthalate may be used as the starting material and/or as an intermediate material.

The polyesters used in the present invention typically can be prepared from dicarboxylic acids and diols which react in substantially equal proportions and are incorporated into the polyester polymer as their corresponding residues. The polyesters of the present invention, therefore, can contain substantially equal molar proportions of acid residues (100 mole %) and diol (and/or multifunctional hydroxyl compound) residues (100 mole %) such that the total moles of repeating units is equal to 100 mole %. The mole percentages provided in the present disclosure, therefore, may be based on the total moles of acid residues, the total moles of diol residues, or the total moles of repeating units. For example, a polyester containing 30 mole % isophthalic acid, based on the total acid residues, means the polyester contains 30 mole % isophthalic acid residues out of a total of 100 mole % acid residues. Thus, there are 30 moles of isophthalic acid residues among every 100 moles of acid residues. In another example, a polyester containing 30 mole % 2,2,4,4-tetramethyl-1,3-cyclobutanediol, based on the total diol residues, means the polyester contains 30 mole % 2,2,4,4-tetramethyl-1,3-cyclobutanediol residues out of a total of 100 mole % diol residues. Thus, there are 30 moles of 2,2,4,4-tetramethyl-1,3-cyclobutanediol residues among every 100 moles of diol residues.

In other aspects of the invention, the Tg of the polyesters useful in the bottle(s) of the invention can be at least one of the following ranges: 60 to 200° C.; 60 to 190° C.; 60 to 180° C.; 60 to 170° C.; 60 to 160° C.; 60 to 155° C.; 60 to 150° C.; 60 to 145° C.; 60 to 140° C.; 60 to 138° C.; 60 to 135° C.; 60 to 130° C.; 60 to 125° C.; 60 to 120° C.; 60 to 115° C.; 60 to 110° C.; 60 to 105° C.; 60 to 100° C.; 60 to 95° C.; 60 to 90° C.; 60 to 85° C.; 60 to 80° C.; 60 to 75° C.; 65 to 200° C.; 65 to 190° C.; 65 to 180° C.; 65 to 170° C.; 65 to 160° C.; 65 to 155° C.; 65 to 150° C.; 65 to 145° C.; 65 to 140° C.; 65 to 138° C.; 65 to 135° C.; 65 to 130° C.; 65 to 125° C.; 65 to 120° C.; 65 to 115° C.; 65 to 110° C.; 65 to 105° C.; 65 to 100° C.; 65 to 95° C.; 65 to 90° C.; 65 to 85° C.; 65 to 80° C.; 65 to 75° C.; 70 to 200° C.; 70 to 190° C.; 70 to 180° C.; 70 to 170° C.; 70 to 160° C.; 70 to 155° C.; 70 to 150° C.; 70 to 145° C.; 70 to 140° C.; 70 to 138° C.; 70 to 135° C.; 70 to 130° C.; 70 to 125° C.; 70 to 120° C.; 70 to 115° C.; 70 to 110° C.; 70 to 105° C.; 70 to 100° C.; 70 to 95° C.; 70 to 90° C.; 70 to 85° C.; 70 to 80° C.; 70 to 75° C.; 75 to 200° C.; 75 to 190° C.; 75 to 180° C.; 75 to 170° C.; 75 to 160° C.; 75 to 155° C.; 75 to 150° C.; 75 to 145° C.; 75 to 140° C.; 75 to 138° C.; 75 to 135° C.; 75 to 130° C.; 75 to 125° C.; 75 to 120° C.; 75 to 115° C.; 75 to 110° C.; 75 to 105° C.; 75 to 100° C.; 75 to 95° C.; 75 to 90° C.; 75 to 85° C.; 75 to 80° C.; 80 to 200° C.; 80 to 190° C.; 80 to 180° C.; 80 to 170° C.; 80 to 160° C.; 80 to 155° C.; 80 to 150° C.; 80 to 145° C.; 80 to 140° C.; 80 to 138° C.; 80 to 135° C.; 80 to 130° C.; 80 to 125° C.; 80 to 120° C.; 80 to 115° C.; 80 to 110° C.; 80 to 105° C.; 80 to 100° C.; 80 to 95° C.; 80 to 90° C.; 80 to 85° C.; 85 to 200° C.; 85 to 190° C.; 85 to 180° C.; 85 to 170° C.; 85 to 160° C.; 85 to 155° C.; 85 to 150° C.; 85 to 145° C.; 85 to 140° C.; 85 to 138° C.; 85 to 135° C.; 85 to 130° C.; 85 to 125° C.; 85 to 120° C.; 85 to 115° C.; 85 to 110° C.; 85 to 105° C.; 85 to 100° C.; 85 to 95° C.; 85 to 90° C.; 90 to 200° C.; 90 to 190° C.; 90 to 180° C.; 90 to 170° C.; 90 to 160° C.; 90 to 155° C.; 90 to 150° C.; 90 to 145° C.; 90 to 140° C.; 90 to 138° C.; 90 to 135° C.; 90 to 130° C.; 90 to 125° C.; 90 to 120° C.; 90 to 115° C.; 90 to 110° C.; 90 to 105° C.; 90 to 100° C.; 90 to 95° C.; 95 to 200° C.; 95 to 190° C.; 95 to 180° C.; 95 to 170° C.; 95 to 160° C.; 95 to 155° C.; 95 to 150° C.; 95 to 145° C.; 95 to 140° C.; 95 to 138° C.; 95 to 135° C.; 95 to 130° C.; 95 to 125° C.; 95 to 120° C.; 95 to 115° C.; 95 to 110° C.; 95 to 105° C.; 95 to 100° C.; 100 to 200° C.; 100 to 190° C.; 100 to 180° C.; 100 to 170° C.; 100 to 160° C.; 100 to 155° C.; 100 to 150° C.; 100 to 145° C.; 100 to 140° C.; 100 to 138° C.; 100 to 135° C.; 100 to 130° C.; 100 to 125° C.; 100 to 120° C.; 100 to 115° C.; 100 to 110° C.; 105 to 200° C.; 105 to 190° C.; 105 to 180° C.; 105 to 170° C.; 105 to 160° C.; 105 to 155° C.; 105 to 150° C.; 105 to 145° C.; 105 to 140° C.; 105 to 138° C.; 105 to 135° C.; 105 to 130° C.; 105 to 125° C.; 105 to 120° C.; 105 to 115° C.; 105 to 110° C.; 110 to 200° C.; 110 to 190° C.; 110 to 180° C.; 110 to 170° C.; 110 to 160° C.; 110 to 155° C.; 110 to 150° C.; 110 to 145° C.; 110 to 140° C.; 110 to 138° C.; 110 to 135° C.; 110 to 130° C.; 110 to 125° C.; 110 to 120° C.; 110 to 115° C.; 115 to 200° C.; 115 to 190° C.; 115 to 180° C.; 115 to 170° C.; 115 to 160° C.; 115 to 155° C.; 115 to 150° C.; 115 to 145° C.; 115 to 140° C.; 115 to 138° C.; 115 to 135° C.; 110 to 130° C.; 115 to 125° C.; 115 to 120° C.; 120 to 200° C.; 120 to 190° C.; 120 to 180° C.; 120 to 170° C.; 120 to 160° C.; 120 to 155° C.; 120 to 150° C.; 120 to 145° C.; 120 to 140° C.; 120 to 138° C.; 120 to 135° C.; 120 to 130° C.; 125 to 200° C.; 125 to 190° C.; 125 to 180° C.; 125 to 170° C.; 125 to 165°

C.; 125 to 160° C.; 125 to 155° C.; 125 to 150° C.; 125 to 145° C.; 125 to 140° C.; 125 to 138° C.; 125 to 135° C.; 127 to 200° C.; 127 to 190° C.; 127 to 180° C.; 127 to 170° C.; 127 to 160° C.; 127 to 150° C.; 127 to 145° C.; 127 to 140° C.; 127 to 138° C.; 127 to 135° C.; 130 to 200° C.; 130 to 190° C.; 130 to 180° C.; 130 to 170° C.; 130 to 160° C.; 130 to 155° C.; 130 to 150° C.; 130 to 145° C.; 130 to 140° C.; 130 to 138° C.; 130 to 135° C.; 135 to 200° C.; 135 to 190° C.; 135 to 180° C.; 135 to 170° C.; 135 to 160° C.; 135 to 155° C.; 135 to 150° C.; 135 to 145° C.; 135 to 140° C.; 140 to 200° C.; 140 to 190° C.; 140 to 180° C.; 140 to 170° C.; 140 to 160° C.; 140 to 155° C.; 140 to 150° C.; 140 to 145° C.; 148 to 200° C.; 148 to 190° C.; 148 to 180° C.; 148 to 170° C.; 148 to 160° C.; 148 to 155° C.; 148 to 150° C.; greater than 148 to 200° C.; greater than 148 to 190° C.; greater than 148 to 180° C.; greater than 148 to 170° C.; greater than 148 to 160° C.; greater than 148 to 155° C.; 150 to 200° C.; 150 to 190° C.; 150 to 180° C.; 150 to 170° C.; 150 to 160; 155 to 190° C.; 155 to 180° C.; 155 to 170° C.; and 155 to 165° C.

In other aspects of the invention, the glycol component for the polyesters useful in the invention include but are not limited to at least one of the following combinations of ranges: 1 to 99 mole % 2,2,4,4-tetramethyl-1,3-cyclobutanediol and 1 to 99 mole % 1,4-cyclohexanedimethanol; 1 to 95 mole % 2,2,4,4-tetramethyl-1,3-cyclobutanediol and 5 to 99 mole % 1,4-cyclohexanedimethanol; 1 to 90 mole % 2,2,4,4-tetramethyl-1,3-cyclobutanediol and 10 to 99 mole % 1,4-cyclohexanedimethanol; 1 to 85 mole % 2,2,4,4-tetramethyl-1,3-cyclobutanediol and 15 to 99 mole % 1,4-cyclohexanedimethanol; 1 to 80 mole % 2,2,4,4-tetramethyl-1,3-cyclobutanediol and 20 to 99 mole % 1,4-cyclohexanedimethanol, 1 to 75 mole % 2,2,4,4-tetramethyl-1,3-cyclobutanediol and 25 to 99 mole % 1,4-cyclohexanedimethanol; 1 to 70 mole % 2,2,4,4-tetramethyl-1,3-cyclobutanediol and 30 to 99 mole % 1,4-cyclohexanedimethanol; 1 to 65 mole % 2,2,4,4-tetramethyl-1,3-cyclobutanediol and 35 to 99 mole % 1,4-cyclohexanedimethanol; 1 to 60 mole % 2,2,4,4-tetramethyl-1,3-cyclobutanediol and 40 to 99 mole % 1,4-cyclohexanedimethanol; 1 to 55 mole % 2,2,4,4-tetramethyl-1,3-cyclobutanediol and 45 to 99 mole % 1,4-cyclohexanedimethanol; 1 to 50 mole % 2,2,4,4-tetramethyl-1,3-cyclobutanediol and 50 to 99 mole % 1,4-cyclohexanedimethanol; 1 to 45 mole % 2,2,4,4-tetramethyl-1,3-cyclobutanediol and 55 to 99 mole % 1,4-cyclohexanedimethanol; 1 to 40 mole % 2,2,4,4-tetramethyl-1,3-cyclobutanediol and 60 to 99 mole % 1,4-cyclohexanedimethanol; 1 to 35 mole % 2,2,4,4-tetramethyl-1,3-cyclobutanediol and 65 to 99 mole % 1,4-cyclohexanedimethanol; 1 to 30 mole % 2,2,4,4-tetramethyl-1,3-cyclobutanediol and 70 to 99 mole % 1,4-cyclohexanedimethanol; 1 to 25 mole % 2,2,4,4-tetramethyl-1,3-cyclobutanediol and 75 to 99 mole % 1,4-cyclohexanedimethanol; 1 to 20 mole % 2,2,4,4-tetramethyl-1,3-cyclobutanediol and 80 to 99 mole % 1,4-cyclohexanedimethanol; 1 to 15 mole % 2,2,4,4-tetramethyl-1,3-cyclobutanediol and 85 to 99 mole % 1,4-cyclohexanedimethanol; 1 to 10 mole % 2,2,4,4-tetramethyl-1,3-cyclobutanediol and 90 to 99 mole % 1,4-cyclohexanedimethanol; and 1 to 5 mole % 2,2,4,4-tetramethyl-1,3-cyclobutanediol and 95 to 99 mole % 1,4-cyclohexanedimethanol.

In other aspects of the invention, the glycol component for the polyesters useful in the invention include but are not limited to at least one of the following combinations of ranges: 0.01 to less than 5 mole % 2,2,4,4-tetramethyl-1,3-cyclobutanediol and 95 to 99.99 mole % 1,4-cyclohexanedimethanol; 0.01 to 4.5 mole % 2,2,4,4-tetramethyl-1,3-cyclobutanediol and 95.5 to 99.99 mole % 1,4-cyclohexanedimethanol; 0.01 to 4 mole % 2,2,4,4-tetramethyl-1,3-cyclobutanediol and 96 to 99.99 mole % 1,4-cyclohexanedimethanol; 0.01 to 3.5 mole % 2,2,4,4-tetramethyl-1,3-cyclobutanediol and 96.5 to 99.99 mole % 1,4-cyclohexanedimethanol; 0.01 to 3 mole % 2,2,4,4-tetramethyl-1,3-cyclobutanediol and 97 to 99.99 mole % 1,4-cyclohexanedimethanol; 0.01 to 2.5 mole % 2,2,4,4-tetramethyl-1,3-cyclobutanediol and 97.5 to 99.99 mole % 1,4-cyclohexanedimethanol; 0.01 to 2 mole % 2,2,4,4-tetramethyl-1,3-cyclobutanediol and 98 to 99.99 mole % 1,4-cyclohexanedimethanol; 0.01 to 1.5 mole % 2,2,4,4-tetramethyl-1,3-cyclobutanediol and 98.5 to 99.99 mole % 1,4-cyclohexanedimethanol; 0.01 to 1 mole % 2,2,4,4-tetramethyl-1,3-cyclobutanediol and 99 to 99.99 mole % 1,4-cyclohexanedimethanol; and 0.01 to 0.5 mole % 2,2,4,4-tetramethyl-1,3-cyclobutanediol and 99.5 to 99.99 mole % 1,4-cyclohexanedimethanol.

In other aspects of the invention, the glycol component for the polyesters useful in the invention include but are not limited to at least one of the following combinations of ranges: 5 to 99 mole % 2,2,4,4-tetramethyl-1,3-cyclobutanediol and 1 to 95 mole % 1,4-cyclohexanedimethanol; 5 to 95 mole % 2,2,4,4-tetramethyl-1,3-cyclobutanediol and 5 to 95 mole % 1,4-cyclohexanedimethanol; 5 to 90 mole % 2,2,4,4-tetramethyl-1,3-cyclobutanediol and 10 to 95 mole % 1,4-cyclohexanedimethanol; 5 to 85 mole % 2,2,4,4-tetramethyl-1,3-cyclobutanediol and 15 to 95 mole % 1,4-cyclohexanedimethanol; 5 to 80 mole % 2,2,4,4-tetramethyl-1,3-cyclobutanediol and 20 to 95 mole % 1,4-cyclohexanedimethanol, 5 to 75 mole % 2,2,4,4-tetramethyl-1,3-cyclobutanediol and 25 to 95 mole % 1,4-cyclohexanedimethanol; 5 to 70 mole % 2,2,4,4-tetramethyl-1,3-cyclobutanediol and 30 to 95 mole % 1,4-cyclohexanedimethanol; 5 to 65 mole % 2,2,4,4-tetramethyl-1,3-cyclobutanediol and 35 to 95 mole % 1,4-cyclohexanedimethanol; 5 to 60 mole % 2,2,4,4-tetramethyl-1,3-cyclobutanediol and 40 to 95 mole % 1,4-cyclohexanedimethanol; 5 to 55 mole % 2,2,4,4-tetramethyl-1,3-cyclobutanediol and 45 to 95 mole % 1,4-cyclohexanedimethanol; and 5 to 50 mole % 2,2,4,4-tetramethyl-1,3-cyclobutanediol and 50 to 95 mole % 1,4-cyclohexanedimethanol.

In other aspects of the invention, the glycol component for the polyesters useful in the invention include but are not limited to at least one of the following combinations of ranges: 5 to less than 50 mole % 2,2,4,4-tetramethyl-1,3-cyclobutanediol and greater than 50 to 95 mole % 1,4-cyclohexanedimethanol; 5 to 45 mole % 2,2,4,4-tetramethyl-1,3-cyclobutanediol and 55 to 95 mole % 1,4-cyclohexanedimethanol; 5 to 40 mole % 2,2,4,4-tetramethyl-1,3-cyclobutanediol and 60 to 95 mole % 1,4-cyclohexanedimethanol; 5 to 35 mole % 2,2,4,4-tetramethyl-1,3-cyclobutanediol and 65 to 95 mole % 1,4-cyclohexanedimethanol; 5 to less than 35 mole % 2,2,4,4-tetramethyl-1,3-cyclobutanediol and greater than 65 to 95 mole % 1,4-cyclohexanedimethanol; 5 to 30 mole % 2,2,4,4-tetramethyl-1,3-cyclobutanediol and 70 to 95 mole % 1,4-cyclohexanedimethanol; 5 to 25 mole % 2,2,4,4-tetramethyl-1,3-cyclobutanediol and 75 to 95 mole % 1,4-cyclohexanedimethanol; 5 to 20 mole % 2,2,4,4-tetramethyl-1,3-cyclobutanediol and 80 to 95 mole % 1,4-cyclohexanedimethanol; 5 to 15 mole % 2,2,4,4-tetramethyl-1,3-cyclobutanediol and 85 to 95 mole % 1,4-cyclohexanedimethanol; 5 to 10 mole % 2,2,4,4-tetramethyl-1,3-cyclobutanediol and 90 to 95 mole % 1,4- cyclohexanedimethanol; greater than 5 to less than 10 mole % 2,2,4,4-tetramethyl-1,3-cyclobutanediol and less than 90 to greater than 95 mole % 1,4-cyclohexanedimethanol; 5.5 mole % to 9.5 mole % 2,2,4,4-tetramethyl-1,3-cyclobutanediol and 94.5 mole % to 90.5 mole % 1,4-cyclohexanedimethanol; and 6 to 9 mole % 2,2,4,4-tetramethyl-1,3-cyclobutanediol and 94 to 91 mole % 1,4-cyclohexanedimethanol.

In other aspects of the invention, the glycol component for the polyesters useful in the invention include but are not limited to at least one of the following combinations of ranges: 10 to 99 mole % 2,2,4,4-tetramethyl-1,3-cyclobutanediol and 1 to 90 mole % 1,4-cyclohexanedimethanol; 10 to 95 mole % 2,2,4,4-tetramethyl-1,3-cyclobutanediol and 5 to 90 mole % 1,4-cyclohexanedimethanol; 10 to 90 mole % 2,2,4,4-tetramethyl-1,3-cyclobutanediol and 10 to 90 mole % 1,4-cyclohexanedimethanol; 10 to 85 mole % 2,2,4,4-tetramethyl-1,3-cyclobutanediol and 15 to 90 mole % 1,4-cyclohexanedimethanol; 10 to 80 mole % 2,2,4,4-tetramethyl-1,3-cyclobutanediol and 20 to 90 mole % 1,4-cyclohexanedimethanol; 10 to 75 mole % 2,2,4,4-tetramethyl-1,3-cyclobutanediol and 25 to 90 mole % 1,4-cyclohexanedimethanol; 10 to 70 mole % 2,2,4,4-tetramethyl-1,3-cyclobutanediol and 30 to 90 mole % 1,4-cyclohexanedimethanol; 10 to 65 mole % 2,2,4,4-tetramethyl-1,3-cyclobutanediol and 35 to 90 mole % 1,4-cyclohexanedimethanol; 10 to 60 mole % 2,2,4,4-tetramethyl-1,3-cyclobutanediol and 40 to 90 mole % 1,4-cyclohexanedimethanol; 10 to 55 mole % 2,2,4,4-tetramethyl-1,3-cyclobutanediol and 45 to 90 mole % 1,4-cyclohexanedimethanol; 10 to 50 mole % 2,2,4,4-tetramethyl-1,3-cyclobutanediol and 50 to 90 mole % 1,4-cyclohexanedimethanol; 10 to less than 50 mole % 2,2,4,4-tetramethyl-1,3-cyclobutanediol and greater than 50 to 90 mole % 1,4-cyclohexanedimethanol; 10 to 45 mole % 2,2,4,4-tetramethyl-1,3-cyclobutanediol and 55 to 90 mole % 1,4-cyclohexanedimethanol; 10 to 40 mole % 2,2,4,4-tetramethyl-1,3-cyclobutanediol and 60 to 90 mole % 1,4-cyclohexanedimethanol; 10 to 35 mole % 2,2,4,4-tetramethyl-1,3-cyclobutanediol and 65 to 90 mole % 1,4-cyclohexanedimethanol; 10 to less than 35 mole % 2,2,4,4-tetramethyl-1,3-cyclobutanediol and greater than 65 to 90% 1,4-cyclohexanedimethanol; 10 to 30 mole % 2,2,4,4-tetramethyl-1,3-cyclobutanediol and 70 to 90 mole % 1,4-cyclohexanedimethanol; 10 to 25 mole % 2,2,4,4-tetramethyl-1,3-cyclobutanediol and 75 to 90 mole % 1,4-cyclohexanedimethanol; 10 to 20 mole % 2,2,4,4-tetramethyl-1,3-cyclobutanediol and 80 to 90 mole % 1,4-cyclohexanedimethanol; and 10 to 15 mole % 2,2,4,4-tetramethyl-1,3-cyclobutanediol and 85 to 90 mole % 1,4-cyclohexanedimethanol.

In other aspects of the invention, the glycol component for the polyesters useful in the invention include but are not limited to at least one of the following combinations of ranges: 14 to 99 mole % 2,2,4,4-tetramethyl-1,3-cyclobutanediol and 1 to 86 mole % 1,4-cyclohexanedimethanol; 14 to 95 mole % 2,2,4,4-tetramethyl-1,3-cyclobutanediol and 5 to 86 mole % 1,4-cyclohexanedimethanol; 14 to 90 mole % 2,2,4,4-tetramethyl-1,3-cyclobutanediol and 10 to 86 mole % 1,4-cyclohexanedimethanol; 14 to 85 mole % 2,2,4,4-tetramethyl-1,3-cyclobutanediol and 15 to 86 mole % 1,4-cyclohexanedimethanol; 14 to 80 mole % 2,2,4,4-tetramethyl-1,3-cyclobutanediol and 20 to 86 mole % 1,4-cyclohexanedimethanol; 14 to 75 mole % 2,2,4,4-tetramethyl-1,3-cyclobutanediol and 25 to 86 mole % 1,4-cyclohexanedimethanol; 14 to 70 mole % 2,2,4,4-tetramethyl-1,3-cyclobutanediol and 30 to 86 mole % 1,4-cyclohexanedimethanol; 14 to 65 mole % 2,2,4,4-tetramethyl-1,3-cyclobutanediol and 35 to 86 mole % 1,4-cyclohexanedimethanol; 14 to 60 mole % 2,2,4,4-tetramethyl-1,3-cyclobutanediol and 40 to 86 mole % 1,4-cyclohexanedimethanol; 14 to 55 mole % 2,2,4,4-tetramethyl-1,3-cyclobutanediol and 45 to 86 mole % 1,4-cyclohexanedimethanol; 14 to 50 mole % 2,2,4,4-tetramethyl-1,3-cyclobutanediol and 50 to 86 mole % 1,4-cyclohexanedimethanol; 14 to less than 50 mole % 2,2,4,4-tetramethyl-1,3-cyclobutanediol and greater than 50 to 86 mole % 1,4-cyclohexanedimethanol; 14 to 45 mole % 2,2,4,4-tetramethyl-1,3-cyclobutanediol and 55 to 86 mole % 1,4-cyclohexanedimethanol; 14 to 40 mole % 2,2,4,4-tetramethyl-1,3-cyclobutanediol and 60 to 86 mole % 1,4-cyclohexanedimethanol; 14 to 35 mole % 2,2,4,4-tetramethyl-1,3-cyclobutanediol and 65 to 86 mole % 1,4-cyclohexanedimethanol; 14 to 30 mole % 2,2,4,4-tetramethyl-1,3-cyclobutanediol and 70 to 86 mole % 1,4-cyclohexanedimethanol; 14 to 24 mole % 2,2,4,4-tetramethyl-1,3-cyclobutanediol and 76 to 86 mole % 1,4-cyclohexanedimethanol; and 14 to 25 mole % 2,2,4,4-tetramethyl-1,3-cyclobutanediol and 75 to 86 mole % 1,4-cyclohexanedimethanol.

In other aspects of the invention, the glycol component for the polyesters useful in the invention include but are not limited to at least one of the following combinations of ranges: 15 to 99 mole % 2,2,4,4-tetramethyl-1,3-cyclobutanediol and 1 to 85 mole % 1,4-cyclohexanedimethanol; 15 to 95 mole % 2,2,4,4-tetramethyl-1,3-cyclobutanediol and 5 to 85 mole % 1,4-cyclohexanedimethanol; 15 to 90 mole % 2,2,4,4-tetramethyl-1,3-cyclobutanediol and 10 to 85 mole % 1,4-cyclohexanedimethanol; 15 to 85 mole % 2,2,4,4-tetramethyl-1,3-cyclobutanediol and 15 to 85 mole % 1,4-cyclohexanedimethanol; 15 to 80 mole % 2,2,4,4-tetramethyl-1,3-cyclobutanediol and 20 to 85 mole % 1,4-cyclohexanedimethanol; 15 to 75 mole % 2,2,4,4-tetramethyl-1,3-cyclobutanediol and 25 to 85 mole % 1,4-cyclohexanedimethanol; 15 to 70 mole % 2,2,4,4-tetramethyl-1,3-cyclobutanediol and 30 to 85 mole % 1,4-cyclohexanedimethanol; 15 to 65 mole % 2,2,4,4-tetramethyl-1,3-cyclobutanediol and 35 to 85 mole % 1,4-cyclohexanedimethanol; 15 to 60 mole % 2,2,4,4-tetramethyl-1,3-cyclobutanediol and 40 to 85 mole % 1,4-cyclohexanedimethanol; 15 to 55 mole % 2,2,4,4-tetramethyl-1,3-cyclobutanediol and 45 to 85 mole % 1,4-cyclohexanedimethanol; 15 to 50 mole % 2,2,4,4-tetramethyl-1,3-cyclobutanediol and 50 to 85 mole % 1,4-cyclohexanedimethanol; 15 to less than 50 mole % 2,2,4,4-tetramethyl-1,3-cyclobutanediol and greater than 50 to 85 mole % 1,4-cyclohexanedimethanol; 15 to 45 mole % 2,2,4,4-tetramethyl-1,3-cyclobutanediol and 55 to 85 mole % 1,4-cyclohexanedimethanol; 15 to 40 mole % 2,2,4,4-tetramethyl-1,3-cyclobutanediol and 60 to 85 mole % 1,4-cyclohexanedimethanol; 15 to 35 mole % 2,2,4,4-tetramethyl-1,3-cyclobutanediol and 65 to 85 mole % 1,4-cyclohexanedimethanol; 15 to 30 mole % 2,2,4,4-tetramethyl-1,3-cyclobutanediol and 70 to 85 mole % 1,4-cyclohexanedimethanol; 15 to 25 mole % 2,2,4,4-tetramethyl-1,3-cyclobutanediol and 75 to 85 mole % 1,4-cyclohexanedimethanol; and 15 to 24 mole % 2,2,4,4-tetramethyl-1,3-cyclobutanediol and 76 to 85 mole % 1,4-cyclohexanedimethanol.

In other aspects of the invention, the glycol component for the polyesters useful in the invention include but are not limited to at least one of the following combinations of ranges: 20 to 99 mole % 2,2,4,4-tetramethyl-1,3-cyclobutanediol and 1 to 80 mole % 1,4-cyclohexanedimethanol; 20 to 95 mole % 2,2,4,4-tetramethyl-1,3-cyclobutanediol and 5 to 80 mole % 1,4-cyclohexanedimethanol; 20 to 90 mole % 2,2,4,4-tetramethyl-1,3-cyclobutanediol and 10 to 80 mole % 1,4-cyclohexanedimethanol; 20 to 85 mole % 2,2,4,4-tetramethyl-1,3-cyclobutanediol and 15 to 80 mole % 1,4-cyclohexanedimethanol; 20 to 80 mole % 2,2,4,4-tetramethyl-1,3-cyclobutanediol and 20 to 80 mole % 1,4-cyclohexanedimethanol; 20 to 75 mole % 2,2,4,4-tetramethyl-1,3-cyclobutanediol and 25 to 80 mole % 1,4-cyclohexanedimethanol; 20 to 70 mole % 2,2,4,4-tetramethyl-1,3-cyclobutanediol and 30 to 80 mole % 1,4-cyclohexanedimethanol; 20 to 65 mole % 2,2,4,4-tetramethyl-1,3-cyclobutanediol and 35 to 80 mole % 1,4-cyclohexanedimethanol; 20 to 60 mole % 2,2,4,4-tetramethyl-1,3-cyclobutanediol and 40 to 80 mole % 1,4-cyclohexanedimethanol; 20 to 55 mole % 2,2,4,4-tetramethyl-1,3-cyclobutanediol and 45 to 80 mole % 1,4-cyclohexanedimethanol; 20 to 50 mole % 2,2,4,4-tetramethyl-1,3-cyclobutanediol and 50 to 80 mole % 1,4-cyclohexanedimethanol; 20 to less than 50 mole % 2,2,4,4-tetramethyl-1,3-cyclobutanediol and greater than 50 to 80 mole % 1,4-cyclohexanedimethanol; 20 to 45 mole % 2,2,4,4-tetramethyl-1,3-cyclobutanediol and 55 to 80 mole % 1,4-cyclohexanedimethanol; 20 to 40 mole % 2,2,4,4-tetramethyl-1,3-cyclobutanediol and 60 to 80 mole % 1,4-cyclohexanedimethanol; 20 to 35 mole % 2,2,4,4-tetramethyl-1,3-cyclobutanediol and 65 to 80 mole % 1,4-cyclohexanedimethanol; 20 to 30 mole % 2,2,4,4-tetramethyl-1,3-cyclobutanediol and 70 to 80 mole % 1,4-cyclohexanedimethanol; and 20 to 25 mole % 2,2,4,4-tetramethyl-1,3-cyclobutanediol and 75 to 80 mole % 1,4-cyclohexanedimethanol.

In other aspects of the invention, the glycol component for the polyesters useful in the invention include but are not limited to at least one of the following combinations of ranges: 25 to 99 mole % 2,2,4,4-tetramethyl-1,3-cyclobutanediol and 1 to 75 mole % 1,4-cyclohexanedimethanol; 25 to 95 mole % 2,2,4,4-tetramethyl-1,3-cyclobutanediol and 5 to 75 mole % 1,4-cyclohexanedimethanol; 25 to 90 mole % 2,2,4,4-tetramethyl-1,3-cyclobutanediol and 10 to 75 mole % 1,4-cyclohexanedimethanol; 25 to 85 mole % 2,2,4,4-tetramethyl-1,3-cyclobutanediol and 15 to 75 mole % 1,4-cyclohexanedimethanol; 25 to 80 mole % 2,2,4,4-tetramethyl-1,3-cyclobutanediol and 20 to 75 mole % 1,4-cyclohexanedimethanol; 25 to 75 mole % 2,2,4,4-tetramethyl-1,3-cyclobutanediol and 25 to 75 mole % 1,4-cyclohexanedimethanol; 25 to 70 mole % 2,2,4,4-tetramethyl-1,3-cyclobutanediol and 30 to 75 mole % 1,4-cyclohexanedimethanol; 25 to 65 mole % 2,2,4,4-tetramethyl-1,3-cyclobutanediol and 35 to 75 mole % 1,4-cyclohexanedimethanol; 25 to 60 mole % 2,2,4,4-tetramethyl-1,3-cyclobutanediol and 40 to 75 mole % 1,4-cyclohexanedimethanol; 25 to 55 mole % 2,2,4,4-tetramethyl-1,3-cyclobutanediol and 45 to 75 mole % 1,4-cyclohexanedimethanol; 25 to 50 mole % 2,2,4,4-tetramethyl-1,3-cyclobutanediol and 50 to 75 mole % 1,4-cyclohexanedimethanol; 25 to less than 50 mole % 2,2,4,4-tetramethyl-1,3-cyclobutanediol and greater than 50 to 75 mole % 1,4-cyclohexanedimethanol; 25 to 45 mole % 2,2,4,4-tetramethyl-1,3-cyclobutanediol and 55 to 75 mole % 1,4-cyclohexanedimethanol; 25 to 40 mole % 2,2,4,4-tetramethyl-1,3-cyclobutanediol and 60 to 75 mole % 1,4-cyclohexanedimethanol; 25 to 35 mole % 2,2,4,4-tetramethyl-1,3-cyclobutanediol and 65 to 75 mole % 1,4-cyclohexanedimethanol; and 25 to 30 mole % 2,2,4,4-tetramethyl-1,3-cyclobutanediol and 70 to 75 mole % 1,4-cyclohexanedimethanol.

In other aspects of the invention, the glycol component for the polyesters useful in the invention include but are not limited to at least one of the following combinations of ranges: 30 to 99 mole % 2,2,4,4-tetramethyl-1,3-cyclobutanediol and 1 to 70 mole % 1,4-cyclohexanedimethanol; 30 to 95 mole % 2,2,4,4-tetramethyl-1,3-cyclobutanediol and 5 to 70 mole % 1,4-cyclohexanedimethanol; 30 to 90 mole % 2,2,4,4-tetramethyl-1,3-cyclobutanediol and 10 to 70 mole % 1,4-cyclohexanedimethanol; 30 to 85 mole % 2,2,4,4-tetramethyl-1,3-cyclobutanediol and 15 to 70 mole % 1,4-cyclohexanedimethanol; 30 to 80 mole % 2,2,4,4-tetramethyl-1,3-cyclobutanediol and 20 to 70 mole % 1,4-cyclohexanedimethanol; 30 to 75 mole % 2,2,4,4-tetramethyl-1,3-cyclobutanediol and 25 to 70 mole % 1,4-cyclohexanedimethanol; 30 to 70 mole % 2,2,4,4-tetramethyl-1,3-cyclobutanediol and 30 to 70 mole % 1,4-cyclohexanedimethanol; 30 to 65 mole % 2,2,4,4-tetramethyl-1,3-cyclobutanediol and 35 to 70 mole % 1,4-cyclohexanedimethanol; 30 to 60 mole % 2,2,4,4-tetramethyl-1,3-cyclobutanediol and 40 to 70 mole % 1,4-cyclohexanedimethanol; 30 to 55 mole % 2,2,4,4-tetramethyl-1,3-cyclobutanediol and 45 to 70 mole % 1,4-cyclohexanedimethanol; 30 to 50 mole % 2,2,4,4-tetramethyl-1,3-cyclobutanediol and 50 to 70 mole % 1,4-cyclohexanedimethanol; 30 to less than 50 mole % 2,2,4,4-tetramethyl-1,3-cyclobutanediol and greater than 50 to 70 mole % 1,4-cyclohexanedimethanol; 30 to 45 mole % 2,2,4,4-tetramethyl-1,3-cyclobutanediol and 55 to 70 mole % 1,4-cyclohexanedimethanol; 30 to 40 mole % 2,2,4,4-tetramethyl-1,3-cyclobutanediol and 60 to 70 mole % 1,4-cyclohexanedimethanol; 30 to 35 mole % 2,2,4,4-tetramethyl-1,3-cyclobutanediol and 65 to 70 mole % 1,4-cyclohexanedimethanol.

In other aspects of the invention, the glycol component for the polyesters useful in the invention include but are not limited to at least one of the following combinations of ranges: 35 to 99 mole % 2,2,4,4-tetramethyl-1,3-cyclobutanediol and 1 to 65 mole % 1,4-cyclohexanedimethanol; 35 to 95 mole % 2,2,4,4-tetramethyl-1,3-cyclobutanediol and 5 to 65 mole % 1,4-cyclohexanedimethanol; 35 to 90 mole % 2,2,4,4-tetramethyl-1,3-cyclobutanediol and 10 to 65 mole % 1,4-cyclohexanedimethanol; 35 to 85 mole % 2,2,4,4-tetramethyl-1,3-cyclobutanediol and 15 to 65 mole % 1,4-cyclohexanedimethanol; 35 to 80 mole % 2,2,4,4-tetramethyl-1,3-cyclobutanediol and 20 to 65 mole % 1,4-cyclohexanedimethanol; 35 to 75 mole % 2,2,4,4-tetramethyl-1,3-cyclobutanediol and 25 to 65 mole % 1,4-cyclohexanedimethanol; 35 to 70 mole % 2,2,4,4-tetramethyl-1,3-cyclobutanediol and 30 to 65 mole % 1,4-cyclohexanedimethanol; 35 to 65 mole % 2,2,4,4-tetramethyl-1,3-cyclobutanediol and 35 to 65 mole % 1,4-cyclohexanedimethanol; 35 to 60 mole % 2,2,4,4-tetramethyl-1,3-cyclobutanediol and 40 to 65 mole % 1,4-cyclohexanedimethanol; 35 to 55 mole % 2,2,4,4-tetramethyl-1,3-cyclobutanediol and 45 to 65 mole % 1,4-cyclohexanedimethanol; 35 to 50 mole % 2,2,4,4-tetramethyl-1,3-cyclobutanediol and 50 to 65 mole % 1,4-cyclohexanedimethanol; 35 to less than 50 mole % 2,2,4,4-tetramethyl-1,3-cyclobutanediol and greater than 50 to 65 mole % 1,4-cyclohexanedimethanol; 35 to 45 mole % 2,2,4,4-tetramethyl-1,3-cyclobutanediol and 55 to 65 mole % 1,4-cyclohexanedimethanol; 35 to 40 mole % 2,2,4,4-tetramethyl-1,3-cyclobutanediol and 60 to 65 mole % 1,4-cyclohexanedimethanol.

In other aspects of the invention, the glycol component for the polyesters useful in the invention include but are not limited to at least one of the following combinations of ranges: 40 to 99 mole % 2,2,4,4-tetramethyl-1,3-cyclobutanediol and 1 to 60 mole % 1,4-cyclohexanedimethanol; 40 to 95 mole % 2,2,4,4-tetramethyl-1,3-cyclobutanediol and 5 to 60 mole % 1,4-cyclohexanedimethanol; 40 to 90 mole % 2,2,4,4-tetramethyl-1,3-cyclobutanediol and 10 to 60 mole % 1,4-cyclohexanedimethanol; 40 to 85 mole % 2,2,4,4-tetramethyl-1,3-cyclobutanediol and 15 to 60 mole % 1,4-cyclohexanedimethanol; 40 to 80 mole % 2,2,4,4-tetramethyl-1,3-cyclobutanediol and 20 to 60 mole % 1,4-cyclohexanedimethanol; 40 to 75 mole % 2,2,4,4-tetramethyl-1,3-cyclobutanediol and 25 to 60 mole % 1,4-cyclohexanedimethanol; 40 to 70 mole % 2,2,4,4-tetramethyl-1,3-cyclobutanediol and 30 to 60 mole % 1,4-cyclohexanedimethanol; 40 to 65 mole % 2,2,4,4-tetramethyl-1,3-cyclobutanediol and 35 to 60 mole % 1,4-cyclohexanedimethanol; 40 to 60 mole % 2,2,4,4-tetramethyl-1,3-cyclobutanediol and 40 to 60 mole % 1,4-cyclohexanedimethanol; 40 to 55 mole % 2,2,4,4-tetramethyl-1,3-cyclobutanediol and 45 to 60 mole % 1,4-cyclohexanedimethanol; 40 to less than 50 mole % 2,2,4,4-tetramethyl-1,3-cyclobutanediol and greater than 50 to 60 mole % 1,4-cyclohexanedimethanol; 40 to 50 mole % 2,2,4,4-tetramethyl-1,3-cyclobutanediol and 50 to 60 mole % 1,4-cyclohexanedimethanol; and 40 to 45 mole % 2,2,4,4-tetramethyl-1,3-cyclobutanediol and 55 to 60 mole % 1,4-cyclohexanedimethanol.

In other aspects of the invention, the glycol component for the polyesters useful in the invention include but are not limited to at least one of the following combinations of ranges: 45 to 99 mole % 2,2,4,4-tetramethyl-1,3-cyclobutanediol and 1 to 55 mole % 1,4-cyclohexanedimethanol; 45 to 95 mole % 2,2,4,4-tetramethyl-1,3-cyclobutanediol and 5 to 55 mole % 1,4-cyclohexanedimethanol; 45 to 90 mole % 2,2,4,4-tetramethyl-1,3-cyclobutanediol and 10 to 55 mole % 1,4-cyclohexanedimethanol; 45 to 85 mole % 2,2,4,4-tetramethyl-1,3-cyclobutanediol and 15 to 55 mole % 1,4-cyclohexanedimethanol; 45 to 80 mole % 2,2,4,4-tetramethyl-1,3-cyclobutanediol and 20 to 55 mole % 1,4-cyclohexanedimethanol; 45 to 75 mole % 2,2,4,4-tetramethyl-1,3-cyclobutanediol and 25 to 55 mole % 1,4-cyclohexanedimethanol; 45 to 70 mole % 2,2,4,4-tetramethyl-1,3-cyclobutanediol and 30 to 55 mole % 1,4-cyclohexanedimethanol; 45 to 65 mole % 2,2,4,4-tetramethyl-1,3-cyclobutanediol and 35 to 55 mole % 1,4-cyclohexanedimethanol; 45 to 60 mole % 2,2,4,4-tetramethyl-1,3-cyclobutanediol and 40 to 55 mole % 1,4-cyclohexanedimethanol; greater than 45 to 55 mole % 2,2,4,4-tetramethyl-1,3-cyclobutanediol and 45 to less than 55 mole % 1,4-cyclohexanedimethanol; 45 to 55 mole % 2,2,4,4-tetramethyl-1,3-cyclobutanediol and 45 to 55 mole % 1,4-cyclohexanedimethanol; and 45 to 50 mole % 2,2,4,4-tetramethyl-1,3-cyclobutanediol and 50 to 60 mole % 1,4-cyclohexanedimethanol.

In other aspects of the invention, the glycol component for the polyesters useful in the invention include but are not limited to at least one of the following combinations of ranges: greater than 50 to 99 mole % 2,2,4,4-tetramethyl-1,3-cyclobutanediol and 1 to less than 50 mole % 1,4-cyclohexanedimethanol; greater than 50 to 95 mole % 2,2,4,4-tetramethyl-1,3-cyclobutanediol and 5 to less than 50 mole % 1,4-cyclohexanedimethanol; greater than 50 to 90 mole % 2,2,4,4-tetramethyl-1,3-cyclobutanediol and 10 to less than 50 mole % 1,4-cyclohexanedimethanol; greater than 50 to 85 mole % 2,2,4,4-tetramethyl-1,3-cyclobutanediol and 15 to less than 50 mole % 1,4-cyclohexanedimethanol; greater than 50 to 80 mole % 2,2,4,4-tetramethyl-1,3-cyclobutanediol and 20 to less than 50 mole % 1,4-cyclohexanedimethanol; greater than 50 to 75 mole % 2,2,4,4-tetramethyl-1,3-cyclobutanediol and 25 to less than 50 mole % 1,4-cyclohexanedimethanol; greater than 50 to 70 mole % 2,2,4,4-tetramethyl-1,3-cyclobutanediol and 30 to less than 50 mole % 1,4-cyclohexanedimethanol; greater than 50 to 65 mole % 2,2,4,4-tetramethyl-1,3-cyclobutanediol and 35 to less than 50 mole % 1,4-cyclohexanedimethanol; greater than 50 to 60 mole % 2,2,4,4-tetramethyl-1,3-cyclobutanediol and 40 to less than 50 mole % 1,4-cyclohexanedimethanol.

In other aspects of the invention, the glycol component for the polyesters useful in the invention include but are not limited to at least one of the following combinations of ranges: 55 to 99 mole % 2,2,4,4-tetramethyl-1,3-cyclobutanediol and 1 to 45 mole % 1,4-cyclohexanedimethanol; 55 to 95 mole % 2,2,4,4-tetramethyl-1,3-cyclobutanediol and 5 to 45 mole % 1,4-cyclohexanedimethanol; 55 to 90 mole % 2,2,4,4-tetramethyl-1,3-cyclobutanediol and 10 to 45 mole % 1,4-cyclohexanedimethanol; 55 to 85 mole % 2,2,4,4-tetramethyl-1,3-cyclobutanediol and 15 to 45 mole % 1,4-cyclohexanedimethanol; 55 to 80 mole % 2,2,4,4-tetramethyl-1,3-cyclobutanediol and 20 to 45 mole % 1,4-cyclohexanedimethanol; 55 to 75 mole % 2,2,4,4-tetramethyl-1,3-cyclobutanediol and 25 to 45 mole % 1,4-cyclohexanedimethanol; 55 to 70 mole % 2,2,4,4-tetramethyl-1,3-cyclobutanediol and 30 to 45 mole % 1,4-cyclohexanedimethanol; 55 to 65 mole % 2,2,4,4-tetramethyl-1,3-cyclobutanediol and 35 to 45 mole % 1,4-cyclohexanedimethanol; and 55 to 60 mole % 2,2,4,4-tetramethyl-1,3-cyclobutanediol and 40 to 45 mole % 1,4-cyclohexanedimethanol.

In other aspects of the invention, the glycol component for the polyesters useful in the invention include but are not limited to at least one of the following combinations of ranges: 60 to 99 mole % 2,2,4,4-tetramethyl-1,3-cyclobutanediol and 1 to 40 mole % 1,4-cyclohexanedimethanol; 60 to 95 mole % 2,2,4,4-tetramethyl-1,3-cyclobutanediol and 5 to 40 mole % 1,4-cyclohexanedimethanol; 60 to 90 mole % 2,2,4,4-tetramethyl-1,3-cyclobutanediol and 10 to 40 mole % 1,4-cyclohexanedimethanol; 60 to 85 mole % 2,2,4,4-tetramethyl-1,3-cyclobutanediol and 15 to 40 mole % 1,4-cyclohexanedimethanol; 60 to 80 mole % 2,2,4,4-tetramethyl-1,3-cyclobutanediol and 20 to 40 mole % 1,4-cyclohexanedimethanol; 60 to 75 mole % 2,2,4,4-tetramethyl-1,3-cyclobutanediol and 25 to 40 mole % 1,4-cyclohexanedimethanol; and 60 to 70 mole % 2,2,4,4-tetramethyl-1,3-cyclobutanediol and 30 to 40 mole % 1,4-cyclohexanedimethanol.

In other aspects of the invention, the glycol component for the polyesters useful in the invention include but are not limited to at least one of the following combinations of ranges: 65 to 99 mole % 2,2,4,4-tetramethyl-1,3-cyclobutanediol and 1 to 35 mole % 1,4-cyclohexanedimethanol; 65 to 95 mole % 2,2,4,4-tetramethyl-1,3-cyclobutanediol and 5 to 35 mole % 1,4-cyclohexanedimethanol; 65 to 90 mole % 2,2,4,4-tetramethyl-1,3-cyclobutanediol and 10 to 35 mole % 1,4-cyclohexanedimethanol; 65 to 85 mole % 2,2,4,4-tetramethyl-1,3-cyclobutanediol and 15 to 35 mole % 1,4-cyclohexanedimethanol; 65 to 80 mole % 2,2,4,4-tetramethyl-1,3-cyclobutanediol and 20 to 35 mole % 1,4-cyclohexanedimethanol; 65 to 75 mole % 2,2,4,4-tetramethyl-1,3-cyclobutanediol and 25 to 35 mole % 1,4-cyclohexanedimethanol; and 65 to 70 mole % 2,2,4,4-tetramethyl-1,3-cyclobutanediol and 35 to 40 mole % 1,4-cyclohexanedimethanol.

In other aspects of the invention, the glycol component for the polyesters useful in the invention include but are not limited to at least one of the following combinations of ranges: 70 to 99 mole % 2,2,4,4-tetramethyl-1,3-cyclobutanediol and 1 to 30 mole % 1,4-cyclohexanedimethanol; 70 to 95 mole % 2,2,4,4-tetramethyl-1,3-cyclobutanediol and 5 to 30 mole % 1,4-cyclohexanedimethanol; 70 to 90 mole % 2,2,4,4-tetramethyl-1,3-cyclobutanediol and 10 to 30 mole % 1,4-cyclohexanedimethanol; 70 to 85 mole % 2,2,4,4-tetramethyl-1,3-cyclobutanediol and 15 to 30 mole % 1,4-cyclohexanedimethanol; 70 to 80 mole % 2,2,4,4-tetramethyl-1,3-cyclobutanediol and 20 to 30 mole % 1,4-cyclohexanedimethanol; 70 to 75 mole % 2,2,4,4-tetramethyl-1,3-cyclobutanediol and 25 to 30 mole % 1,4-cyclohexanedimethanol.

In other aspects of the invention, the glycol component for the polyesters useful in the invention include but are not limited to at least one of the following combinations of ranges: 75 to 99 mole % 2,2,4,4-tetramethyl-1,3-cyclobutanediol and 1 to 25 mole % 1,4-cyclohexanedimethanol; 75 to 95 mole % 2,2,4,4-tetramethyl-1,3-cyclobutanediol and 5 to 25 mole % 1,4-cyclohexanedimethanol; 75 to 90 mole % 2,2,4,4-tetramethyl-1,3-cyclobutanediol and 10 to 25 mole % 1,4-cyclohexanedimethanol; and 75 to 85 mole % 2,2,4,4-tetramethyl-1,3-cyclobutanediol and 15 to 25 mole % 1,4-cyclohexanedimethanol.

In other aspects of the invention, the glycol component for the polyesters useful in the invention include but are not limited to at least one of the following combinations of ranges: 80 to 99 mole % 2,2,4,4-tetramethyl-1,3-cyclobutanediol and 1 to 20 mole % 1,4-cyclohexanedimethanol; 80 to 95 mole % 2,2,4,4-tetramethyl-1,3-cyclobutanediol and 5 to 20 mole % 1,4-cyclohexanedimethanol; 80 to 90 mole % 2,2,4,4-tetramethyl-1,3-cyclobutanediol and 10 to 20 mole % 1,4-cyclohexanedimethanol.

In other aspects of the invention, the glycol component for the polyesters useful in the invention include but are not limited to at least one of the following combinations of ranges 37 to 80 mole % 2,2,4,4-tetramethyl-1,3-cyclobutanediol and 20 to 63 mole % 1,4-cyclohexanedimethanol; 40 to less than 45 mole % 2,2,4,4-tetramethyl-1,3-cyclobutanediol and greater than 55 to 60 mole % 1,4-cyclohexanedimethanol; greater than 45 to 55 mole % 2,2,4,4-tetramethyl-1,3-cyclobutanediol and 45 to less than 55 mole % 1,4-cyclohexanedimethanol; and 46 to 55 mole % 2,2,4,4-tetramethyl-1,3-cyclobutanediol and 45 to 54 mole % 1,4-cyclohexanedimethanol; and 46 to 65 mole % 2,2,4,4-tetramethyl-1,3-cyclobutanediol and 35 to 54 mole % 1,4-cyclohexanedimethanol.

In other aspects of the invention where the mole percent of 2,2,4,4-tetramethyl-1,3-cyclobutanediol is present at 0.01 to less than 5 mole % based on the mole percentages for the diol component equaling 100 mole % and where the presence of CHDM is optional, the glycol component for the polyesters useful the invention include but are not limited to at least of the following combinations of ranges: 0.01 to less than 5 mole % of 2,2,4,4-tetramethyl-1,3-cyclobutanediol residues, greater than 0.01 to 95 mole % of ethylene glycol residues, and 0 to 99.98 mole % of 1,4-cyclohexanedimethanol; 0.01 to less than 5 mole % of 2,2,4,4-tetramethyl-1,3-cyclobutanediol residues, greater than 0.01 to 94.99 mole % of ethylene glycol residues, and 0.01 to 99.98 mole % of 1,4-cyclohexanedimethanol; 0.01 to less than 5 mole % of 2,2,4,4-tetramethyl-1,3-cyclobutanediol residues, greater than 0.01 to 90 mole % of ethylene glycol residues, and 5 to 99.98 mole % of 1,4-cyclohexanedimethanol; 0.01 to less than 5 mole % of 2,2,4,4-tetramethyl-1,3-cyclobutanediol residues, greater than 0.01 to 85 mole % of ethylene glycol residues, and 10 to 99.98 mole % of 1,4-cyclohexanedimethanol; 0.01 to less than 5 mole % of 2,2,4,4-tetramethyl-1,3-cyclobutanediol residues, greater than 0.01 to 80 mole % of ethylene glycol residues, and 15 to 99.98 mole % of 1,4-cyclohexanedimethanol; 0.01 to less than 5 mole % of 2,2,4,4-tetramethyl-1,3-cyclobutanediol residues, greater than 0.01 to 75 mole % of ethylene glycol residues, and 20 to 99.98 mole % of 1,4-cyclohexanedimethanol; 0.01 to less than 5 mole % of 2,2,4,4-tetramethyl-1,3-cyclobutanediol residues, greater than 0.01 to 70 mole % of ethylene glycol residues, and 25 to 99.98 mole % of 1,4-cyclohexanedimethanol; greater than 0.01 to 65 mole % of ethylene glycol residues, and 30 to 99.98 mole % of 1,4-cyclohexanedimethanol; 0.01 to less than 5 mole % of 2,2,4,4-tetramethyl-1,3-cyclobutanediol residues, greater than 0.01 to 60 mole % of ethylene glycol residues, and 35 to 99.98 mole % of 1,4-cyclohexanedimethanol; 0.01 to less than 5 mole % of 2,2,4,4-tetramethyl-1,3-cyclobutanediol residues, greater than 0.01 to 55 mole % of ethylene glycol residues, and 40 to 99.98 mole % of 1,4-cyclohexanedimethanol; 0.01 to less than 5 mole % of 2,2,4,4-tetramethyl-1,3-cyclobutanediol residues, greater than 0.01 to 50 mole % of ethylene glycol residues, and 45 to 99.98 mole % of 1,4-cyclohexanedimethanol; 0.01 to less than 5 mole % of 2,2,4,4-tetramethyl-1,3-cyclobutanediol residues, greater than 0.01 to 45 mole % of ethylene glycol residues, and 50 to 99.98 mole % of 1,4-cyclohexanedimethanol; 0.01 to less 5 mole % of 2,2,4,4-tetramethyl-1,3-cyclobutanediol residues, greater than 0.01 to 40 mole % of ethylene glycol residues, and 55 to 99.98 mole % of 1,4-cyclohexanedimethanol; 0.01 to less than 5 mole % of 2,2,4,4-tetramethyl-1,3-cyclobutanediol residues, greater than 0.01 to 35 mole % of ethylene glycol residues, and 60 to 99.98 mole % of 1,4-cyclohexanedimethanol; 0.01 to less than 5 mole % of 2,2,4,4-tetramethyl-1,3-cyclobutanediol residues, greater than 0.01 to 30 mole % of ethylene glycol residues, and 65 to 99.98 mole % of 1,4-cyclohexanedimethanol; 0.01 to less than 5 mole % of 2,2,4,4-tetramethyl-1,3-cyclobutanediol residues, greater than 0.01 to 25 mole % of ethylene glycol residues, and 70 to 99.98 mole % of 1,4-cyclohexanedimethanol; 0.01 to less than 5 mole % of 2,2,4,4-tetramethyl-1,3-cyclobutanediol residues, greater than 0.01 to 20 mole % of ethylene glycol residues, and 75 to 99.98 mole % of 1,4-cyclohexanedimethanol; 0.01 to less than 5 mole % of 2,2,4,4-tetramethyl-1,3-cyclobutanediol residues, greater than 0.01 to 15 mole % of ethylene glycol residues, and 80 to 99.98 mole % of 1,4-cyclohexanedimethanol; 0.01 to less than 5 mole % of 2,2,4,4-tetramethyl-1,3-cyclobutanediol residues, greater than 0.01 to 10 mole % of ethylene glycol residues, and 85 to 99.98 mole % of 1,4-cyclohexanedimethanol; 0.01 to less than 5 mole % of 2,2,4,4-tetramethyl-1,3-cyclobutanediol residues, greater than 0.01 to 5 mole % of ethylene glycol residues, and 90 to 99.98 mole % of 1,4-cyclohexanedimethanol; 0.01 to less than 5 mole % of 2,2,4,4-tetramethyl-1,3-cyclobutanediol residues, and greater than 0.01 to 5 mole % of ethylene glycol residues, and 90 to 99.98 mole % of 1,4-cyclohexanedimethanol.

The glycol component may also contain one of the following ranges of 2,2,4,4-tetramethyl-1,3-cyclobutanediol residues: 0.01 to 4.5 mole %; 0.01 to 4 mole %; 0.01 to 3.5 mole %; 0.01 to 3 mole %; 0.01 to 2.5 mole %; 0.01 to 2.0 mole %; 0.01 to 2.5 mole %; 0.01 to 2 mole %; 0.01 to 1.5 mole %; 0.01 to 1.0 mole %; and 0.01 to 0.5 mole %. The remainder of the glycol component can be any amount of 1,4-cyclohexanedimethanol and/or ethylene glycol so long as the total amount of the glycol component equals 100 mole %.

In addition to the diols set forth above, the polyesters useful in the polyester compositions useful in the invention may be made from 1,3-propanediol, 1,4-butanediol, or mixtures thereof. It is contemplated that compositions of the invention made from 1,3-propanediol, 1,4-butanediol, or mixtures thereof can possess at least one of the Tg ranges described herein, at least one of the inherent viscosity ranges described herein, and/or at least one of the glycol or diacid ranges described herein. In addition or in the alternative, the polyesters made from 1,3-propanediol or 1,4-butanediol or mixtures thereof may also be made from 1,4-cyclohexanedmethanol in at least one of the following amounts: from 0.1 to 99 mole %; 0.1 to 90 mole %; from 0.1 to 80 mole %; from 0.1 to 70 mole %; from 0.1 to 60 mole %; from 0.1 to 50 mole %; from 0.1 to 40 mole %; from 0.1 to 35 mole %; from 0.1 to 30 mole %; from 0.1 to 25 mole %; from 0.1 to 20 mole %; from 0.1 to 15 mole %; from 0.1 to 10 mole %; from 0.1 to 5 mole %; from 1 to 99 mole %; from 1 to 90 mole %; from 1 to 80 mole %; from 1 to 70 mole %; from 1 to 60 mole %; from 1 to 50 mole %; from 1 to 40 mole %; from 1 to 35 mole %; from 1 to 30 mole %; from 1 to 25 mole %; from 1 to 20 mole %; from 1 to 15 mole %; from 1 to 10 mole %; from 1 to 5 mole %; from 5 to 80 mole %; 5 to 70 mole %; from 5 to 60 mole %; from 5 to 50 mole %; from 5 to 40 mole %; from 5 to 35 mole %; from 5 to 30 mole %; from 5 to 25 mole %; from 5 to 20 mole %; and from 5 to 15 mole %; from 5 to 10 mole %; from 10 to 99 mole %; from 10 to 90 mole %; from 10 to 80 mole %; from 10 to 70 mole %; from 10 to 60 mole %; from 10 to 50 mole %; from 10 to 40 mole %; from 10 to 35 mole %; from 10 to 30 mole %; from 10 to 25 mole %; from 10 to 20 mole %; from 10 to 15 mole %; from 20 to 99 mole %; 20 to 95 mole %; from 20 to 80 mole %; from 20 to 70 mole %; from 20 to 60 mole %; from 20 to 50 mole %; from 20 to 40 mole %; from 20 to 35 mole %; from 20 to 30 mole %; and from 20 to 25 mole %.

For embodiments of the invention, the polyesters useful in the invention may exhibit at least one of the following inherent viscosities as determined in 60/40 (wt/wt) phenol/tetrachloroethane at a concentration of 0.5 g/100 ml at 25° C.: 0.10 to 1.2 dL/g; 0.10 to 1.1 dL/g; 0.10 to 1 dL/g; 0.10 to less than 1 dL/g; 0.10 to 0.98 dL/g; 0.10 to 0.95 dL/g; 0.10 to 0.90 dL/g; 0.10 to 0.85 dL/g; 0.10 to 0.80 dL/g; 0.10 to 0.75 dL/g; 0.10 to less than 0.75 dL/g; 0.10 to 0.72 dL/g; 0.10 to 0.70 dL/g; 0.10 to less than 0.70 dL/g; 0.10 to 0.68 dL/g; 0.10 to less than 0.68 dL/g; 0.10 to 0.65 dL/g; 0.10 to 0.6 dL/g; 0.10 to 0.55 dL/g; 0.10 to 0.5 dL/g; 0.10 to 0.4 dL/g; 0.10 to 0.35 dL/g; 0.20 to 1.2 dL/g; 0.20 to 1.1 dL/g; 0.20 to 1 dL/g; 0.20 to less than 1 dL/g; 0.20 to 0.98 dL/g; 0.20 to 0.95 dL/g; 0.20 to 0.90 dL/g; 0.20 to 0.85 dL/g; 0.20 to 0.80 dL/g; 0.20 to 0.75 dL/g; 0.20 to less than 0.75 dL/g; 0.20 to 0.72 dL/g; 0.20 to 0.70 dL/g; 0.20 to less than 0.70 dL/g; 0.20 to 0.68 dL/g; 0.20 to less than 0.68 dL/g; 0.20 to 0.65 dL/g; 0.20 to 0.6 dL/g; 0.20 to 0.55 dL/g; 0.20 to 0.5 dL/g; 0.20 to 0.4 dL/g; 0.20 to 0.35 dL/g; 0.35 to 1.2 dL/g; 0.35 to 1.1 dL/g; 0.35 to 1 dL/g; 0.35 to less than 1 dL/g; 0.35 to 0.98 dL/g; 0.35 to 0.95 dL/g; 0.35 to 0.90 dL/g; 0.35 to 0.85 dL/g; 0.35 to 0.80 dL/g; 0.35 to 0.75 dL/g; 0.35 to less than 0.75 dL/g; 0.35 to 0.72 dL/g; 0.35 to 0.70 dL/g; 0.35 to less than 0.70 dL/g; 0.35 to 0.68 dL/g; 0.35 to less than 0.68 dL/g; 0.35 to 0.65 dL/g; 0.40 to 1.2 dL/g; 0.40 to 1.1 dL/g; 0.40 to 1 dL/g; 0.40 to less than 1 dL/g; 0.40 to 0.98 dL/g; 0.40 to 0.95 dL/g; 0.40 to 0.90 dL/g; 0.40 to 0.85 dL/g; 0.40 to 0.80 dL/g; 0.40 to 0.75 dL/g; 0.40 to less than 0.75 dL/g; 0.40 to 0.72 dL/g; 0.40 to 0.70 dL/g; 0.40 to less than 0.70 dL/g; 0.40 to 0.68 dL/g; 0.40 to less than 0.68 dL/g; 0.40 to 0.65 dL/g; greater than 0.42 to 1.2 dL/g; greater than 0.42 to 1.1 dL/g; greater than 0.42 to 1 dL/g; greater than 0.42 to less than 1 dL/g; greater than 0.42 to 0.98 dL/g; greater than 0.42 to 0.95 dL/g; greater than 0.42 to 0.90 dL/g; greater than 0.42 to 0.85 dL/g; greater than 0.42 to 0.80 dL/g; greater than 0.42 to 0.75 dL/g; greater than 0.42 to less than 0.75 dL/g; greater than 0.42 to 0.72 dL/g; greater than 0.42 to 0.70 dL/g; greater than 0.42 to less than 0.70 dL/g; greater than 0.42 to 0.68 dL/g; greater than 0.42 to less than 0.68 dL/g; and greater than 0.42 to 0.65 dL/g.

For embodiments of the invention, the polyesters useful in the invention may exhibit at least one of the following inherent viscosities as determined in 60/40 (wt/wt) phenol/tetrachloroethane at a concentration of 0.5 g/100 ml at 25° C.: 0.45 to 1.2 dL/g; 0.45 to 1.1 dL/g; 0.45 to 1 dL/g; 0.45 to 0.98 dL/g; 0.45 to 0.95 dL/g; 0.45 to 0.90 dL/g; 0.45 to 0.85 dL/g; 0.45 to 0.80 dL/g; 0.45 to 0.75 dL/g; 0.45 to less than 0.75 dL/g; 0.45 to 0.72 dL/g; 0.45 to 0.70 dL/g; 0.45 to less than 0.70 dL/g; 0.45 to 0.68 dL/g; 0.45 to less than 0.68 dL/g; 0.45 to 0.65 dL/g; 0.50 to 1.2 dL/g; 0.50 to 1.1 dL/g; 0.50 to 1 dL/g; 0.50 to less than 1 dL/g; 0.50 to 0.98 dL/g; 0.50 to 0.95 dL/g; 0.50 to 0.90 dL/g; 0.50 to 0.85 dL/g; 0.50 to 0.80 dL/g; 0.50 to 0.75 dL/g; 0.50 to less than 0.75 dL/g; 0.50 to 0.72 dL/g; 0.50 to 0.70 dL/g; 0.50 to less than 0.70 dL/g; 0.50 to 0.68 dL/g; 0.50 to less than 0.68 dL/g; 0.50 to 0.65 dL/g; 0.55 to 1.2 dL/g; 0.55 to 1.1 dL/g; 0.55 to 1 dL/g; 0.55 to less than 1 dL/g; 0.55 to 0.98 dL/g; 0.55 to 0.95 dL/g; 0.55 to 0.90 dL/g; 0.55 to 0.85 dL/g; 0.55 to 0.80 dL/g; 0.55 to 0.75 dL/g; 0.55 to less than 0.75 dL/g; 0.55 to 0.72 dL/g; 0.55 to 0.70 dL/g; 0.55 to less than 0.70 dL/g; 0.55 to 0.68 dL/g; 0.55 to less than 0.68 dL/g; 0.55 to 0.65 dL/g; 0.58 to 1.2 dL/g; 0.58 to 1.1 dL/g; 0.58 to 1 dL/g; 0.58 to less than 1 dL/g; 0.58 to 0.98 dL/g; 0.58 to 0.95 dL/g; 0.58 to 0.90 dL/g; 0.58 to 0.85 dL/g; 0.58 to 0.80 dL/g; 0.58 to 0.75 dL/g; 0.58 to less than 0.75 dL/g; 0.58 to 0.72 dL/g; 0.58 to 0.70 dL/g; 0.58 to less than 0.70 dL/g; 0.58 to 0.68 dL/g; 0.58 to less than 0.68 dL/g; 0.58 to 0.65 dL/g; 0.60 to 1.2 dL/g; 0.60 to 1.1 dL/g; 0.60 to 1 dL/g; 0.60 to less than 1 dL/g; 0.60 to 0.98 dL/g; 0.60 to 0.95 dL/g; 0.60 to 0.90 dL/g; 0.60 to 0.85 dL/g; 0.60 to 0.80 dL/g; 0.60 to 0.75 dL/g; 0.60 to less than 0.75 dL/g; 0.60 to 0.72 dL/g; 0.60 to 0.70 dL/g; 0.60 to less than 0.70 dL/g; 0.60 to 0.68 dL/g; 0.60 to less than 0.68 dL/g; 0.60 to 0.65 dL/g; 0.65 to 1.2 dL/g; 0.65 to 1.1 dL/g; 0.65 to 1 dL/g; 0.65 to less than 1 dL/g; 0.65 to 0.98 dL/g; 0.65 to 0.95 dL/g; 0.65 to 0.90 dL/g; 0.65 to 0.85 dL/g; 0.65 to 0.80 dL/g; 0.65 to 0.75 dL/g; 0.65 to less than 0.75 dL/g; 0.65 to 0.72 dL/g; 0.65 to 0.70 dL/g; 0.65 to less than 0.70 dL/g; 0.68 to 1.2 dL/g; 0.68 to 1.1 dL/g; 0.68 to 1 dL/g; 0.68 to less than 1 dL/g; 0.68 to 0.98 dL/g; 0.68 to 0.95 dL/g; 0.68 to 0.90 dL/g; 0.68 to 0.85 dL/g; 0.68 to 0.80 dL/g; 0.68 to 0.75 dL/g; 0.68 to less than 0.75 dL/g; 0.68 to 0.72 dL/g; greater than 0.76 dL/g to 1.2 dL/g; greater than 0.76 dL/g to 1.1 dL/g; greater than 0.76 dL/g to 1 dL/g; greater than 0.76 dL/g to less than 1 dL/g; greater than 0.76 dL/g to 0.98 dL/g; greater than 0.76 dL/g to 0.95 dL/g; greater than 0.76 dL/g to 0.90 dL/g; greater than 0.80 dL/g to 1.2 dL/g; greater than 0.80 dL/g to 1.1 dL/g; greater than 0.80 dL/g to 1 dL/g; greater than 0.80 dL/g to less than 1 dL/g; greater than 0.80 dL/g to 1.2 dL/g; greater than 0.80 dL/g to 0.98 dL/g; greater than 0.80 dL/g to 0.95 dL/g; greater than 0.80 dL/g to 0.90 dL/g.

For the desired polyester, the molar ratio of cis/trans 2,2,4,4-tetramethyl-1,3-cyclobutanediol can vary from the pure form of each or mixtures thereof. In certain embodiments, the molar percentages for cis and/or trans 2,2,4,4,-tetramethyl-1,3-cyclobutanediol are greater than 50 mole % cis and less than 50 mole % trans and are selected from at least one of the following ranges: 50.01 to 99 mole % cis and 1 to 49.99 mole % trans, 51 to 99 mole % cis and 1 to 49 mole % trans; greater than 55 to 99 mole % cis and 1 to less than 45 mole % trans; 55 to 99 cis and 1 to 45 mole % trans; 60 to 99 mole % cis and 1 to 40 mole % trans; 65 to 99 mole % cis and 1 to 35 mole % trans; 70 to 99 mole % cis and 1 to 30 mole % trans; greater than 70 to 99 mole % cis and 1 to less than 30 mole % trans; 75 to 99 mole % cis and 1 to 25 mole % trans; 80 to 99 mole % cis and 1 to 20 mole % trans; 85 to 99 mole % cis and 1 to 15 mole % trans; 90 to 99 mole % cis and 1 to 10 mole % trans; 50.01 to 95 mole % cis and 5 to 49.99 mole % trans, 51 to 95 mole % cis and 5 to 49 mole % trans; greater than 55 to 95 mole % cis and 5 to less than 45 mole % trans; 55 to 95 cis and 5 to 45 mole % trans; 60 to 95 mole % cis and 5 to 40 mole % trans; 65 to 95 mole % cis and 5 to 35 mole % trans; 70 to 95 mole % cis and 5 to 40 mole % trans; 75 to 95 mole % cis and 5 to 25 mole % trans; 80 to 95 mole % cis and 5 to 20 mole % trans; 85 to 95 mole % cis and 5 to 15 mole % trans; 90 to 95 mole % cis and 5 to 10 mole % trans; 95 to 99 mole % trans and 1 to 5 mole % trans; 50.01 to 80 mole % cis and 20 to 49.99 mole % trans; 51 to 80 mole % cis and 20 to 49 mole % trans; greater than 55 to 80 mole % cis and 20 to less than 45 mole % trans; 55 to 80 cis and 20 to 45 mole % trans; 60 to 80 mole % cis and 20 to 40 mole % trans; 65 to 80 mole % cis and 20 to 35 mole % trans; 70 to 80 mole % cis and 20 to 30 mole % trans; greater than 70 to 80 mole % cis and 10 to less than 20 mole % trans; 75 to 80 mole % cis and 20 to 25 mole % trans; 50.01 to 75 mole % cis and 25 to 49.99 mole % trans, 51 to 75 mole % cis and 25 to 49 mole % trans; greater than 55 to 75 mole % cis and 25 to less than 45 mole % trans; 55 to 75 cis and 25 to 45 mole % trans; 60 to 75 mole % cis and 25 to 40 mole % trans; 65 to 75 mole % cis and 25 to 35 mole % trans; 70 to 75 mole % cis and 25 to 30 mole % trans. to 49 mole % trans; greater than 55 to 70 mole % cis and 30 to less than 45 mole % trans; 55 to 70 mole % cis and 30 to 45 mole % trans; 60 to 70 mole % cis and 30 to 40 mole % trans; and 65 to 70 mole % cis and 25 to 30 mole % trans. The molar ratio of cis/trans 1,4-cyclohexandimethanol can vary within the range of 50/50 to 0/100, for example, between 40/60 to 20/80.

It is contemplated that compositions useful in the invention can possess at least one of the inherent viscosity ranges described herein and at least one of the monomer ranges for the compositions described herein unless otherwise stated. It is also contemplated that compositions useful in the invention can possess at least one of the Tg ranges described herein and at least one of the monomer ranges for the compositions described herein unless otherwise stated. It is also contemplated that compositions useful in the invention can possess at least one of the inherent viscosity ranges described herein, at least one of the Tg ranges described herein, and at least one of the monomer ranges for the compositions described herein unless otherwise stated.

In certain embodiments, terephthalic acid residues or an ester thereof, such as, for example, dimethyl terephthalate or a mixture of terephthalic acid residues and an ester thereof can make up a portion or all of the dicarboxylic acid component used to form the polyesters useful in the invention. In certain embodiments, terephthalic acid residues can make up a portion or all of the dicarboxylic acid component used to form the present polyester at a concentration of at least 70 mole %, such as at least 80 mole %, at least 90 mole % at least 95 mole %, at least 99 mole %, or even 100 mole %. In certain embodiments, higher amounts of terephthalic acid can be used in order to produce a higher impact strength polyester. For purposes of this disclosure, the terms “terephthalic acid” and “dimethyl terephthalate” are used interchangeably herein. In one embodiment, dimethyl terephthalate is part or all of the dicarboxylic acid component used to make the polyesters useful in the present invention. For the purposes of this disclosure, the terms: “terephthalic acid” and “dimethyl terephthalate” are used interchangeably herein. In all embodiments, ranges of from 70 to 100 mole %; or 80 to 100 mole %; or 90 to 100 mole %; or 99 to 100 mole %; or 100 mole % terephthalic acid and/or dimethyl terephthalate and/or mixtures thereof may be used.

In addition to terephthalic acid, the dicarboxylic acid component of the polyester useful in the invention can comprise up to 30 mole %, up to 20 mole %, up to 10 mole %, up to 5 mole %, or up to 1 mole % of one or more modifying aromatic dicarboxylic acids. Yet another embodiment contains 0 mole % modifying aromatic dicarboxylic acids. Thus, if present, it is contemplated that the amount of one or more modifying aromatic dicarboxylic acids can range from any of these preceding endpoint values including, for example, from 0.01 to 30 mole %, 0.01 to 20 mole %, from 0.01 to 10 mole %, from 0.01 to 5 mole % and from 0.01 to 1 mole. In one embodiment, modifying aromatic dicarboxylic acids that may be used in the present invention include but are not limited to those having up to 20 carbon atoms, and which can be linear, para-oriented, or symmetrical. Examples of modifying aromatic dicarboxylic acids which may be used in this invention include, but are not limited to, isophthalic acid, 4,4'-biphenyldicarboxylic acid, 1,4-, 1,5-, 2,6-, 2,7-naphthalenedicarboxylic acid, and trans-4,4'-stilbenedicarboxylic acid, and esters thereof. In one embodiment, the modifying aromatic dicarboxylic acid is isophthalic acid.

The carboxylic acid component of the polyesters useful in the invention can be further modified with up to 10 mole %, such as up to 5 mole % or up to 1 mole % of one or more aliphatic dicarboxylic acids containing 2-16 carbon atoms, such as, for example, malonic, succinic, glutaric, adipic, pimelic, suberic, azelaic and dodecanedioic dicarboxylic acids. Certain embodiments can also comprise 0.01 or more mole %, such as 0.1 or more mole %, 1 or more mole %, 5 or more mole %, or 10 or more mole % of one or more modifying aliphatic dicarboxylic acids. Yet another embodiment contains 0 mole % modifying aliphatic dicarboxylic acids. Thus, if present, it is contemplated that the amount of one or more modifying aliphatic dicarboxylic acids can range from any of these preceding endpoint values including, for example, from 0.01 to 10 mole % and from 0.1 to 10 mole %. The total mole % of the dicarboxylic acid component is 100 mole %.

Esters of terephthalic acid and the other modifying dicarboxylic acids or their corresponding esters and/or salts may be used instead of the dicarboxylic acids. Suitable examples of dicarboxylic acid esters include, but are not limited to, the dimethyl, diethyl, dipropyl, diisopropyl, dibutyl, and diphenyl esters. In one embodiment, the esters are chosen from at least one of the following: methyl, ethyl, propyl, isopropyl, and phenyl esters.

The 1,4-cyclohexanedimethanol may be cis, trans, or a mixture thereof, for example, a cis/trans ratio of 60:40 to 40:60. In another embodiment, the trans-1,4-cyclohexanedimethanol can be present in an amount of 60 to 80 mole %.

The glycol component of the polyester portion of the polyester composition useful in the invention can contain 25 mole % or less of one or more modifying glycols which are not 2,2,4,4-tetramethyl-1,3-cyclobutanediol or 1,4-cyclohexanedimethanol; in one embodiment, the polyesters useful in the invention may contain less than 15 mole % of one or more modifying glycols. In another embodiment, the polyesters useful in the invention can contain 10 mole % or less of one or more modifying glycols. In another embodiment, the polyesters useful in the invention can contain 5 mole % or less of one or more modifying glycols. In another embodiment, the polyesters useful in the invention can contain 3 mole % or less of one or more modifying glycols. In another embodiment, the polyesters useful in the invention can contain 0 mole % modifying glycols. Certain embodiments can also contain 0.01 or more mole %, such as 0.1 or more mole %, 1 or more mole %, 5 or more mole %, or 10 or more mole % of one or more modifying glycols. Thus, if present, it is contemplated that the amount of one or more modifying glycols can range from any of these preceding endpoint values including, for example, from 0.01 to 15 mole % and from 0.1 to 10 mole %.

Modifying glycols useful in the polyesters useful in the invention refer to diols other than 2,2,4,4-tetramethyl-1,3-cyclobutanediol and 1,4-cyclohexanedimethanol and can contain 2 to 16 carbon atoms. Examples of suitable modifying glycols include, but are not limited to, ethylene glycol, diethylene glycol, 1,2-propanediol, 1,3-propanediol, neopentyl glycol, 1,4-butanediol, 1,5-pentanediol, 1,6-hexanediol, p-xylene glycol, or mixtures thereof. In one embodiment, the modifying glycol is ethylene glycol. In another embodiment, the modifying glycols include, but are not limited to, 1,3-propanediol and 1,4-butanediol. In another embodiment, ethylene glycol is excluded as a modifying diol. In another embodiment, 1,3-propanediol and 1,4-butanediol are excluded as modifying diols. In another embodiment, 2,2-dimethyl-1,3-propanediol is excluded as a modifying diol.

The polyesters and/or the polycarbonates useful in the polyesters compositions of the invention can comprise from 0 to 10 mole percent, for example, from 0.01 to 5 mole percent, from 0.01 to 1 mole percent, from 0.05 to 5 mole percent, from 0.05 to 1 mole percent, or from 0.1 to 0.7 mole percent, or from 0.1 to 0.5 mole percent based the total mole percentages of either the diol or diacid residues; respectively, of one or more residues of a branching monomer, also referred to herein as a branching agent, having 3 or more carboxyl substituents, hydroxyl substituents, or a combination thereof. In certain embodiments, the branching monomer or agent may be added prior to and/or during and/or after the polymerization of the polyester. The polyester(s) useful in the invention can thus be linear or branched. The polycarbonate can also be linear or branched. In certain embodiments, the branching monomer or agent may be added prior to and/or during and/or after the polymerization of the polycarbonate.

Examples of branching monomers include, but are not limited to, multifunctional acids or multifunctional alcohols such as trimellitic acid, trimellitic anhydride, pyromellitic dianhydride, trimethylolpropane, glycerol, pentaerythritol, citric acid, tartaric acid, 3-hydroxyglutaric acid and the like. In one embodiment, the branching monomer residues can comprise 0.1 to 0.7 mole percent of one or more residues chosen from at least one of the following: trimellitic anhydride, pyromellitic dianhydride, glycerol, sorbitol, 1,2,6-hexanetriol, pentaerythritol, trimethylolethane, and/or trimesic acid. The branching monomer may be added to the polyester reaction mixture or blended with the polyester in the form of a concentrate as described, for example, in U.S. Pat. Nos. 5,654,347 and 5,696,176, whose disclosure regarding branching monomers is incorporated herein by reference.

The glass transition temperature (Tg) of the polyesters useful in the invention was determined using a TA DSC 2920 from Thermal Analyst Instrument at a scan rate of 20° C./min.

Because of the long crystallization half-times (e.g., greater than 5 minutes) at 170° C. exhibited by certain polyesters useful in the present invention, it can be possible to produce injection blow molded articles, injection stretch blow molded articles, extrusion blow molded articles and extrusion stretch blow molded. The polyesters of the invention can be "amorphous" or semicrystalline. In one aspect, certain polyesters useful in the invention can have a relatively low crystallinity. Certain polyesters useful in the invention can thus have a substantially amorphous morphology, meaning that the polyesters comprise substantially unordered regions of polymer.

In one embodiment, an "amorphous" polyester can have a crystallization half-time of greater than 5 minutes at 170° C. or greater than 10 minutes at 170° C. or greater than 50 minutes at 170° C. or greater than 100 minutes at 170° C. In one embodiment, of the invention, the crystallization half-times can be greater than 1,000 minutes at 170° C. In another embodiment of the invention, the crystallization half-times of the polyesters useful in the invention can be greater than 10,000 minutes at 170° C. The crystallization half time of the polyester, as used herein, may be measured using methods well-known to persons of skill in the art. For example, the crystallization half time of the polyester, $t_{1/2}$, can be determined by measuring the light transmission of a sample via a laser and photo detector as a function of time on a temperature controlled hot stage. This measurement can be done by exposing the polymers to a temperature, $T_{max}$, and then cooling it to the desired temperature. The sample can then be held at the desired temperature by a hot stage while transmission measurements are made as a function of time. Initially, the sample can be visually clear with high light transmission and becomes opaque as the sample crystallizes. The crystallization half-time is the time at which the light transmission is halfway between the initial transmission and the final transmission. $T_{max}$ is defined as the temperature required to melt the crystalline domains of the sample (if crystalline domains are present). The sample can be heated to $T_{max}$ to condition the sample prior to crystallization half time measurement. The absolute $T_{max}$ temperature is different for each composition. For example PCT can be heated to some temperature greater than 290° C. to melt the crystalline domains.

As shown in Table 1 and FIG. 1 of the Examples, 2,2,4,4-tetramethyl-1,3-cyclobutanediol is more effective than other comonomers such ethylene glycol and isophthalic acid at increasing the crystallization half-time, i.e., the time required for a polymer to reach half of its maximum crystallinity. By decreasing the crystallization rate of PCT, i.e. increasing the crystallization half-time, amorphous articles based on modified PCT may be fabricated by methods known in the art such as extrusion, injection molding, and the like. As shown in Table 1, these materials can exhibit higher glass transition temperatures and lower densities than other modified PCT copolyesters.

The polyesters can exhibit an improvement in toughness combined with processability for some of the embodiments of the invention. For example, lowering the inherent viscosity slightly of the polyesters useful in the invention results in a more processable melt viscosity while retaining good physical properties of the polyesters such as toughness and heat resistance.

Figure 2:
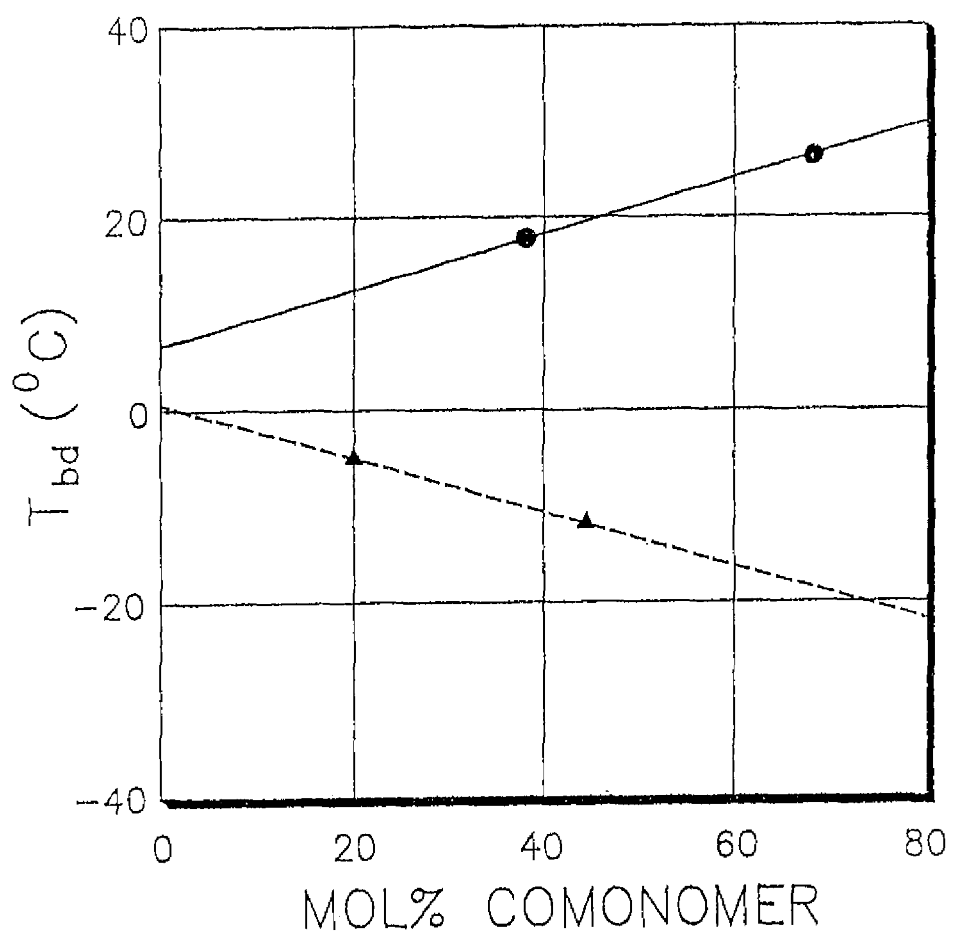
FIG. 2 is a graph showing the effect of comonomer on the brittle-to-ductile transition temperature ($T_{bd}$) in a notched Izod impact strength test (ASTM D256, ⅛-in thick, 10-mil notch).

Increasing the content of 1,4-cyclohexanedimethanol in a copolyester based on terephthalic acid, ethylene glycol, and 1,4-cyclohexanedimethanol can improve toughness which can be determined by the brittle-to-ductile transition temperature in a notched Izod impact strength test as measured by ASTM D256. This toughness improvement, by lowering of the brittle-to-ductile transition temperature with 1,4-cyclohexanedimethanol, is believed to occur due to the flexibility and conformational behavior of 1,4-cyclohexanedimethanol in the copolyester. Incorporating 2,2,4,4-tetramethyl-1,3-cyclobutanediol into PCT is believed to improve toughness, by lowering the brittle-to-ductile transition temperature, as shown in Table 2 and FIG. 2 of the Examples. This is unexpected given the rigidity of 2,2,4,4-tetramethyl-1,3-cyclobutanediol.

In one embodiment, the melt viscosity of the polyester(s) useful in the invention is less than 30,000 poise as measured a 1 radian/second on a rotary melt rheometer at 290° C. In another embodiment, the melt viscosity of the polyester(s)

useful in the invention is less than 20,000 poise as measured a 1 radian/second on a rotary melt rheometer at 290° C.

In one embodiment, the melt viscosity of the polyester(s) useful in the invention is less than 15,000 poise as measured at 1 radian/second (rad/sec) on a rotary melt rheometer at 290° C. In one embodiment, the melt viscosity of the polyester(s) useful in the invention is less than 10,000 poise as measured at 1 radian/second (rad/sec) on a rotary melt rheometer at 290° C. In another embodiment, the melt viscosity of the polyester(s) useful in the invention is less than 6,000 poise as measured at 1 radian/second on a rotary melt rheometer at 290° C. Viscosity at rad/sec is related to processability. Typical polymers have viscosities of less than 10,000 poise as measured at 1 radian/second when measured at their processing temperature. Polyesters are typically not processed above 290 C. Polycarbonate is typically processed at 290 C. The viscosity at 1 rad/sec of a typical 12 melt flow rate polycarbonate is 7000 poise at 290 C.

In one embodiment, certain polyesters useful in this invention can be visually clear. The term "visually clear" is defined herein as an appreciable absence of cloudiness, haziness, and/or muddiness, when inspected visually. In another embodiment, when the polyesters are blended with polycarbonate, including but not limited to, bisphenol A polycarbonates, the blends can be visually clear.

In other embodiments of the invention, the polyesters useful in the invention may have a yellowness index (ASTM D-1925) of less than 50 or less than 20.

In one embodiment, the polyesters useful in the invention and/or the polyester compositions of the invention, with or without toners, can have color values L*, a* and b* which can be determined using a Hunter Lab Ultrascan Spectra Colorimeter manufactured by Hunter Associates Lab Inc., Reston, Va. The color determinations are averages of values measured on either pellets of the polyesters or plaques or other items injection molded or extruded from them. They are determined by the L*a*b* color system of the CIE (International Commission on Illumination) (translated), wherein L* represents the lightness coordinate, a* represents the red/green coordinate, and b* represents the yellow/blue coordinate. In certain embodiments, the b* values for the polyesters useful in the invention can be from −10 to less than 10 and the L* values can be from 50 to 90. In other embodiments, the b* values for the polyesters useful in the invention can be present in one of the following ranges: from −10 to 9; −10 to 8; −10 to 7; −10 to 6; −10 to 5; −10 to 4; −10 to 3; −10 to 2; from −5 to 9; −5 to 8; −5 to 7; −5 to 6; −5 to 5; −5 to 4; −5 to 3; −5 to 2; 0 to 9; 0 to 8; 0 to 7; 0 to 6; 0 to 5; 0 to 4; 0 to 3; 0 to 2; 1 to 10; 1 to 9; 1 to 8; 1 to 7; 1 to 6; 1 to 5; 1 to 4; 1 to 3; and 1 to 2. In other embodiments, the L* value for the polyesters useful in the invention can be present in one of the following ranges: 50 to 60; 50 to 70; 50 to 80; 50 to 90; 60 to 70; 60 to 80; 60 to 90; 70 to 80; 79 to 90.

In some embodiments, use of the polyester compositions useful in the invention minimizes and/or eliminates the drying step prior to melt processing and/or thermoforming.

The present polyesters useful in this invention can possess one or more of the following properties. In one embodiment, the polyesters useful in the invention exhibit a Notched Izod impact strength of at least 150 J/m (3 ft-lb/in) at 23° C. with a 10-mil notch in a 3.2 mm (⅛-inch) thick bar determined according to ASTM D256; in one embodiment, the polyesters useful in the invention exhibit a notched Izod impact strength of at least (400 J/m) 7.5 ft-lb/in at 23° C. with a 10-mil notch in a 3.2 mm (⅛-inch) thick bar determined according to ASTM D256; in one embodiment, the polyesters useful in the invention exhibit a notched Izod impact strength of at least 1000 J/m (18 ft-lb/in) at 23° C. with a 10-mil notch in a 3.2 mm (⅛-inch) thick bar determined according to ASTM D256. In one embodiment, the polyesters useful in the invention exhibit a notched Izod impact strength of at least 150 J/m (3 ft-lb/in) at 23° C. with a 10-mil notch in a 6.4 mm (¼-inch) thick bar determined according to ASTM D256; in one embodiment, the polyesters useful in the invention exhibit a notched Izod impact strength of at least (400 J/m) 7.5 ft-lb/in at 23° C. with a 10-mil notch in a 6.4 mm (¼-inch) thick bar determined according to ASTM D256; in one embodiment, the polyesters useful in the invention exhibit a notched Izod impact strength of at least 1000 J/m (18 ft-lb/in) at 23° C. with a 10-mil notch in a 6.4 mm (¼-inch) thick bar determined according to ASTM D256.

In another embodiment, certain polyesters useful in the invention can exhibit an increase in notched Izod impact strength when measured at 0° C. of at least 3% or at least 5% or at least 10% or at least 15% as compared to the notched Izod impact strength when measured at −5° C. with a 10-mil notch in a ⅛-inch thick bar determined according to ASTM D256. In addition, certain other polyesters can also exhibit a retention of notched Izod impact strength within plus or minus 5% when measured at 0° C. through 30° C. with a 10-mil notch in a ⅛-inch thick bar determined according to ASTM D256.

In yet another embodiment, certain polyesters useful in the invention can exhibit a retention in notched Izod impact strength with a loss of no more than 70% when measured at 23° C. with a 10-mil notch in a ¼-inch thick bar determined according to ASTM D256 as compared to notched Izod impact strength for the same polyester when measured at the same temperature with a 10-mil notch in a ⅛-inch thick bar determined according to ASTM D256.

In one embodiment, the polyesters useful in the invention can exhibit a ductile-to-brittle transition temperature of less than 0° C. based on a 10-mil notch in a ⅛-inch thick bar as defined by ASTM D256.

In one embodiment, the polyesters useful in the invention can exhibit at least one of the following densities: a density of less than 1.2 g/ml at 23° C.; a density of less than 1.18 g/ml at 23° C.; a density of 0.8 to 1.3 g/ml at 23° C.; a density of 0.80 to 1.2 g/ml at 23° C.; a density of 0.80 to less than 1.2 g/ml at 23° C.; a density of 1.0 to 1.3 g/ml at 23° C.; a density of 1.0 to 1.2 g/ml at 23° C.; a density of 1.0 to 1.1 g/ml at 23° C.; a density of 1.13 to 1.3 g/ml at 23° C.; a density of 1.13 to 1.2 g/ml at 23° C.

In one embodiment, polyesters of this invention exhibit superior notched toughness in thick sections. Notched Izod impact strength, as described in ASTM D256, is a common method of measuring toughness. When tested by the Izod method, polymers can exhibit either a complete break failure mode, where the test specimen breaks into two distinct parts, or a partial or no break failure mode, where the test specimen remains as one part. The complete break failure mode is associated with low energy failure. The partial and no break failure modes are associated with high energy failure. A typical thickness used to measure Izod toughness is ⅛". At this thickness, very few polymers are believed to exhibit a partial or no break failure mode, polycarbonate being one notable example. When the thickness of the test specimen is increased to ¼", however, no commercial amorphous materials exhibit a partial or no break failure mode. In one embodiment, compositions of the present example exhibit a no break failure mode when tested in Izod using a ¼" thick specimen.

In some embodiments, use of the polyester compositions useful in the invention minimizes and/or eliminates the drying step prior to melt processing and/or thermoforming.

The polyester portion of the polyester compositions useful in the invention can be made by processes known from the literature such as, for example, by processes in homogenous solution, by transesterification processes in the melt, and by two phase interfacial processes. Suitable methods include, but are not limited to, the steps of reacting one or more dicarboxylic acids with one or more glycols at a temperature of 100° C. to 315° C. at a pressure of 0.1 to 760 mm Hg for a time sufficient to form a polyester. See U.S. Pat. No. 3,772,405 for methods of producing polyesters, the disclosure regarding such methods is hereby incorporated herein by reference.

In another aspect, the invention relates to polyester compositions useful in the invention comprising a polyester produced by a process comprising:

(I) heating a mixture comprising the monomers useful in any of the polyesters useful in the invention in the presence of a catalyst at a temperature of 150 to 240° C. for a time sufficient to produce an initial polyester;

(II) heating the initial polyester of step (I) at a temperature of 240 to 320° C. for 1 to 4 hours; and (III) removing any unreacted glycols.

Suitable catalysts for use in this process include, but are not limited to, organo-zinc or tin compounds. The use of this type of catalyst is well known in the art. Examples of catalysts useful in the present invention include, but are not limited to, zinc acetate, butyltin tris-2-ethylhexanoate, dibutyltin diacetate, and dibutyltin oxide. Other catalysts may include, but are not limited to, those based on titanium, zinc, manganese, lithium, germanium, and cobalt. Catalyst amounts can range from 10 ppm to 20,000 ppm or 10 to 10,000 ppm, or 10 to 5000 ppm or 10 to 1000 ppm or 10 to 500 ppm, or 10 to 300 ppm or 10 to 250 based on the catalyst metal and based on the weight of the final polymer. The process can be carried out in either a batch or continuous process.

Typically, step (I) can be carried out until 50% by weight or more of the 2,2,4,4-tetramethyl-1,3-cyclobutanediol has been reacted. Step (I) may be carried out under pressure, ranging from atmospheric pressure to 100 psig. The term "reaction product" as used in connection with any of the catalysts useful in the invention refers to any product of a polycondensation or esterification reaction with the catalyst and any of the monomers used in making the polyester as well as the product of a polycondensation or esterification reaction between the catalyst and any other type of additive.

Typically, Step (II) and Step (III) can be conducted at the same time. These steps can be carried out by methods known in the art such as by placing the reaction mixture under a pressure ranging, from 0.002 psig to below atmospheric pressure, or by blowing hot nitrogen gas over the mixture.

The invention further relates to a polyester product made by the process described above.

The invention further relates to a polymer blend. The blend comprises:

(a) from 5 to 95 wt % of at least one of the polyesters described above; and (b) from 5 to 95 wt % of at least one of the polymeric components.

Suitable examples of the polymeric components include, but are not limited to, nylon, polyesters different from those described herein, polyamides such as ZYTEL® from DuPont; polystyrene, polystyrene copolymers, styrene acrylonitrile copolymers, acrylonitrile butadiene styrene copolymers, poly(methylmethacrylate), acrylic copolymers, poly(ether-imides) such as ULTEM® (a poly(ether-imide) from General Electric); polyphenylene oxides such as poly(2,6-dimethylphenylene oxide) or poly(phenylene oxide)/polystyrene blends such as NORYL 1000® (a blend of poly(2,6-dimethylphenylene oxide) and polystyrene resins from General Electric); polyphenylene sulfides; polyphenylene sulfide/sulfones; poly(ester-carbonates); polycarbonates such as LEXAN® (a polycarbonate from General Electric); polysulfones; polysulfone ethers; and poly(ether-ketones) of aromatic dihydroxy compounds; or mixtures of any of the foregoing polymers. The blends can be prepared by conventional processing techniques known in the art, such as melt blending or solution blending. In one embodiment, the polycarbonate is not present in the polyester composition. If polycarbonate is used in a blend in the polyester compositions useful in the invention, the blends can be visually clear. However, the polyester compositions useful in the invention also contemplate the exclusion of polycarbonate as well as the inclusion of polycarbonate.

Polycarbonates useful in the invention may be prepared according to known procedures, for example, by reacting the dihydroxyaromatic compound with a carbonate precursor such as phosgene, a haloformate or a carbonate ester, a molecular weight regulator, an acid acceptor and a catalyst. Methods for preparing polycarbonates are known in the art and are described, for example, in U.S. Pat. No. 4,452,933, where the disclosure regarding the preparation of polycarbonates is hereby incorporated by reference herein.

Examples of suitable carbonate precursors include, but are not limited to, carbonyl bromide, carbonyl chloride, or mixtures thereof; diphenyl carbonate; a di(halophenyl)carbonate, e.g., di(trichlorophenyl) carbonate, di(tribromophenyl) carbonate, and the like; di(alkylphenyl)carbonate, e.g., di(tolyl) carbonate; di(naphthyl)carbonate; di(chloronaphthyl)carbonate, or mixtures thereof; and bis-haloformates of dihydric phenols.

Examples of suitable molecular weight regulators include, but are not limited to, phenol, cyclohexanol, methanol, alkylated phenols, such as octylphenol, para-tertiary-butyl-phenol, and the like. In one embodiment, the molecular weight regulator is phenol or an alkylated phenol.

The acid acceptor may be either an organic or an inorganic acid acceptor. A suitable organic acid acceptor can be a tertiary amine and includes, but is not limited to, such materials as pyridine, triethylamine, dimethylaniline, tributylamine, and the like. The inorganic acid acceptor can be either a hydroxide, a carbonate, a bicarbonate, or a phosphate of an alkali or alkaline earth metal.

The catalysts that can be used include, but are not limited to, those that typically aid the polymerization of the monomer with phosgene. Suitable catalysts include, but are not limited to, tertiary amines such as triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethyl ammonium chloride, tetra-methyl ammonium hydroxide, tetra-n-butyl ammonium iodide, benzyltrimethyl ammonium chloride and quaternary phosphonium compounds such as, for example, n-butyltriphenyl phosphonium bromide and methyltriphenyl phosphonium bromide.

The polycarbonates useful in the polyester compositions of the invention also may be copolyestercarbonates such as those described in U.S. Pat. Nos. 3,169,121; 3,207,814; 4,194,038; 4,156,069; 4,430,484, 4,465,820, and 4,981,898, where the disclosure regarding copolyestercarbonates from each of the U.S. patents is incorporated by reference herein.

Copolyestercarbonates useful in this invention can be available commercially and/or may be prepared by known methods in the art. For example, they can be typically obtained by the reaction of at least one dihydroxyaromatic compound with a mixture of phosgene and at least one dicarboxylic acid chloride, especially isophthaloyl chloride, terephthaloyl chloride, or both.

In addition, the polyester compositions and the polymer blend compositions containing the polyesters of this invention may also contain from 0.01 to 25% by weight or 0.01 to 20% by weight or 0.01 to 15% by weight or 0.01 to 10% by weight or 0.01 to 5% by weight of the total weight of the polyester composition of common additives such as colorants, dyes, mold release agents, flame retardants, plasticizers, nucleating agents, stabilizers, including but not limited to, UV stabilizers, thermal stabilizers and/or reaction products thereof, fillers, and impact modifiers. Examples of typical commercially available impact modifiers well known in the art and useful in this invention include, but are not limited to, ethylene/propylene terpolymers; functionalized polyolefins, such as those containing methyl acrylate and/or glycidyl methacrylate; styrene-based block copolymeric impact modifiers; and various acrylic core/shell type impact modifiers. For example, UV additives can be incorporated into articles of manufacture through addition to the bulk, through application of a hard coat, or through coextrusion of a cap layer. Residues of such additives are also contemplated as part of the polyester composition.

The polyesters of the invention can comprise at least one chain extender. Suitable chain extenders include, but are not limited to, multifunctional (including, but not limited to, bifunctional) isocyanates, multifunctional epoxides, including for example, epoxylated novolacs, and phenoxy resins. In certain embodiments, chain extenders may be added at the end of the polymerization process or after the polymerization process. If added after the polymerization process, chain extenders can be incorporated by compounding or by addition during conversion processes such as injection molding or extrusion. The amount of chain extender used can vary depending on the specific monomer composition used and the physical properties desired but is generally about 0.1 percent by weight to about 10 percent by weight, such as about 0.1 to about 5 percent by weight, based on the total weight of the polyester.

Thermal stabilizers are compounds that stabilize polyesters during polyester manufacture and/or post polymerization, including but not limited to phosphorous compounds including but not limited to phosphoric acid, phosphorous acid, phosphonic acid, phosphinic acid, phosphonous acid, and various esters and salts thereof. These can be present in the polyester compositions useful in the invention. The esters can be alkyl, branched alkyl, substituted alkyl, difunctional alkyl, alkyl ethers, aryl, and substituted aryl. In one embodiment, the number of ester groups present in the particular phosphorous compound can vary from zero up to the maximum allowable based on the number of hydroxyl groups present on the thermal stabilizer used. The term "thermal stabilizer" is intended to include the reaction product(s) thereof. The term "reaction product" as used in connection with the thermal stabilizers of the invention refers to any product of a polycondensation or esterification reaction between the thermal stabilizer and any of the monomers used in making the polyester as well as the product of a polycondensation or esterification reaction between the catalyst and any other type of additive.

Reinforcing materials may be useful in the compositions of this invention. The reinforcing materials may include, but are not limited to, carbon filaments, silicates, mica, clay, talc, titanium dioxide, Wollastonite, glass flakes, glass beads and fibers, and polymeric fibers and combinations thereof. In one embodiment, the reinforcing materials include glass, such as, fibrous glass filaments, mixtures of glass and talc, glass and mica, and glass and polymeric fibers.

The invention also include articles of manufacture comprising the polyester compositions described herein.

The invention further relates to articles of manufacture described herein. These article of manufacture include, but are not limited to, injection blow molded articles, injection stretch blow molded articles, extrusion blow molded articles, extrusion stretch blow molded articles, calendered articles, compression molded articles, and solution casted articles. Methods of making the articles of manufacture of the invention include, but are not limited to, extrusion blow molding, extrusion stretch blow molding, injection blow molding, injection stretch blow molding, calendering, compression molding, and solution casting.

The term "container" as used herein is understood to mean a receptacle in which material is held or stored. "Containers" include but are not limited to bottles, bags, vials, tubes and jars. Applications in the industry for these types of containers include but are not limited to food, beverage, cosmetics and personal care applications.

The term "bottle" as used herein is understood to mean a receptacle containing plastic which is capable of storing or holding liquid.

The invention further relates to bottles described herein. The methods of forming the polyesters into bottles are well known in the art. Examples of bottles include but are not limited to bottles such as baby bottles; water bottles; juice bottles; large commercial water bottles having a weight from 200 to 800 grams; beverage bottles which include but are not limited to two liter bottles, 20 ounce bottles, 16.9 ounce bottles; medical bottles; personal care bottles, carbonated soft drink bottles; hot fill bottles; water bottles; alcoholic beverage bottles such as beer bottles and wine bottles; and bottles comprising at least one handle. These bottles include but are not limited to injection blow molded bottles, injection stretch blow molded bottles, extrusion blow molded bottles, and extrusion stretch blow molded bottles. Methods of making bottles include but are not limited to extrusion blow molding, extrusion stretch blow molding, injection blow molding, and injection stretch blow molding. In each case, the invention further relates to the preforms (or parisons) used to make each of said bottles.

Other examples of containers include, but are not limited to, containers for cosmetics and personal care applications including bottles, jars, vials and tubes; sterilization containers; buffet steam pans; food pans or trays; frozen food trays; microwaveable food trays; hot fill containers, amorphous lids or sheets to seal or cover food trays; food storage containers; for example, boxes; tumblers, pitchers, cups, bowls, including but not limited to those used in restaurant smallware; beverage containers; retort food containers; centrifuge bowls; vacuum cleaner canisters, and collection and treatment canisters.

Articles of manufacture of the present invention also include film and/or sheet.

The films and/or sheets useful in the present invention can be of any thickness which would be apparent to one of ordinary skill in the art. In one embodiment, the film(s) of the invention have a thickness of no more than 40 mils. In one embodiment, the film(s) of the invention have a thickness of no more than 35 mils. In one embodiment, the film(s) of the invention have a thickness of no more than 30 mils. In one embodiment, the film(s) of the invention have a thickness of no more than 25 mils. In one embodiment, the film(s) of the invention have a thickness of no more than 20 mils.

In one embodiment, the sheet(s) of the invention have a thickness of no less than 20 mils. In another embodiment, the sheet(s) of the invention have a thickness of no less than 25 mils. In another embodiment, the sheet(s) of the invention have a thickness of no less than 30 mils. In another embodiment, the sheet(s) of the invention have a thickness of no less than 35 mils. In another embodiment, the sheet(s) of the invention have a thickness of no less than 40 mils.

The invention further relates to the film(s) and/or sheet(s) comprising the polyester compositions of the invention. The methods of forming the polyesters into film(s) and/or sheet(s) are well known in the art. Examples of film(s) and/or sheet(s) of the invention including but not limited to extruded film(s) and/or sheet(s), calendered film(s) and/or sheet(s), compression molded film(s) and/or sheet(s), solution casted film(s) and/or sheet(s). Methods of making film and/or sheet include but are not limited to extrusion, calendering, compression molding, and solution casting.

For the purposes of this invention, the term "wt" means "weight".

The following examples further illustrate how the polyesters useful in the invention can be made and evaluated, and are intended to be purely exemplary of the invention and are not intended to limit the scope thereof. Unless indicated otherwise, parts are parts by weight, temperature is in degrees C. or is at room temperature, and pressure is at or near atmospheric.

EXAMPLES

Measurement Methods

The inherent viscosity of the polyesters was determined in 60/40 (wt/wt) phenol/tetrachloroethane at a concentration of 0.5 g/100 ml at 25° C.

Unless stated otherwise, the glass transition temperature ($T_g$) was determined using a TA DSC 2920 instrument from Thermal Analyst Instruments at a scan rate of 20° C./min according to ASTM D3418.

The glycol content and the cis/trans ratio of the compositions were determined by proton nuclear magnetic resonance (NMR) spectroscopy. All NMR spectra were recorded on a JEOL Eclipse Plus 600 MHz nuclear magnetic resonance spectrometer using either chloroform-trifluoroacetic acid (70-30 volume/volume) for polymers or, for oligomeric samples, 60/40 (wt/wt) phenol/tetrachloroethane with deuterated chloroform added for lock. Peak assignments for 2,2,4,4-tetramethyl-1,3-cyclobutanediol resonances were made by comparison to model mono- and dibenzoate esters of 2,2,4,4-tetramethyl-1,3-cyclobutanediol. These model compounds closely approximate the resonance positions found in the polymers and oligomers.

The crystallization half-time, t½, was determined by measuring the light transmission of a sample via a laser and photo detector as a function of time on a temperature controlled hot stage. This measurement was done by exposing the polymers to a temperature, $T_{max}$, and then cooling it to the desired temperature. The sample was then held at the desired temperature by a hot stage while transmission measurements were made as a function of time. Initially, the sample was visually clear with high light transmission and became opaque as the sample crystallized. The crystallization half-time was recorded as the time at which the light transmission was halfway between the initial transmission and the final transmission. $T_{max}$ is defined as the temperature required to melt the crystalline domains of the sample (if crystalline domains are present). The $T_{max}$ reported in the examples below represents the temperature at which each sample was heated to condition the sample prior to crystallization half time measurement. The $T_{max}$ temperature is dependant on composition and is typically different for each polyester. For example, PCT may need to be heated to some temperature greater than 290° C. to melt the crystalline domains.

Density was determined using a gradient density column at 23° C.

The melt viscosity reported herein was measured by using a Rheometrics Dynamic Analyzer (RDA II). The melt viscosity was measured as a function of shear rate, at frequencies ranging from 1 to 400 rad/sec, at the temperatures reported. The zero shear melt viscosity ($\eta_o$) is the melt viscosity at zero shear rate estimated by extrapolating the data by known models in the art. This step is automatically performed by the Rheometrics Dynamic Analyzer (RDA II) software.

The polymers were dried at a temperature ranging from 80 to 100° C. in a vacuum oven for 24 hours and injection molded on a Boy 22S molding machine to give ⅛×½×5-inch and ¼×½×5-inch flexure bars. These bars were cut to a length of 2.5 inch and notched down the ½ inch width with a 10-mil notch in accordance with ASTM D256. The average Izod impact strength at 23° C. was determined from measurements on 5 specimens.

In addition, 5 specimens were tested at various temperatures using 5° C. increments in order to determine the brittle-to-ductile transition temperature. The brittle-to-ductile transition temperature is defined as the temperature at which 50% of the specimens fail in a brittle manner as denoted by ASTM D256.

Color values reported herein were determined using a Hunter Lab Ultrascan Spectra Colorimeter manufactured by Hunter Associates Lab Inc., Reston, Va. The color determinations were averages of values measured on either pellets of the polyesters or plaques or other items injection molded or extruded from them. They were determined by the L*a*b* color system of the CIE (International Commission on Illumination) (translated), wherein L* represents the lightness coordinate, a* represents the red/green coordinate, and b* represents the yellow/blue coordinate.

In addition, 10-mil films were compression molded using a Carver press at 240° C.

Unless otherwise specified, the cis/trans ratio of the 1,4 cyclohexanedimethanol used in the following examples was approximately 30/70, and could range from 35/65 to 25/75. Unless otherwise specified, the cis/trans ratio of the 2,2,4,4-tetramethyl-1,3-cyclobutanediol used in the following examples was approximately 50/50.

The following abbreviations apply throughout the working examples and figures:

| | |
|---|---|
| TPA | Terephthalic acid |
| DMT | Dimethyl terephthalate |
| TMCD | 2,2,4,4-tetramethyl-1,3-cyclobutanediol |
| CHDM | 1,4-cyclohexanedimethanol |
| IV | Inherent viscosity |
| $\eta_o$ | Zero shear melt viscosity |
| $T_g$ | Glass transition temperature |
| $T_{bd}$ | Brittle-to-ductile transition temperature |
| $T_{max}$ | Conditioning temperature for crystallization half time measurements |

Example 1

This example illustrates that 2,2,4,4-tetramethyl-1,3-cyclobutanediol is more effective at reducing the crystallization rate of PCT than ethylene glycol or isophthalic acid. In addition, this example illustrates the benefits of 2,2,4,4-tetramethyl-1,3-cyclobutanediol on the glass transition temperature and density.

A variety of copolyesters were prepared as described below. These copolyesters were all made with 200 ppm dibutyl tin oxide as the catalyst in order to minimize the effect of catalyst type and concentration on nucleation during crystallization studies. The cis/trans ratio of the 1,4-cyclohexanedimethanol was 31/69 while the cis/trans ratio of the 2,2,4,4-tetramethyl-1,3-cyclobutanediol is reported in Table 1.

For purposes of this example, the samples had sufficiently similar inherent viscosities thereby effectively eliminating this as a variable in the crystallization rate measurements.

Crystallization half-time measurements from the melt were made at temperatures from 140 to 200° C. at 10° C. increments and are reported in Table 1. The fastest crystallization half-time for each sample was taken as the minimum value of crystallization half-time as a function of temperature, typically occurring around 170 to 180° C. The fastest crystallization half-times for the samples are plotted in FIG. 1 as a function of mole % comonomer modification to PCT.

The data shows that 2,2,4,4-tetramethyl-1,3-cyclobutanediol is more effective than ethylene glycol and isophthalic acid at decreasing the crystallization rate (i.e., increasing the crystallization half-time). In addition, 2,2,4,4-tetramethyl-1,3-cyclobutanediol increases $T_g$ and lowers density.

TABLE 1

| | | | | | | Crystallization Half-times (min) | | | | | | |
|---|---|---|---|---|---|---|---|---|---|---|---|---|
| Example | Comonomer (mol %)[1] | IV (dl/g) | Density (g/ml) | $T_g$ (° C.) | $T_{max}$ (° C.) | at 140° C. (min) | at 150° C. (min) | at 160° C. (min) | at 170° C. (min) | at 180° C. (min) | at 190° C. (min) | at 200° C. (min) |
| 1A | 20.2% A[2] | 0.630 | 1.198 | 87.5 | 290 | 2.7 | 2.1 | 1.3 | 1.2 | 0.9 | 1.1 | 1.5 |
| 1B | 19.8% B | 0.713 | 1.219 | 87.7 | 290 | 2.3 | 2.5 | 1.7 | 1.4 | 1.3 | 1.4 | 1.7 |
| 1C | 20.0% C | 0.731 | 1.188 | 100.5 | 290 | >180 | >60 | 35.0 | 23.3 | 21.7 | 23.3 | 25.2 |
| 1D | 40.2% A[2] | 0.674 | 1.198 | 81.2 | 260 | 18.7 | 20.0 | 21.3 | 25.0 | 34.0 | 59.9 | 96.1 |
| 1E | 34.5% B | 0.644 | 1.234 | 82.1 | 260 | 8.5 | 8.2 | 7.3 | 7.3 | 8.3 | 10.0 | 11.4 |
| 1F | 40.1% C | 0.653 | 1.172 | 122.0 | 260 | >10 days | >5 days | >5 days | 19204 | >5 days | >5 days | >5 days |
| 1G | 14.3% D | 0.646[3] | 1.188 | 103.0 | 290 | 55.0 | 28.8 | 11.6 | 6.8 | 4.8 | 5.0 | 5.5 |
| 1H | 15.0% E | 0.728[4] | 1.189 | 99.0 | 290 | 25.4 | 17.1 | 8.1 | 5.9 | 4.3 | 2.7 | 5.1 |

[1]The balance of the diol component of the polyesters in Table 1 is 1,4-cyclohexanedimethanol; and the balance of the dicarboxylic acid component of the polyesters in Table 1 is dimethyl terephthalate; if the dicarboxylic acid is not described, it is 100 mole % dimethyl terephthalate.
[2]100 mole % 1,4-cyclohexanedimethanol.
[3]A film was pressed from the ground polyester of Example 1G at 240° C.. The resulting film had an inherent viscosity value of 0.575 dL/g.
[4]A film was pressed from the ground polyester of Example 1H at 240° C.. The resulting film had an inherent viscosity value of 0.0.652 dL/g.

where:

A is Isophthalic Acid

B is Ethylene Glycol

C is 2,2,4,4-Tetramethyl-1,3-cyclobutanediol (approx. 50/50 cis/trans)

D is 2,2,4,4-Tetramethyl-1,3-cyclobutanediol (98/2 cis/trans)

E is 2,2,4,4-Tetramethyl-1,3-cyclobutanediol (5/95 cis/trans)

As shown in Table 1 and FIG. 1, 2,2,4,4-tetramethyl-1,3-cyclobutanediol is more effective than other comonomers, such ethylene glycol and isophthalic acid, at increasing the crystallization half-time, i.e., the time required for a polymer to reach half of its maximum crystallinity. By decreasing the crystallization rate of PCT (increasing the crystallization half-time), amorphous articles based on 2,2,4,4-tetramethyl-1,3-cyclobutanediol-modified PCT as described herein may be fabricated by methods known in the art. As shown in Table 1, these materials can exhibit higher glass transition temperatures and lower densities than other modified PCT copolyesters.

Preparation of the polyesters shown on Table 1 is described below.

Example 1A

This example illustrates the preparation of a copolyester with a target composition of 80 mol % dimethyl terephthalate residues, 20 mol % dimethyl isophthalate residues, and 100 mol % 1,4-cyclohexanedimethanol residues (28/72 cis/trans).

A mixture of 56.63 g of dimethyl terephthalate, 55.2 g of 1,4-cyclohexanedimethanol, 14.16 g of dimethyl isophthalate, and 0.0419 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 5 minutes and then the temperature was gradually increased to 290° C. over 30 minutes. The reaction mixture was held at 290° C. for 60 minutes and then vacuum was gradually applied over the next 5 minutes until the pressure inside the flask reached 100 mm of Hg. The pressure inside the flask was further reduced to 0.3 mm of Hg over the next 5 minutes. A pressure of 0.3 mm of Hg was maintained for a total time of 90 minutes to remove excess unreacted diols. A high melt viscosity, visually clear and colorless polymer was obtained with a glass transition temperature of 87.5° C. and an inherent viscosity of 0.63 dl/g. NMR analysis showed that the polymer was composed of 100 mol % 1,4-cyclohexanedimethanol residues and 20.2 mol % dimethyl isophthalate residues.

Example 1B

This example illustrates the preparation of a copolyester with a target composition of 100 mol % dimethyl terephthalate residues, 20 mol % ethylene glycol residues, and 80 mol % 1,4-cyclohexanedimethanol residues (32/68 cis/trans).

A mixture of 77.68 g of dimethyl terephthalate, 50.77 g of 1,4-cyclohexanedimethanol, 27.81 g of ethylene glycol, and 0.0433 g of dibutyl tin oxide was placed in a 500-milliliter flask equipped with an inlet for nitrogen, a metal stirrer, and a short distillation column. The flask was placed in a Wood's metal bath already heated to 200° C. The stirring speed was set to 200 RPM throughout the experiment. The contents of the flask were heated at 200° C. for 60 minutes and then the temperature was gradually increased to 210° C. over 5 minutes. The reaction mixture was held at 210° C. for 120 minutes and then heated up to 280° C. in 30 minutes. Once at 280° C., vacuum was gradually applied over the next 5 minutes until the pressure inside the flask reached 100 mm of Hg. The pressure inside the flask was further reduced to 0.3 mm of Hg over the next 10 minutes. A pressure of 0.3 mm of Hg was maintained for a total time of 90 minutes to remove excess unreacted diols. A high melt viscosity, visually clear and colorless polymer was obtained with a glass transition temperature of 87.7° C. and an inherent viscosity of 0.71 dl/g. NMR analysis showed that the polymer was composed of 19.8 mol % ethylene glycol residues.

Example 1C

This example illustrates the preparation of a copolyester with a target composition of 100 mol % dimethyl terephthalate residues, 20 mol % 2,2,4,4-tetramethyl-1,3-cyclobutanediol residues, and 80 mol % 1,4-cyclohexanedimethanol residues (31/69 cis/trans).

A mixture of 77.68 g of dimethyl terephthalate, 48.46 g of 1,4-cyclohexanedimethanol, 17.86 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. This polyester was prepared in a manner similar to that described in Example 1A. A high melt viscosity, visually clear and colorless polymer was obtained with a glass transition temperature of 100.5° C. and an inherent viscosity of 0.73 dl/g. NMR analysis showed that the polymer was composed of 80.5 mol % 1,4-cyclohexanedimethanol residues and 19.5 mol % 2,2,4,4-tetramethyl-1,3-cyclobutanediol residues.

Example 1D

This example illustrates the preparation of a copolyester with a target composition of 100 mol % dimethyl terephthalate residues, 40 mol % dimethyl isophthalate residues, and 100 mol % 1,4-cyclohexanedimethanol residues (28/72 cis/trans).

A mixture of 42.83 g of dimethyl terephthalate, 55.26 g of 1,4-cyclohexanedimethanol, 28.45 g of dimethyl isophthalate, and 0.0419 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 5 minutes and then the temperature was gradually increased to 290° C. over 30 minutes. The reaction mixture was held at 290° C. for 60 minutes and then vacuum was gradually applied over the next 5 minutes until the pressure inside the flask reached 100 mm of Hg. The pressure inside the flask was further reduced to 0.3 mm of Hg over the next 5 minutes. A pressure of 0.3 mm of Hg was maintained for a total time of 90 minutes to remove excess unreacted diols. A high melt viscosity, visually clear and colorless polymer was obtained with a glass transition temperature of 81.2° C. and an inherent viscosity of 0.67 dl/g. NMR analysis showed that the polymer was composed of 100 mol % 1,4-cyclohexanedimethanol residues and 40.2 mol % dimethyl isophthalate residues.

Example 1E

This example illustrates the preparation of a copolyester with a target composition of 100 mol % dimethyl terephthalate residues, 40 mol % ethylene glycol residues, and 60 mol % 1,4-cyclohexanedimethanol residues (31/69 cis/trans).

A mixture of 81.3 g of dimethyl terephthalate, 42.85 g of 1,4-cyclohexanedimethanol, 34.44 g of ethylene glycol, and 0.0419 g of dibutyl tin oxide was placed in a 500-milliliter flask equipped with an inlet for nitrogen, a metal stirrer, and a short distillation column. The flask was placed in a Wood's metal bath already heated to 200° C. The stirring speed was set to 200 RPM throughout the experiment. The contents of the flask were heated at 200° C. for 60 minutes and then the temperature was gradually increased to 210° C. over 5 minutes. The reaction mixture was held at 210° C. for 120 minutes and then heated up to 280° C. in 30 minutes. Once at 280° C., vacuum was gradually applied over the next 5 minutes until the pressure inside the flask reached 100 mm of Hg. The pressure inside the flask was further reduced to 0.3 mm of Hg over the next 10 minutes. A pressure of 0.3 mm of Hg was maintained for a total time of 90 minutes to remove excess unreacted diols. A high melt viscosity, visually clear and colorless polymer was obtained with a glass transition temperature of 82.1° C. and an inherent viscosity of 0.64 dl/g. NMR analysis showed that the polymer was composed of 34.5 mol % ethylene glycol residues.

Example 1F

This example illustrates the preparation of a copolyester with a target composition of 100 mol % dimethyl terephthalate residues, 40 mol % 2,2,4,4-tetramethyl-1,3-cyclobutanediol residues, and 60 mol % 1,4-cyclohexanedimethanol residues (31/69 cis/trans).

A mixture of 77.4 g of dimethyl terephthalate, 36.9 g of 1,4-cyclohexanedimethanol, 32.5 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 3 minutes and then the temperature was gradually increased to 260° C. over 30 minutes. The reaction mixture was held at 260° C. for 120 minutes and then heated up to 290° C. in 30 minutes. Once at 290° C., vacuum was gradually applied over the next 5 minutes until the pressure inside the flask reached 100 mm of Hg. The pressure inside the flask was further reduced to 0.3 mm of Hg over the next 5 minutes. A pressure of 0.3 mm of Hg was maintained for a total time of 90 minutes to remove excess unreacted diols. A high melt viscosity, visually clear and colorless polymer was obtained with a glass transition temperature of 122° C. and an inherent viscosity of 0.65 dl/g. NMR analysis showed that the polymer was composed of 59.9 mol % 1,4-cyclohexanedimethanol residues and 40.1 mol % 2,2,4,4-tetramethyl-1,3-cyclobutanediol residues.

Example 1G

This example illustrates the preparation of a copolyester with a target composition of 100 mol % dimethyl terephthalate residues, 20 mol % 2,2,4,4-tetramethyl-1,3-cyclobutanediol residues (98/2 cis/trans), and 80 mol % 1,4-cyclohexanedimethanol residues (31/69 cis/trans).

A mixture of 77.68 g of dimethyl terephthalate, 48.46 g of 1,4-cyclohexanedimethanol, 20.77 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM throughout the experiment. The contents of the flask were heated at 210° C. for 3 minutes and then the temperature was gradually increased to 260° C. over 30 minutes. The reaction mixture was held at 260° C. for 120 minutes and then heated up to 290° C. in 30 minutes. Once at 290° C., vacuum was gradually applied over the next 5 minutes until the pressure inside the flask reached 100 mm of Hg and the stirring speed was also reduced to 100 RPM. The pressure inside the flask was further reduced to 0.3 mm of Hg over the next 5 minutes and the stirring speed was reduced to 50 RPM. A pressure of 0.3 mm of Hg was maintained for a total time of 60 minutes to remove excess unreacted diols. A high melt viscosity, visually clear and colorless polymer was obtained with a glass transition temperature of 103° C. and an inherent viscosity of 0.65 dl/g. NMR analysis showed that the polymer was composed of 85.7 mol % 1,4-cyclohexanedimethanol residues and 14.3 mol % 2,2,4,4-tetramethyl-1,3-cyclobutanediol residues.

Example 1H

This example illustrates the preparation of a copolyester with a target composition of 100 mol % dimethyl terephthalate residues, 20 mol % 2,2,4,4-tetramethyl-1,3-cyclobutanediol residues (5/95 cis/trans), and 80 mol % 1,4-cyclohexanedimethanol residues (31/69 cis/trans).

A mixture of 77.68 g of dimethyl terephthalate, 48.46 g of 1,4-cyclohexanedimethanol, 20.77 g of 2,2,4,4-tetramethyl-1,3-cyclobutanediol, and 0.046 g of dibutyl tin oxide was placed in a 500-milliliter flask equipped with an inlet for nitrogen, a metal stirrer, and a short distillation column. The flask was placed in a Wood's metal bath already heated to 210° C. The stirring speed was set to 200 RPM at the beginning of the experiment. The contents of the flask were heated at 210° C. for 3 minutes and then the temperature was gradually increased to 260° C. over 30 minutes. The reaction mixture was held at 260° C. for 120 minutes and then heated up to 290° C. in 30 minutes. Once at 290° C., vacuum was gradually applied over the next 5 minutes with a set point of 100 mm of Hg and the stirring speed was also reduced to 100 RPM. The pressure inside the flask was further reduced to a set point of 0.3 mm of Hg over the next 5 minutes and the stirring speed was reduced to 50 RPM. This pressure was maintained for a total time of 60 minutes to remove excess unreacted diols. It was noted that the vacuum system failed to reach the set point mentioned above, but produced enough vacuum to produce a high melt viscosity, visually clear and colorless polymer with a glass transition temperature of 99° C. and an inherent viscosity of 0.73 dl/g. NMR analysis showed that the polymer was composed of 85 mol % 1,4-cyclohexanedimethanol residues and 15 mol % 2,2,4,4-tetramethyl-1,3-cyclobutanediol residues.

Example 2

This example illustrates the effect of the amount of 2,2,4,4-tetramethyl-1,3-cyclobutanediol used for the preparation of the polyesters of the invention on the glass transition temperature of the polyesters. Polyesters prepared in this example comprise from 15 to 25 mol % of 2,2,4,4-tetramethyl-1,3-cyclobutanediol residues.

Example 2A to Example 2G

Dimethyl terephthalate, 1,4-cyclohexanedimethanol, and 2,2,4,4-tetramethyl-1,3-cyclobutanediol were weighed into a 500-ml single neck round bottom flask. NMR analysis on the 2,2,4,4-tetramethyl-1,3-cyclobutanediol starting material showed a cis/trans ratio of 53/47. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 20 mol %.

Inherent viscosities were measured as described in the "Measurement Methods" section above. The compositions of the polyesters were determined by $^{1}H$ NMR as explained before in the Measurement Methods section. The glass transition temperatures were determined by DSC, using the second heat after quench at a rate of 20° C./min.

Example 2H to Example 2Q

These polyesters were prepared by carrying out the ester exchange and polycondensation reactions in separate stages. The ester exchange experiments were conducted in a continuous temperature rise (CTR) reactor. The CTR was a 3000 ml glass reactor equipped with a single shaft impeller blade agitator, covered with an electric heating mantle and fitted with a heated packed reflux condenser column. The reactor was charged with 777 g (4 moles) of dimethyl terephthalate, 230 g (1.6 moles) of 2,2,4,4-tetramethyl-1,3,-cyclobutanediol, 460.8 g (3.2 moles) of cyclohexane dimethanol and 1.12 g of butyltin tris-2-ethylhexanoate (such that there will be 200 ppm tin metal in the final polymer). The heating mantle was set manually to 100% output. The set points and data collection were facilitated by a Camile process control system. Once the reactants were melted, stirring was initiated and slowly increased to 250 rpm. The temperature of the reactor gradually increased with run time. The weight of methanol collected was recorded via balance. The reaction was stopped when methanol evolution stopped or at a pre-selected lower temperature of 260° C. The oligomer was discharged with a nitrogen purge and cooled to room temperature. The oligomer was frozen with liquid nitrogen and broken into pieces small enough to be weighed into a 500 ml round bottom flask.

In the polycondensation reactions, a 500 ml round bottom flask was charged with approximately 150 g of the oligomer prepared above. The flask was equipped with a stainless steel stirrer and polymer head. The glassware was set up on a half mole polymer rig and the Camile sequence was initiated. The stirrer was positioned one full turn from the flask bottom once the oligomer melted. The temperature/pressure/stir rate sequence controlled by the Camile software for each example is reported in the following tables.

Camile Sequence for Example 2H and Example 2I

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 290 | 6 | 25 |

Camile Sequence for Example 2N to Example 2Q

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 3 | 25 |
| 7 | 110 | 290 | 3 | 25 |

Camile Sequence for Example 2K and Example 2L

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 2 | 25 |
| 7 | 110 | 290 | 2 | 25 |

Camile Sequence for Example 2J and Example 2M

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 1 | 25 |
| 7 | 110 | 290 | 1 | 25 |

The resulting polymers were recovered from the flask, chopped using a hydraulic chopper, and ground to a 6 mm screen size. Samples of each ground polymer were submitted for inherent viscosity in 60/40 (wt/wt) phenol/tetrachloroethane at a concentration of 0.5 g/100 ml at 25° C., catalyst level (Sn) by x-ray fluorescence, and color (L*, a*, b*) by transmission spectroscopy. Polymer composition was obtained by $^{1}$H NMR. Samples were submitted for thermal stability and melt viscosity testing using a Rheometrics Mechanical Spectrometer (RMS-800).

Figure 3:
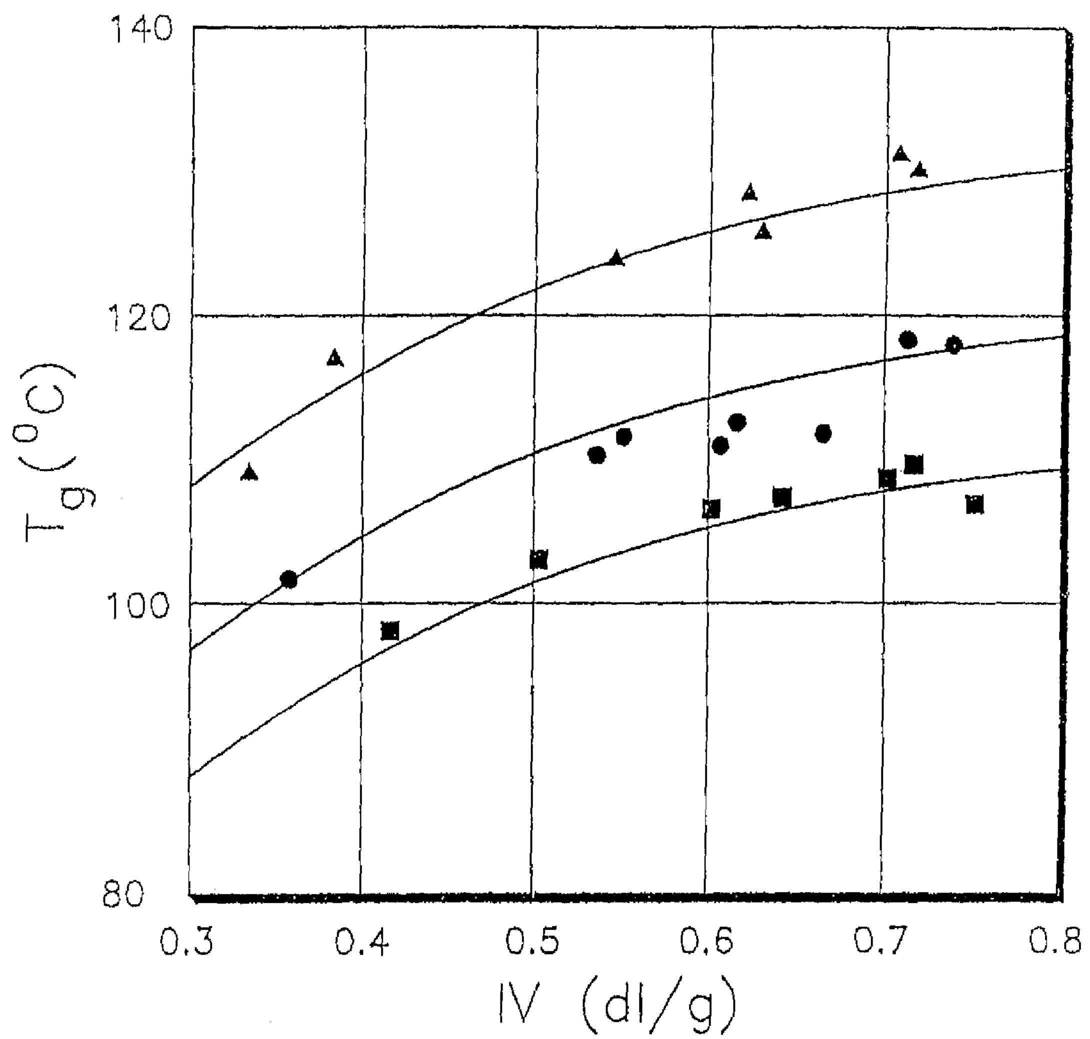
FIG. 3 is a graph showing the effect of 2,2,4,4-tetramethyl-1,3-cyclobutanediol composition on the glass transition temperature (Tg) of the copolyester.

The table below shows the experimental data for the polyesters of this example. The data shows that an increase in the level of 2,2,4,4-tetramethyl-1,3-cyclobutanediol raises the glass transition temperature in an almost linear fashion, for a constant inherent viscosity. FIG. 3 also shows the dependence of Tg on composition and inherent viscosity.

TABLE 2

Glass transition temperature as a function of inherent viscosity and composition

| Example | mol % TMCD | % cis TMCD | IV (dL/g) | $T_g$ (° C.) | $\eta_o$ at 260° C. (Poise) | $\eta_o$ at 275° C. (Poise) | $\eta_o$ at 290° C. (Poise) |
|---|---|---|---|---|---|---|---|
| A | 20 | 51.4 | 0.72 | 109 | 11356 | 19503 | 5527 |
| B | 19.1 | 51.4 | 0.60 | 106 | 6891 | 3937 | 2051 |
| C | 19 | 53.2 | 0.64 | 107 | 8072 | 4745 | 2686 |
| D | 18.8 | 54.4 | 0.70 | 108 | 14937 | 8774 | 4610 |
| E | 17.8 | 52.4 | 0.50 | 103 | 3563 | 1225 | 883 |
| F | 17.5 | 51.9 | 0.75 | 107 | 21160 | 10877 | 5256 |
| G | 17.5 | 52 | 0.42 | 98 | NA | NA | NA |
| H | 22.8 | 53.5 | 0.69 | 109 | NA | NA | NA |
| I | 22.7 | 52.2 | 0.68 | 108 | NA | NA | NA |
| J | 23.4 | 52.4 | 0.73 | 111 | NA | NA | NA |
| K | 23.3 | 52.9 | 0.71 | 111 | NA | NA | NA |
| L | 23.3 | 52.4 | 0.74 | 112 | NA | NA | NA |
| M | 23.2 | 52.5 | 0.74 | 112 | NA | NA | NA |
| N | 23.1 | 52.5 | 0.71 | 111 | NA | NA | NA |
| O | 22.8 | 52.4 | 0.73 | 112 | NA | NA | NA |
| P | 22.7 | 53 | 0.69 | 112 | NA | NA | NA |
| Q | 22.7 | 52 | 0.70 | 111 | NA | NA | NA |

NA = Not available

Example 3

This example illustrates the effect of the amount of 2,2,4,4-tetramethyl-1,3-cyclobutanediol used for the preparation of the polyesters of the invention on the glass transition temperature of the polyesters. Polyesters prepared in this example fall comprise more than 25 to less than 40 mol % of 2,2,4,4-tetramethyl-1,3-cyclobutanediol residues.

Dimethyl terephthalate, 1,4-cyclohexanedimethanol, and 2,2,4,4-tetramethyl-1,3-cyclobutanediol were weighed into a 500-ml single neck round bottom flask. NMR analysis on the 2,2,4,4-tetramethyl-1,3-cyclobutanediol starting material showed a cis/trans ratio of 53/47. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 32 mol %.

Inherent viscosities were measured as described in the "Measurement Methods" section above. The compositions of the polyesters were determined by $^{1}$H NMR as explained before in the Measurement Methods section. The glass transition temperatures were determined by DSC, using the second heat after quench at a rate of 20° C./min.

The table below shows the experimental data for the polyesters of this example. FIG. 3 also shows the dependence of Tg on composition and inherent viscosity. The data shows that an increase in the level of 2,2,4,4-tetramethyl-1,3-cyclobutanediol raises the glass transition temperature in an almost linear fashion, for a constant inherent viscosity.

TABLE 3

Glass transition temperature as a function of inherent viscosity and composition

| Example | mol % TMCD | % cis TMCD | IV (dL/g) | $T_g$ (° C.) | $\eta_o$ at 260° C. (Poise) | $\eta_o$ at 275° C. (Poise) | $\eta_o$ at 290° C. (Poise) |
|---|---|---|---|---|---|---|---|
| A | 32.2 | 51.9 | 0.71 | 118 | 29685 | 16074 | 8522 |
| B | 31.6 | 51.5 | 0.55 | 112 | 5195 | 2899 | 2088 |
| C | 31.5 | 50.8 | 0.62 | 112 | 8192 | 4133 | 2258 |
| D | 30.7 | 50.7 | 0.54 | 111 | 4345 | 2434 | 1154 |
| E | 30.3 | 51.2 | 0.61 | 111 | 7929 | 4383 | 2261 |
| F | 30.0 | 51.4 | 0.74 | 117 | 31476 | 17864 | 8630 |
| G | 29.0 | 51.5 | 0.67 | 112 | 16322 | 8787 | 4355 |
| H | 31.1 | 51.4 | 0.35 | 102 | NA | NA | NA |

NA = Not available

Example 4

This example illustrates the effect of the amount of 2,2,4,4-tetramethyl-1,3-cyclobutanediol used for the preparation of the polyesters of the invention on the glass transition temperature of the polyesters. Polyesters prepared in this example comprise 2,2,4,4-tetramethyl-1,3-cyclobutanediol residues in an amount of 40 mol % or greater.

Examples A to F

These polyesters were prepared by carrying out the ester exchange and polycondensation reactions in separate stages. The ester exchange experiments were conducted in a continuous temperature rise (CTR) reactor. The CTR was a 3000 ml glass reactor equipped with a single shaft impeller blade agitator, covered with an electric heating mantle and fitted with a heated packed reflux condenser column. The reactor was charged with 777 g of dimethyl terephthalate, 375 g of 2,2,4,4-tetramethyl-1,3,-cyclobutanediol, 317 g of cyclohexane dimethanol and 1.12 g of butyltin tris-2-ethylhexanoate (such that there will be 200 ppm tin metal in the final polymer). The heating mantle was set manually to 100% output. The set points and data collection were facilitated by a Camile process control system. Once the reactants were melted, stirring was initiated and slowly increased to 250 rpm. The temperature of the reactor gradually increased with run time. The weight of methanol collected was recorded via balance. The reaction was stopped when methanol evolution stopped or at a pre-selected lower temperature of 260° C. The oligomer was discharged with a nitrogen purge and cooled to room temperature. The oligomer was frozen with liquid nitrogen and broken into pieces small enough to be weighed into a 500 ml round bottom flask.

In the polycondensation reactions, a 500 ml round bottom flask was charged with 150 g of the oligomer prepared above. The flask was equipped with a stainless steel stirrer and polymer head. The glassware was set up on a half mole polymer rig and the Camile sequence was initiated. The stirrer was positioned one full turn from the flask bottom once the oligomer melted. The temperature/pressure/stir rate sequence controlled by the Camile software for these examples is reported in the following table, unless otherwise specified below.

Camile Sequence for Polycondensation Reactions

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 290 | 6 | 25 |

Camile Sequence for Examples A, B, and F

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 290 | 6 | 25 |

For Example C, the same sequence in the preceding table was used, except the time was 80 min in Stage 7. For Example D, the same sequence in the preceding table was used, except the time was 50 min in Stage 7. For Example E, the same sequence in the preceding table was used, except the time was 140 min in Stage 7.

The resulting polymers were recovered from the flask, chopped using a hydraulic chopper, and ground to a 6 mm screen size. Samples of each ground polymer were submitted for inherent viscosity in 60/40 (wt/wt) phenol/tetrachloroethane at a concentration of 0.5 g/100 ml at 25° C., catalyst level (Sn) by x-ray fluorescence, and color (L*, a*, b*) by transmission spectroscopy. Polymer composition was obtained by 1H NMR. Samples were submitted for thermal stability and melt viscosity testing using a Rheometrics Mechanical Spectrometer (RMS-800).

Examples G to N

The polyesters of these examples were prepared as described above for Examples A to F, except that the target tin amount in the final polymer was 150 ppm for examples G to N. The following tables describe the temperature/pressure/stir rate sequences controlled by the Camile software for these examples.

Camile Sequence for Examples G, I, and K

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 400 | 50 |
| 5 | 110 | 290 | 400 | 50 |
| 6 | 5 | 290 | 8 | 50 |
| 7 | 110 | 295 | 8 | 50 |

For Example G, the stirrer was turned to 25 rpm with 95 min left in Stage 7.

Camile Sequence for Example H

| Stage | Time (min) | Temp (° C.) | Vacuum (torr) | Stir (rpm) |
|---|---|---|---|---|
| 1 | 10 | 245 | 760 | 0 |
| 2 | 5 | 245 | 760 | 50 |
| 3 | 30 | 283 | 760 | 50 |
| 4 | 3 | 283 | 175 | 50 |
| 5 | 5 | 283 | 5 | 50 |
| 6 | 5 | 283 | 1.2 | 50 |
| 7 | 71 | 285 | 1.2 | 50 |

For Example N, the same sequence in the preceding table was used, except the time was 75 min in Stage 7.

Camile Sequence for Example J

| Stage | Time (min) | Temp (° C.) | Vacuum (torr) | Stir (rpm) |
|---|---|---|---|---|
| 1 | 10 | 245 | 760 | 0 |
| 2 | 5 | 245 | 760 | 50 |
| 3 | 30 | 285 | 760 | 50 |
| 4 | 3 | 285 | 175 | 50 |
| 5 | 5 | 285 | 5 | 50 |
| 6 | 5 | 285 | 4 | 50 |
| 7 | 220 | 290 | 4 | 50 |

Camile Sequence for Example L

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 285 | 90 | 50 |
| 6 | 5 | 285 | 6 | 50 |
| 7 | 70 | 290 | 6 | 50 |

Camile Sequence for Example M

| Stage | Time (min) | Temp (° C.) | Vacuum (torr) | Stir (rpm) |
|---|---|---|---|---|
| 1 | 5 | 245 | 760 | 0 |
| 2 | 5 | 245 | 760 | 50 |
| 3 | 30 | 265 | 760 | 50 |
| 4 | 3 | 265 | 90 | 50 |
| 5 | 110 | 290 | 90 | 50 |
| 6 | 5 | 290 | 6 | 25 |
| 7 | 110 | 295 | 6 | 25 |

Examples O and P

Dimethyl terephthalate, 1,4-cyclohexanedimethanol, and 2,2,4,4-tetramethyl-1,3-cyclobutanediol were weighed into a 500-ml single neck round bottom flask. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 45 mol %.

Inherent viscosities were measured as described in the "Measurement Methods" section above. The compositions of the polyesters were determined by $^{1}H$ NMR as explained before in the Measurement Methods section. The glass transition temperatures were determined by DSC, using the second heat after quench at a rate of 20° C./min.

The table below shows the experimental data for the polyesters of this example. The data shows that an increase in the level of 2,2,4,4-tetramethyl-1,3-cyclobutanediol raises the glass transition temperature in an almost linear fashion, for a constant inherent viscosity. FIG. 3 also shows the dependence of Tg on composition and inherent viscosity.

TABLE 4

Glass transition temperature as a function of inherent viscosity and composition

| Example | mol % TMCD | % cis TMCD | IV (dL/g) | $T_g$ (° C.) | $\eta_o$ at 260° C. (Poise) | $\eta_o$ at 275° C. (Poise) | $\eta_o$ at 290° C. (Poise) |
|---|---|---|---|---|---|---|---|
| A | 43.9 | 72.1 | 0.46 | 131 | NA | NA | NA |
| B | 44 | 71.7 | 0.49 | 128 | NA | NA | NA |
| C | 43.6 | 72.1 | 0.52 | 128 | NA | NA | NA |
| D | 43.6 | 72.3 | 0.54 | 127 | NA | NA | NA |
| E | 43.8 | 72.2 | 0.56 | 129 | NA | NA | NA |
| F | 45.6 | 50.7 | 0.63 | 128 | NA | NA | NA |
| G | 46.3 | 52.4 | 0.52 | NA | NA | NA | NA |
| H | 45.7 | 50.9 | 0.54 | NA | NA | NA | NA |
| I | 46.3 | 52.6 | 0.56 | NA | NA | NA | NA |
| J | 46 | 50.6 | 0.56 | NA | NA | NA | NA |
| K | 46.5 | 51.8 | 0.57 | NA | NA | NA | NA |
| L | 45.6 | 51.2 | 0.58 | NA | NA | NA | NA |
| M | 46 | 51.9 | 0.58 | NA | NA | NA | NA |
| N | 45.5 | 51.2 | 0.59 | NA | NA | NA | NA |
| O | 45.8 | 50.1 | 0.624 | 125 | NA | NA | 7696 |
| P | 45.6 | 50.5 | 0.325 | 108 | NA | NA | NA |

NA = Not available

Example 5

This example illustrates the effect of the predominance of the type of 2,2,4,4-tetramethyl-1,3-cyclobutanediol isomer (cis or trans) on the glass transition temperature of the polyester.

Dimethyl terephthalate, 1,4-cyclohexanedimethanol, and 2,2,4,4-tetramethyl-1,3-cyclobutanediol were weighed into a 500-ml single neck round bottom flask. The polyesters of this example were prepared with a 1.2/1 glycol/acid ratio with the entire excess coming from the 2,2,4,4-tetramethyl-1,3-cyclobutanediol. Enough dibutyltin oxide catalyst was added to give 300 ppm tin in the final polymer. The flask was under a 0.2 SCFC nitrogen purge with vacuum reduction capability. The flask was immersed in a Belmont metal bath at 200° C. and stirred at 200 RPM after the reactants had melted. After about 2.5 hours, the temperature was raised to 210° C. and these conditions were held for an additional 2 hours. The temperature was raised to 285° C. (in approximately 25 minutes) and the pressure was reduced to 0.3 mm of Hg over a period of 5 minutes. The stirring was reduced as the viscosity increased, with 15 RPM being the minimum stirring used. The total polymerization time was varied to attain the target inherent viscosities. After the polymerization was complete, the Belmont metal bath was lowered and the polymer was allowed to cool to below its glass transition temperature. After about 30 minutes, the flask was reimmersed in the Belmont metal bath (the temperature had been increased to 295° C. during this 30 minute wait) and the polymer mass was heated until it pulled away from the glass flask. The polymer mass was stirred at mid level in the flask until the polymer had cooled. The polymer was removed from the flask and ground to pass a 3 mm screen. Variations to this procedure were made to produce the copolyesters described below with a targeted composition of 45 mol %.

Inherent viscosities were measured as described in the "Measurement Methods" section above. The compositions of the polyesters were determined by $^{1}H$ NMR as explained before in the Measurement Methods section. The glass transition temperatures were determined by DSC, using the second heat after quench at a rate of 20° C./min.

The table below shows the experimental data for the polyesters of this Example. The data shows that cis 2,2,4,4-tetramethyl-1,3-cyclobutanediol is approximately twice as effective as trans 2,2,4,4-tetramethyl-1,3-cyclobutanediol at increasing the glass transition temperature for a constant inherent viscosity.

TABLE 5

Effect of 2,2,4,4-tetramethyl-1,3-cyclobutanediol cis/trans composition on $T_g$

| Example | mol % TMCD | IV (dL/g) | $T_g$ (° C.) | η◦ at 260° C. (Poise) | η◦ □at 275° C. (Poise) | η◦ at 290° C. (Poise) | % cis TMCD |
|---|---|---|---|---|---|---|---|
| A | 45.8 | 0.71 | 119 | N.A. | N.A. | N.A. | 4.1 |
| B | 43.2 | 0.72 | 122 | N.A. | N.A. | N.A. | 22.0 |
| C | 46.8 | 0.57 | 119 | 26306 | 16941 | 6601 | 22.8 |
| D | 43.0 | 0.67 | 125 | 55060 | 36747 | 14410 | 23.8 |
| E | 43.8 | 0.72 | 127 | 101000 | 62750 | 25330 | 24.5 |
| F | 45.9 | 0.533 | 119 | 11474 | 6864 | 2806 | 26.4 |
| G | 45.0 | 0.35 | 107 | N.A. | N.A. | N.A. | 27.2 |
| H | 41.2 | 0.38 | 106 | 1214 | 757 | N.A. | 29.0 |
| I | 44.7 | 0.59 | 123 | N.A. | N.A. | N.A. | 35.4 |
| J | 44.4 | 0.55 | 118 | N.A. | N.A. | N.A. | 35.6 |
| K | 44.3 | 0.51 | 119 | N.A. | N.A. | N.A. | 36.3 |
| L | 44.0 | 0.49 | 128 | N.A. | N.A. | N.A. | 71.7 |
| M | 43.6 | 0.52 | 128 | N.A. | N.A. | N.A. | 72.1 |
| N | 43.6 | 0.54 | 127 | N.A. | N.A. | N.A. | 72.3 |
| O | 41.5 | 0.58 | 133 | 15419 | 10253 | 4252 | 88.7 |
| P | 43.8 | 0.57 | 135 | 16219 | 10226 | 4235 | 89.6 |
| Q | 41.0 | 0.33 | 120 | 521 | 351 | 2261 | 90.4 |
| R | 43.0 | 0.56 | 134 | N.A. | N.A. | N.A. | 90.6 |
| S | 43.0 | 0.49 | 132 | 7055 | 4620 | 2120 | 90.6 |
| T | 43.1 | 0.55 | 134 | 12970 | 8443 | 3531 | 91.2 |
| U | 45.9 | 0.52 | 137 | N.A. | N.A. | N.A. | 98.1 |

NA = not available

Example 6

Comparative Example

This example illustrates that a polyester based on 100% 2,2,4,4-tetramethyl-1,3-cyclobutanediol has a slow crystallization half-time.

A polyester based solely on terephthalic acid and 2,2,4,4-tetramethyl-1,3-cyclobutanediol was prepared in a method similar to the method described in Example 1A with the properties shown on Table 6. This polyester was made with 300 ppm dibutyl tin oxide. The trans/cis ratio of the 2,2,4,4-tetramethyl-1,3-cyclobutanediol was 65/35.

Films were pressed from the ground polymer at 320° C. Crystallization half-time measurements from the melt were made at temperatures from 220 to 250° C. at 10° C. increments and are reported in Table 6. The fastest crystallization half-time for the sample was taken as the minimum value of crystallization half-time as a function of temperature. The fastest crystallization half-time of this polyester is around 1300 minutes. This value contrasts with the fact that the polyester (PCT) based solely on terephthalic acid and 1,4-cyclohexanedimethanol (no comonomer modification) has an extremely short crystallization half-time (<1 min) as shown in FIG. 1.

TABLE 6

| Crystallization Half-times (min) | | | | | | | |
|---|---|---|---|---|---|---|---|
| Comonomer (mol %) | IV (dl/g) | $T_g$ (° C.) | $T_{max}$ (° C.) | at 220° C. (min) | at 230° C. (min) | at 240° C. (min) | at 250° C. (min) |
| 100 mol % F | 0.63 | 170.0 | 330 | 3291 | 3066 | 1303 | 1888 |

where: F is 2,2,4,4-Tetramethyl-1,3-cyclobutanediol (65/35 Trans/Cis)

Example 7

Sheets comprising polyesters of the invention can be prepared in a manner similar to the procedure described below.

Sheets comprising a polyester that had been prepared with a target composition of 100 mole % terephthalic acid residues, 80 mole % 1,4-cyclohexanedimethanol residues, and 20 mole % 2,2,4,4-tetramethyl-1,3-cyclobutanediol residues were produced using a 3.5 inch single screw extruder. A sheet was extruded continuously, gauged to a thickness of 177 mil and then various sheets were sheared to size. Inherent viscosity and glass transition temperature were measured on one sheet. The sheet inherent viscosity was measured to be 0.69 dl/g. The glass transition temperature of the sheet was measured to be 106° C. Sheets were then conditioned at 50% relative humidity and 60° C. for 2 weeks. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example G). The thermoformed part was visually inspected for any blisters and the degree of blistering rated as none (N), low (L), or high (H). The results below demonstrate that these thermoplastic sheets with a glass transition temperature of 106° C. can be thermoformed under the conditions shown below, as evidenced by these sheets having at least 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 86 | 145 | 501 | 64 | N |
| B | 100 | 150 | 500 | 63 | N |
| C | 118 | 156 | 672 | 85 | N |
| D | 135 | 163 | 736 | 94 | N |
| E | 143 | 166 | 760 | 97 | N |
| F | 150 | 168 | 740 | 94 | L |
| G | 159 | 172 | 787 | 100 | L |

Example 8

Sheets comprising polyesters of the invention can be prepared in a manner similar to the procedure described below.

Sheets comprising a polyester that had been prepared with a target composition of 100 mole % terephthalic acid residues, 80 mole % 1,4-cyclohexanedimethanol residues, and 20 mole % 2,2,4,4-tetramethyl-1,3-cyclobutanediol residues were produced using a 3.5 inch single screw. A sheet was extruded continuously, gauged to a thickness of 177 mil and then various sheets were sheared to size. Inherent viscosity and glass transition temperature were measured on one sheet. The sheet inherent viscosity was measured to be 0.69 dl/g. The glass transition temperature of the sheet was measured to be 106° C. Sheets were then conditioned at 100% relative humidity and 25° C. for 2 weeks. Sheets were subsequently thermoformed into a female mold having a draw ratio of 2.5:1 using a Brown thermoforming machine. The thermoforming oven heaters were set to 60/40/40% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example G). The thermoformed part was visually inspected for any blisters and the degree of blistering rated as none (N), low (L), or high (H). The results below demonstrate that these thermoplastic sheets with a glass transition temperature of 106° C. can be thermoformed under the conditions shown below, as evidenced by the production of sheets having at least 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 141 | 154 | 394 | 53 | N |
| B | 163 | 157 | 606 | 82 | N |
| C | 185 | 160 | 702 | 95 | N |
| D | 195 | 161 | 698 | 95 | N |
| E | 215 | 163 | 699 | 95 | L |
| F | 230 | 168 | 705 | 96 | L |
| G | 274 | 174 | 737 | 100 | H |
| H | 275 | 181 | 726 | 99 | H |

Example 9

Comparative Example

Sheets consisting of Kelvx 201 were produced using a 3.5 inch single screw extruder. Kelvx is a blend consisting of 69.85% PCTG (Eastar from Eastman Chemical Co. having 100 mole % terephthalic acid residues, 62 mole % 1,4-cyclohexanedimethanol residues, and 38 mole % ethylene glycol residues); 30% PC (bisphenol A polycarbonate); and 0.15% Weston 619 (stabilizer sold by Crompton Corporation). A sheet was extruded continuously, gauged to a thickness of 177 mil and then various sheets were sheared to size. The glass transition temperature was measured on one sheet and was 100° C. Sheets were then conditioned at 50% relative humidity and 60° C. for 2 weeks. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example E). The thermoformed part was visually inspected for any blisters and the degree of blistering rated as none (N), low (L), or high (H). The results below demonstrate that these thermoplastic sheets with a glass transition temperature of 100° C. can be thermoformed under the conditions shown below, as evidenced by the production of sheets having at least 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 90 | 146 | 582 | 75 | N |
| B | 101 | 150 | 644 | 83 | N |
| C | 111 | 154 | 763 | 98 | N |
| D | 126 | 159 | 733 | 95 | N |
| E | 126 | 159 | 775 | 100 | N |
| F | 141 | 165 | 757 | 98 | N |
| G | 148 | 168 | 760 | 98 | L |

Example 10

Comparative Example

Sheets consisting of Kelvx 201 were produced using a 3.5 inch single screw extruder. A sheet was extruded continuously, gauged to a thickness of 177 mil and then various sheets were sheared to size. The glass transition temperature was measured on one sheet and was 100° C. Sheets were then conditioned at 100% relative humidity and 25° C. for 2 weeks. Sheets were subsequently thermoformed into a female mold having a draw ratio of 2.5:1 using a Brown thermoforming machine. The thermoforming oven heaters were set to 60/40/40% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example H). The thermoformed part was visually inspected for any blisters and the degree of blistering rated as none (N), low (L), or high (H). The results below demonstrate that these thermoplastic sheets with a glass transition temperature of 100° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 110 | 143 | 185 | 25 | N |
| B | 145 | 149 | 529 | 70 | N |
| C | 170 | 154 | 721 | 95 | N |
| D | 175 | 156 | 725 | 96 | N |
| E | 185 | 157 | 728 | 96 | N |
| F | 206 | 160 | 743 | 98 | L |
| G | 253 | NR | 742 | 98 | H |
| H | 261 | 166 | 756 | 100 | H |

NR = Not recorded

Example 11

Comparative Example

Sheets consisting of PCTG 25976 (100 mole % terephthalic acid residues, 62 mole % 1,4-cyclohexanedimethanol residues, and 38 mole % ethylene glycol residues) were produced using a 3.5 inch single screw extruder. A sheet was extruded continuously, gauged to a thickness of 118 mil and then various sheets were sheared to size. The glass transition temperature was measured on one sheet and was 87° C. Sheets were then conditioned at 50% relative humidity and 60° C. for 4 weeks. The moisture level was measured to be 0.17 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 87° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 102 | 183 | 816 | 100 | N |
| B | 92 | 171 | 811 | 99 | N |
| C | 77 | 160 | 805 | 99 | N |
| D | 68 | 149 | 804 | 99 | N |
| E | 55 | 143 | 790 | 97 | N |
| F | 57 | 138 | 697 | 85 | N |

Example 12

Comparative Example

A miscible blend consisting of 20 wt % Teijin L-1250 polycarbonate (a bisphenol-A polycarbonate), 79.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 94° C. Sheets were then conditioned at 50% relative humidity and 60° C. for 4 weeks. The moisture level was measured to be 0.25 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 94° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 92 | 184 | 844 | 100 | H |
| B | 86 | 171 | 838 | 99 | N |
| C | 73 | 160 | 834 | 99 | N |
| D | 58 | 143 | 787 | 93 | N |
| E | 55 | 143 | 665 | 79 | N |

Example 13

Comparative Example

A miscible blend consisting of 30 wt % Teijin L-1250 polycarbonate, 69.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 99° C. Sheets were then conditioned at 50% relative humidity and 60° C. for 4 weeks. The moisture level was measured to be 0.25 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 99° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 128 | 194 | 854 | 100 | H |
| B | 98 | 182 | 831 | 97 | L |
| C | 79 | 160 | 821 | 96 | N |
| D | 71 | 149 | 819 | 96 | N |
| E | 55 | 145 | 785 | 92 | N |
| F | 46 | 143 | 0 | 0 | NA |
| G | 36 | 132 | 0 | 0 | NA |

NA = not applicable.

A value of zero indicates that the sheet was not formed because it did not pull into the mold (likely because it was too cold).

Example 14

Comparative Example

A miscible blend consisting of 40 wt % Teijin L-1250 polycarbonate, 59.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 105° C. Sheets were then conditioned at 50% relative humidity and 60° C. for 4 weeks. The moisture level was measured to be 0.265 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Examples 8A to 8E). The thermoformed part was visually inspected for any blisters and the degree of blistering rated as none (N), low (L), or high (H). The results below demonstrate that these thermoplastic sheets with a glass transition temperature of 105° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 111 | 191 | 828 | 100 | H |
| B | 104 | 182 | 828 | 100 | H |
| C | 99 | 179 | 827 | 100 | N |
| D | 97 | 177 | 827 | 100 | N |
| E | 78 | 160 | 826 | 100 | N |
| F | 68 | 149 | 759 | 92 | N |
| G | 65 | 143 | 606 | 73 | N |

Example 15

Comparative Example

A miscible blend consisting of 50 wt % Teijin L-1250 polycarbonate, 49.85 wt % PCTG 25976, and 0.15 wt % Weston 619 was produced using a 1.25 inch single screw extruder. A sheet was extruded continuously, gauged to a thickness of 118 mil and then various sheets were sheared to size. The glass transition temperature was measured on one sheet and was 111° C. Sheets were then conditioned at 50% relative humidity and 60° C. for 4 weeks. The moisture level was measured to be 0.225 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Examples A to D). The thermoformed part was visually inspected for any blisters and the degree of blistering rated as none (N), low (L), or high (H). The results below demonstrate that these thermoplastic sheets with a glass transition temperature of 111° C. can be thermoformed under the conditions shown below, as evidenced by the production of sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 118 | 192 | 815 | 100 | H |
| B | 99 | 182 | 815 | 100 | H |
| C | 97 | 177 | 814 | 100 | L |
| D | 87 | 171 | 813 | 100 | N |
| E | 80 | 160 | 802 | 98 | N |
| F | 64 | 154 | 739 | 91 | N |
| G | 60 | 149 | 0 | 0 | NA |

NA = not applicable.

A value of zero indicates that the sheet was not formed because it did not pull into the mold (likely because it was too cold).

Example 16

Comparative Example

A miscible blend consisting of 60 wt % Teijin L-1250 polycarbonate, 39.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 117° C. Sheets were then conditioned at 50% relative humidity and 60° C. for 4 weeks. The moisture level was measured to be 0.215 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 117° C. cannot be thermoformed under the conditions shown below, as evidenced by the inability to produce sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 114 | 196 | 813 | 100 | H |
| B | 100 | 182 | 804 | 99 | H |
| C | 99 | 177 | 801 | 98 | L |
| D | 92 | 171 | 784 | 96 | L |
| E | 82 | 168 | 727 | 89 | L |
| F | 87 | 166 | 597 | 73 | N |

Example 17

Comparative Example

A miscible blend consisting of 65 wt % Teijin L-1250 polycarbonate, 34.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 120° C. Sheets were then conditioned at 50% relative humidity and 60° C. for 4 weeks. The moisture level was measured to be 0.23 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 120° C. cannot be thermoformed under the conditions shown below, as evidenced by the inability to produce sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 120 | 197 | 825 | 100 | H |
| B | 101 | 177 | 820 | 99 | H |
| C | 95 | 174 | 781 | 95 | L |
| D | 85 | 171 | 727 | 88 | L |
| E | 83 | 166 | 558 | 68 | L |

Example 18

Comparative Example

A miscible blend consisting of 70 wt % Teijin L-1250 polycarbonate, 29.85 wt % PCTG 25976, and 0.15 wt % Weston 619 was produced using a 1.25 inch single screw extruder. Sheets consisting of the blend were then produced using a 3.5 inch single screw extruder. A sheet was extruded continuously, gauged to a thickness of 118 mil and then various sheets were sheared to size. The glass transition temperature was measured on one sheet and was 123° C. Sheets were then conditioned at 50% relative humidity and 60° C. for 4 weeks. The moisture level was measured to be 0.205 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw, and visually inspecting the thermoformed part. The draw was calculated as the part volume divided by the maximum part volume achieved in this set of experiments (Examples A and B). The thermoformed part was visually inspected for any blisters and the degree of blistering rated as none (N), low (L), or high (H). The results below demonstrate that these thermoplastic sheets with a glass transition temperature of 123° C. cannot be thermoformed under the conditions shown below, as evidenced by the inability to produce sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 126 | 198 | 826 | 100 | H |
| B | 111 | 188 | 822 | 100 | H |
| C | 97 | 177 | 787 | 95 | L |
| D | 74 | 166 | 161 | 19 | L |
| E | 58 | 154 | 0 | 0 | NA |
| F | 48 | 149 | 0 | 0 | NA |

NA = not applicable.

A value of zero indicates that the sheet was not formed because it did not pull into the mold (likely because it was too cold).

Example 19

Comparative Example

Sheets consisting of Teijin L-1250 polycarbonate were produced using a 3.5 inch single screw extruder. A sheet was extruded continuously, gauged to a thickness of 118 mil and then various sheets were sheared to size. The glass transition temperature was measured on one sheet and was 149° C. Sheets were then conditioned at 50% relative humidity and 60° C. for 4 weeks. The moisture level was measured to be 0.16 wt %. Sheets were subsequently thermoformed into a female mold having a draw ratio of 2.5:1 using a Brown thermoforming machine. The thermoforming oven heaters were set to 70/60/60% output using top heat only. Sheets were left in the oven for various amounts of time in order to determine the effect of sheet temperature on the part quality as shown in the table below. Part quality was determined by measuring the volume of the thermoformed part, calculating the draw and visually inspecting the thermoformed part. The draw was calculated as the part volume divided by the maximum part volume achieved in this set of experiments (Example A). The thermoformed part was visually inspected for any blisters and the degree of blistering rated as none (N), low (L), or high (H). The results below demonstrate that these thermoplastic sheets with a glass transition temperature of 149° C. cannot be thermoformed under the conditions shown below, as evidenced by the inability to produce sheets having greater than 95% draw and no blistering, without predrying the sheets prior to thermoforming.

| | Thermoforming Conditions | | Part Quality | | |
|---|---|---|---|---|---|
| Example | Heat Time (s) | Sheet Temperature (° C.) | Part Volume (mL) | Draw (%) | Blisters (N, L, H) |
| A | 152 | 216 | 820 | 100 | H |
| B | 123 | 193 | 805 | 98 | H |
| C | 113 | 191 | 179 | 22 | H |
| D | 106 | 188 | 0 | 0 | H |
| E | 95 | 182 | 0 | 0 | NA |
| F | 90 | 171 | 0 | 0 | NA |

NA = not applicable.

A value of zero indicates that the sheet was not formed because it did not pull into the mold (likely because it was too cold).

It can be clearly seen from a comparison of the data in the above relevant working examples that the polyesters of the present invention offer a definite advantage over the commercially available polyesters with regard to glass transition temperature, density, slow crystallization rate, melt viscosity, and toughness.

The invention has been described in detail with reference to the embodiments disclosed herein, but it will be understood that variations and modifications can be effected within the spirit and scope of the invention.

What is claimed is:

1. A polyester composition comprising at least one polyester which comprises:

(a) a dicarboxylic acid component comprising:

i) 80 to 100 mole % of terephthalic acid residues;

ii) 0 to 20 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 30 to 40 mole % of 2,2,4,4-tetramethyl-1,3-cyclobutanediol residues comprising greater than 55 mole % cis-2,2,4,4-tetramethyl-1,3-cyclobutanediol residues and less than 45 mole % trans-2,2,4,4-tetramethyl-1,3-cyclobutanediol residues; and ii) 60 to 70 mole % of 1,4-cyclohexanedimethanol residues, wherein the total mole % of said dicarboxylic acid component is 100 mole %, and the total mole % of said glycol component is 100 mole %; and wherein the inherent viscosity of said polyester is from 0.50 to 0.68 dL/g as determined in 60/40 (wt/wt) phenol/tetrachloroethane at a concentration of 0.5 g/100 ml at 25° C.; and wherein said polyester has a Tg of from 100 to 140° C.;

wherein said polyester has a notched Izod impact strength of at least 7.5 ft-lb/inch at 23° C. according to ASTM D256 with a 10-mil notch in a ⅛-inch thick bar;

wherein the melt viscosity of said polyester is less than 10,000 poise as measured at 1 radian/second on a rotary melt rheometer at 290° C.; and wherein said polyester composition contains no polycarbonate.

2. The polyester composition of claim 1, wherein the inherent viscosity of said polyester is from 0.55 to 0.68 dL/g.

3. The polyester composition of claim 1, wherein the inherent viscosity of said polyester is from 0.60 to 0.68 dL/g.

4. The polyester composition of claim 1 wherein said polyester has a Tg of 110 to 140° C.

5. The polyester composition of claim 1, wherein said polyester has a Tg of 100 to 130° C.

6. The polyester composition of claim 1, wherein said polyester has a Tg of 110 to 130° C.

7. The polyester composition of claim 1, wherein said polyester has a Tg of 110 to 125° C.

8. The polyester composition of claim 1, wherein the glycol component of said polyester comprises 35 to 40 mole % 2,2,4,4-tetramethyl-1,3-cyclobutanediol residues and 60 to 65 mole % 1,4-cyclohexanedimethanol resides.

9. The polyester composition of claim 1, wherein the glycol component of said polyester comprises 30 to 35 mole % 2,2,4,4-tetramethyl-1,3-cyclobutanediol residues and 65 to 70 mole % 1,4-cyclohexanedimethanol residues.

10. The polyester composition of claim 1, wherein the dicarboxylic acid component comprises 90 to 100 mole % of terephthalic acid residues.

11. The polyester composition of claim 1, wherein said 2,2,4,4-tetraethyl-1,3-cyclobutanediol residues are a mixture comprising 60 to 99 mole % of cis-2,2,4,4-tetramethyl-1,3-cyclobutanediol residues and 1 to 40 mole % of trans-2,2,4,4-tetramethyl-1,3-cyclobutanediol residues.

12. The polyester composition of claim 1, wherein said 2,2,4,4-tetramethyl-1,3-cyclobutanediol residues are a mixture comprising 70 to 99 mole % cis or greater mole % of cis-2,2,4,4-tetramethyl-1,3-cyclobutanediol residues and 1 to 30 mole % of trans-2,2,4,4-tetramethyl-1,3-cyclobutanediol residues.

13. The polyester composition of claim 1, wherein said polyester composition comprises at least one polymer chosen from at least one of the following: nylons; polyesters other than those of claim 1; polyamides; polystyrene; polystyrene copolymers; styrene acrylonitrile copolymers; acrylonitrile butadiene styrene copolymers; poly(methylmethacrylate); acrylic copolymers; poly(ether-imides); polyphenylene oxides; poly(phenylene oxide)/polystyrene blends; polyphenylene sulfides; polyphenylene sulfide/sulfones; polysulfones; polysulfone ethers; or poly(ether-ketones)of aromatic dihydroxy compounds; or mixtures thereof.

14. The polyester composition of claim 1, wherein said polyester comprises residues of at least one branching agent in an amount of 0.01 to 10 mole % based on the total mole percentage of the diol residues or diacid residues.

15. The polyester composition of claim 1, wherein said polyester composition comprises at least one thermal stabilizer.

16. The polyester composition of claim 1, having a b* value of from −10 to less than 10 and a L* values from 50 to 90 according to the L*, a* and b* color system of the CIE (international Commission on Illumination).

17. An article of manufacture comprising the polyester composition of claim 1.

18. An article of manufacture according to claim 17, comprising a container.

19. The polyester composition of claim 1, wherein said polyester comprises residues of at least one branching agent in an amount of 0.01 to 10 mole % based on the total mole percentage of the diol residues or diacid residues.

20. The article of claim 19, wherein said bottle is chosen from at least one of the following: two liter bottles, 20 ounce bottles, 16.9 ounce bottles; medical bottles; personal care bottles, carbonated sot drink bottles; hot fill bottles; water bottles; beverage bottles, or bottles comprising at least one handle.

21. The article of claim 17 chosen from at least one of the following: film, or sheet.

22. The article according to claim 17, wherein said film or sheet is chosen from at least one of the following: extruded film(s) and/or sheet(s), calendered film(s) and/or sheet(s), compression molded film(s) and/or sheet(s), solution casted film(s) and/or sheet(s).

23. The article according to claim 17, wherein said container is chosen from at least one of the following: sterilization containers; buffet steam pans; food pans or trays; frozen food trays; microwaveable food trays; hot fill containers, amorphous lids or sheets to seal or cover food trays; food storage containers; boxes; tumblers; pitchers; cups; bowls; beverage containers; retort food containers; centrifuge bowls; vacuum cleaner, or collection and treatment canisters.

24. A polyester composition comprising at least one polyester which comprises:

(a) a dicarboxylic acid component comprising:
  i) 80 to 100 mole % of terephthalic acid residues;
  ii) 0 to 20 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 30 to 40 mole % of 2,2,4,4-tetramethyl-1,3-cyclobutanediol residues comprising greater than 55 mole cis-2,2,4,4-tetramethyl-1,3-cyclobutanediol residues and less than 45 mole % trans-2,2,4,4-tetramethyl-1,3-cyclobutanediol residues; and
  ii) 60 to 70 mole % of 1,4-cyclohexanedimethanol residues,
(c) residues of at least one branching agent;

wherein the total mole % of the dicarboxylic acid component is 100 mole %, and the total mole % of the glycol component is 100 mole %; and wherein the inherent viscosity of said polyester is from 0.50 to 0.68 dL/g as determined in 60/40 (wt/wt) phenol/tetrachloroethane at a concentration of 0.5 g/100 ml at 25° C.; and wherein said polyester has a Tg of from 100 to 140° C.;

wherein said polyester has a notched Izod impact strength of at least 7.5 ft-lb/inch at 23° C. according to ASTM D256 with a 10-mil notch in a ⅛-inch thick bar; wherein the melt viscosity of said polyester is less than 10,000 poise as measured at 1 radian/second on a rotary melt rheometer at 290° C.; and wherein said polyester composition contains no polycarbonate.

25. The polyester composition of claim 24, wherein said polyester comprises residues of at least one branching agent in the amount of 0 to 10 mole % based on the total mole percentage of the diol residues or diacid residues.

26. A polyester composition comprising at least one polyester which comprises:

(a) a dicarboxylic acid component comprising:
  i) 80 to 100 mole % of terephthalic acid residues;
  ii) 0 to 20 mole % of aromatic dicarboxylic acid residues having up to 20 carbon atoms; and
  iii) 0 to 10 mole % of aliphatic dicarboxylic acid residues having up to 16 carbon atoms; and
(b) a glycol component comprising:
  i) 30 to 40 mole % of 2,2,4,4-tetramethyl-1,3-cyclobutanediol residues comprising greater than 55 mole % cis-2,2,4,4-tetramethyl-1,3-cyclobutanediol residues and less than 45 mole % trans-2,2,4,4-tetramethyl-1,3-cyclobutanediol residues; and
  ii) 60 to 70 mole % of 1,4-cyclohexanedimethanol residues,
(c) at least one thermal stabilizer or reaction product(s) thereof;

wherein the total mole % of the dicarboxylic acid component is 100 mole %, and the total mole % of the glycol component is 100 mole %; and wherein the inherent viscosity of said polyester is from 0.50 to 0.68 dL/g as determined in 60/40 (wt/wt) phenol/tetrachloroethane at a concentration of 0.5 g/100 ml at 25° C.; and wherein said polyester has a Tg of from 100 to 140° C.;

wherein said polyester has a notched Izod impact strength of at least 7.5 ft-lb/inch at 23° C. according to ASTM D256 with a 10-mil notch in a ⅛-inch thick bar; wherein the melt viscosity of sa d polyester is less than 10,000 poise as measured at 1 radian/second on a rotary melt rheometer at 290° C.; and wherein said polyester composition contains no polycarbonate.

27. An article of manufacture comprising the polyester composition of claim 1 or 26 chosen from at least one of the following: molded articles, bottles, film sheet and containers.

28. The polyester composition of claim 1 or 26 wherein the polyester composition comprises at least one additive selected from the group consisting of colorants, dyes, mold release agents, flame retardants, plasticizers, nucleating agents, UV stabilizers, glass fiber, carbon filaments, fillers, impact modifiers, and mixtures thereof.

29. A molded article comprising a polyester composition comprising at least one polyester which comprises:

(a) a dicarboxylic acid component comprising:

i) 80 to 100 mole % of terephthalic acid residues;

ii) 0 to 20 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 30 to 40 mole % of 2,2,4,4-tetramethyl-1,3-cyclobutanediol residues comprising greater than 55 mole % cis-2,2,4,4-tetramethyl-1,3-cyclobutanediol residues and less than 45 mole % trans-2,2,4,4-tetramethyl-1,3-cyclobutanediol residues; and ii) 60 to 70 mole % of 1,4-cyclohexanedimethanol residues, wherein the total mole % of the dicarboxylic acid component is 100 mole %, and the total mole % of the glycol component is 100 mole %; and wherein the inherent viscosity of said polyester is from 0.50 to 0.68 dL/g as determined in 60/40 (wt/wt) phenol/tetrachloroethane at a concentration of 0.5 g/100 ml at 25° C.; and wherein said polyester has a Tg of from 100 to 140° C.;

wherein said polyester has a notched Izod impact strength of at least 7.5 ft-lb/inch at 23° C. according to ASTM D256 with a 10-mil notch in a ⅛-inch thick bar; wherein the melt viscosity of said polyester is less than 10,000 poise as measured at 1 radian/second on a rotary melt rheometer at 29° C.; and wherein said polyester composition contains no polycarbonate.

30. A polyester composition consisting essentially of at least one polyester which comprises:

(a) a dicarboxylic acid component comprising:

i) 80 to 100 mole % of terephthalic acid residues;

ii) 0 to 20 mole % of aromatic dicarboxylic acid residues having up to 20 carbon atoms; and iii) 0 to 10 mole % of aliphatic dicarboxylic acid residues having up to 16 carbon atoms; and (b) a glycol component comprising:

i) 30 to 40 mole % of 2,2,4,4-tetramethyl-1,3-cyclobutanediol residues comprising greater than 55 mole % cis-2,2,4,4-tetramethyl-1,3-cyclobutanediol residues and less than 45 mole % trans-2,2,4,4-tetramethyl-1,3-cyclobutanediol residues; and ii) 60 to 70 mole % of 1,4-cyclohexanedimethanol residues, wherein the total mole % of the dicarboxylic acid component is 100 mole %, and the total mole % of the glycol component is 100 mole %; and wherein the inherent viscosity of said polyester is from 0.50 to 0.68 dL/g as determined in 60/40 (wt/wt) phenol/tetrachloroethane at a concentration of 0.5 g/100 ml at 25° C.; and wherein said polyester has a Tg of from 100 to 140° C.;

wherein said polyester has a notched Izod impact strength of at least 7.5 ft-lb/inch at 23° C. according to ASTM D256 with a 10-mil notch in a ⅛-inch thick bar; wherein the melt viscosity of said polyester is less than 10,000 poise as measured at 1 radian/second on a rotary melt rheometer at 290° C.; and wherein said polyester composition contains no polycarbonate.

31. The polyester composition according to any of claim 24, 26, 29, or 30 wherein said 2,2,4,4-tetramethyl-1,3-cyclobutanediol is a mixture comprising 60 to 99 mole % of cis-2,2,4,4-tetramethyl-1,3-cyclobutanediol and 1 to 40 mole % of trans-2,2,4,4-tetramethyl-1,3-cyclobutanediol.

32. The polyester composition according to any of claim 24, 26, 29, or 30 wherein said 2,2,4,4-tetramethyl-1,3-cyclobutanediol is a mixture comprising 70 to 99 mole % cis or greater mole % of cis-2,2,4,4-tetramethyl-1,3-cyclobutanediol and 1 to 30 mole % of trans-2,2,4,4-tetramethyl-1,3-cyclobutanediol.

* * * * *